United States Patent [19]

Tanaka et al.

[11] Patent Number: 4,466,980
[45] Date of Patent: Aug. 21, 1984

[54] THIAPROSTAGLANDIN E₁ DERIVATIVES, PROCESS FOR PRODUCTION THEREOF, AND PHARMACEUTICAL USE THEREOF

[75] Inventors: Toshio Tanaka, Hino; Takeshi Toru, Hachioji; Takeo Oba, Hino; Noriaki Okamura, Chofu; Kenzo Watanabe, Hino; Kiyoshi Bannai, Hino; Atsuo Hazato, Hino; Seizi Kurozumi, Kokubunji; Fukuyoshi Kamimoto, Hino; Akira Ohtsu, Ohme, all of Japan

[73] Assignee: Teijin Limited, Osaka, Japan

[21] Appl. No.: 316,902

[22] Filed: Oct. 30, 1981

[30] Foreign Application Priority Data

Oct. 31, 1980 [JP] Japan .................................. 55-152214
Dec. 26, 1980 [JP] Japan .................................. 55-183727
Apr. 6, 1981 [JP] Japan .................................. 56-50491

[51] Int. Cl.³ .................. C07C 177/00; A61K 31/557
[52] U.S. Cl. ..................................... 424/305; 424/317; 424/331; 424/325; 560/106; 560/119; 560/121; 560/230; 562/501; 562/503; 564/188; 564/189; 568/367; 568/379; 556/427; 548/530; 546/102; 546/226; 544/161; 544/391; 542/426; 549/420; 549/475

[58] Field of Search ............... 560/121, 231, 119, 106; 562/503, 501; 424/305, 317, 331, 325; 564/188, 189; 568/367, 379; 556/427; 548/530; 546/226, 102; 544/161, 391; 542/426; 549/420, 475

[56] References Cited

U.S. PATENT DOCUMENTS 4,175,201 11/1979 Fried .................................. 562/503
4,180,672 12/1979 Kurozumi ........................... 562/503

FOREIGN PATENT DOCUMENTS 51-109452 9/1976 Japan .

OTHER PUBLICATIONS

J. Org. Chem., vol. 40, 1975, pp. 521–523.
Tetrahedron Letters, No. 10, 1975, pp. 765–768.
Journal of Medicinal Chemistry, 1977, vol. 20, No. 12, pp. 1662–1665.
J. Am. Chem. Soc., 96, 1974, pp. 6759–6761.
Tetrahedron Letters, No. 48, 1974, pp. 4267–4270.
Tetrahedron Letters, No. 51/52, 1974, pp. 4459–4462.
Tetrahedron Letters, No. 52, 1976, pp. 4793–4796.
Tetrahedron Letters, No. 13, 1975, pp. 1165–1168.
Tetrahedron Letters, No. 19, 1977, pp. 1629–1632.

Primary Examiner—Robert Gerstl
Attorney, Agent, or Firm—Wenderoth, Lind & Ponack

[57] ABSTRACT

A novel compound selected from the group consisting of 7-(or 6- or 4-)thiaprostaglandin E₁ derivatives of the formula (I).

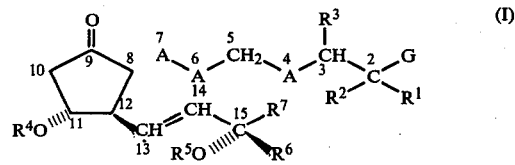

wherein A represents —CH₂— or

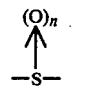

in which n is 0, 1 or 2, provided that only one A cut of three is

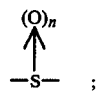

$R^1$–$R^7$ and G are as defined in the specification, the 15-epimers of said thiaprostaglandin E₁ derivatives, the enatiomers of said thiaprostaglandin E₁ derivatives or their 15-epimers, and mixtures of these compounds.

A 7-thiaprostaglandin E₁ derivative and/or its optical isomer may be prepared by reacting a 2-organo-2-cyclopentenone (II) with an organic copper-lithium compound (III) to effect conjugation reaction. A 6-thiaprostaglandin E₁ derivative and/or its optical isomer may be prepared by subjecting an α,β-unsaturated ketone (IV) and a thiol (V) to the Michael addition reaction. And, 4-thiaprostaglandin derivative and/or its optical isomer may also be prepared by the Michael addition reaction from a 2-allyl substituted cyclopentanone (VI) and a thiol (VIII).

Some compounds ((I)-1) amongst the compounds of the formula (I) and/or their optical isomer are useful for controlling vascular actions such as angina pectoris, vasodilation etc.

14 Claims, No Drawings

THIAPROSTAGLANDIN E₁ DERIVATIVES, PROCESS FOR PRODUCTION THEREOF, AND PHARMACEUTICAL USE THEREOF

This invention relates to novel thiaprostaglandin $E_1$ derivatives, processes for their production, and their pharmaceutical use. More specifically, the invention pertains to novel 7-, 6-, or 4-thiaprostaglandin $E_1$ derivatives, processes for producing these derivatives and their use for controlling vascular actions.

Since natural prostaglandins are known as local hormones having high biological and pharmacological activities, much work has been done on derivatives of natural prostaglandins. In particular, prostaglandins $E_1$ have strong platelet aggregation inhibiting activity and strong vasodilating activity, and are expected to find clinical applications.

The greatest defect of natural prostaglandins, particularly prostaglandins $E_1$, is that because they undergo rapid metabolism when administered orally, they are usually administered by intravenous injection.

Various investigations have been undertaken previously on artificial prostaglandins resulting from substitution of a sulfur atom for one or two carbon atoms forming the skeleton of natural prostaglandins. Such artificial prostaglandins include, for example, 1S-prostaglandins $E_2$ or $F_{2\alpha}$ [J. Org. Chem., 40, 521 (1975) and Japanese Laid-Open Patent Publication No. 34747/1978] having a skeleton resulting from substitution of a sulfur atom for the carbon atom at the 1-position (since the sulfur atom is present at the 1-position, these compounds are expressed by prefixing 1S; compounds in which other positions are substituted by sulfur are likewise expressed by prefixing the sulfur-substituted position numbers and S); 3S-11-deoxyprostaglandins $E_1$ [Tetrahedron Letters, 1975 765 and J. Med. Chem., 20, 1662 (1977)]; 7S-prostaglandins $F_{1\alpha}$ [J. Amer. Chem. Soc., 96, 6757, (1974)]; 9S-prostaglandins $E_1$ [Tetrahedron Letters, 1974, 4267 and 4459, ibid. 1976, 4793, and Hetrocycles, 6, 1097 (1977)]; 11S-prostaglandins $E_1$ or $F_{1\alpha}$ [Tetrahedron Letters, 1975, 1165]; 13S-prostaglandins E or F (U.S. Pat. No. 4,080,458); and 15S-prostaglandins $E_2$ (Tetrahedron Letters, 1977, 1629).

The specification of U.S. Pat. No. 4,180,672 whose inventorship includes some of the inventors of the present application discloses 7S- or 7S,13S-prostaglandins E or F represented by the following formula

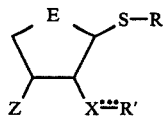

wherein E represents

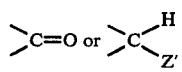

in which Z′ represents a hydrogen atom, a hydroxyl group or a protected hydroxyl group; X represents —S—, —CH₂—, or —CH=; ═ represents a single or double bond; R¹ represents a monovalent or divalent organic group containing 1 to 25 carbon atoms; and Z represents a hydrogen atom, a hydroxyl group or a protected hydroxyl group; with the proviso that when both E and Z represent a hydroxyl group or a protected hydroxyl group, X represents —S—.

This U.S. Patent specification, however, disclose only some of 11-deoxy-7S-prostaglandins $E_1$ belonging to 7S-prostaglandins E as specific examples of 7S-prostaglandins within the general formula given above (Examples 20 to 23 and Compounds 84 to 87, 94 and 95 of the U.S. Patent). This U.S. Patent also states that the compounds of the general formula given above have gastric secretion inhibiting action, anti-inflammatory action, platelet aggregation inhibiting action, etc. But it is only their gastric secretion inhibiting action which is demonstrated by specific data given in the specification, and data for other pharmacological activities are not given in the specification.

Investigations of the present inventors have shown that 11-deoxy-7S-prostaglandines $E_1$ specifically disclosed in U.S. Pat. No. 4,180,672, i.e., 11-deoxy-7S-prostaglandin $E_1$, its methyl ester, 11-deoxy-17-methyl-7S-prostaglandin $E_1$ and its methyl ester, have platelet aggregation inhibiting activity, which, however, is very weak.

It is an object of this invention therefore to provide novel thiaprostaglandin $E_1$ derivatives.

Another object of this invention is to provide novel thiaprostaglandin $E_1$ derivatives which are used to control vascular actions.

Still another object of this invention is to provide novel thiaprostaglandin $E_1$ derivatives which by oral administration, fully and continuously exhibit activity for controlling vascular actions.

Yet another object of this invention is to provide novel thiaprostaglandins $E_1$ having reduced side-effects upon administration.

A further object of this invention is to provide processes for producing the novel thiaprostaglandin $E_1$ derivatives of the invention.

Other objects and advantages of the invention will become apparent from the following description.

These objects and advantages are achieved in accordance with this invention by a compound selected from the group consisting of thiaprostaglandins $E_1$ represented by the following general formula (I)

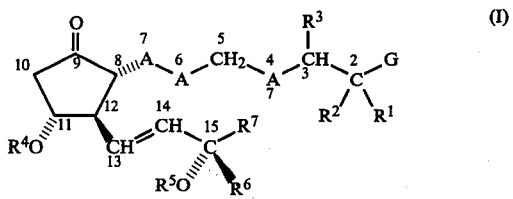

wherein A represents —CH₂— or

in which n is 0, 1 or 2 provided that only one A out of three is

G represents —COOR$^8$, —CONR$^9$R$^{10}$ or —CH$_2$OR$^{11}$ in which R$^8$ represents a hydrogen atom, a C$_1$–C$_{10}$ alkyl group, a substituted or unsubstituted phenyl group, a substituted or unsubstituted alicyclic group, a substituted or unsubstituted phenyl(C$_1$–C$_2$)alkyl group or one equivalent of cation, R$^9$ and R$^{10}$ are identical or different and each represents a hydrogen atom, a C$_1$–C$_{10}$ alkyl group, a substituted or unsubstituted C$_5$–C$_6$ alicyclic group, a substituted or unsubstituted phenyl group or a substituted or unsubstituted phenyl (C$_1$–C$_2$)alkyl group, or R$^9$ and R$^{10}$, taken together with the nitrogen atom to which they are bonded may form a substituted or unsubstituted 5- or 6-membered ring which may include a hetero atom, and R$^{11}$ represents a hydrogen atom, a C$_1$–C$_6$ alkyl group, a substituted or unsubstituted C$_2$–C$_7$ acyl group, a tri(C$_1$–C$_6$)hydrocarbon-silyl group, or a group forming an acetal linkage together with the oxygen atom of the hydroxyl group; R$^1$ and R$^2$ are identical or different and each represents a hydrogen atom, a halogen atom, a methyl group or an ethyl group; R$^3$ represents a hydrogen atom or together with R$^1$ may form a bond; R$^4$ and R$^5$ are identical or different, and each represents a hydrogen atom, a tri(C$_1$–C$_6$) hydrocarbon-silyl group, or a group forming an acetal linkage together with the oxygen atom of the hydroxyl group; R$^6$ represents a hydrogen atom, a methyl group, or an ethynyl group which may be protected; and R$^7$ represents a C$_5$–C$_8$ alkyl group or a substituted or unsubstituted 5- or 6 -membered alicyclic group; their 15-epimers, the enantiomers of said thiaprostaglandin E$_1$ derivatives and their 15-epimers, and mixtures of these compounds.

The 15-epimers of the thiaprostaglandins E$_1$ derivatives of formula (I) are compounds of formula (I)′

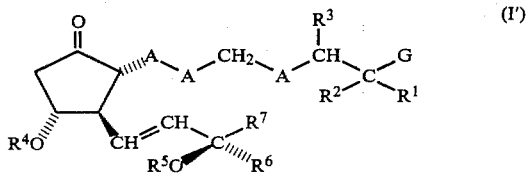

(I′)

wherein all symbols are as defined with regard to formula (I). These compounds differ from the compounds of formula (I) in regard to the configuration of the asymmetric carbon atom at the 15-position.

The enantiomers of the compounds of formula (I) or (I)′ are compounds represented by formula (I)ent

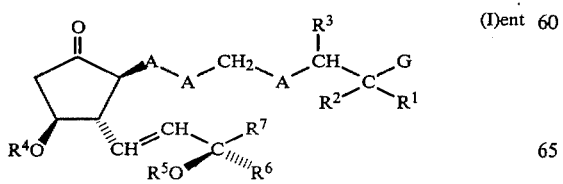

(I)ent or formula (I)′ent

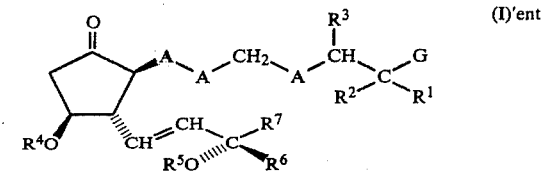

(I)′ent wherein all symbols are as defined with regard to formula (I). The compounds of formula (I)ent or (I)′ent differ from the compounds of formula (I) in regard to the configurations of the asymmetric carbon atoms at the 8-, 11-, 12- and 15-positions.

The mixtures of these compounds in accordance with this invention denote a stereoisomeric mixture consisting of at least two compounds selected from the compounds of formulae (I), (I)′, (I)ent and (′)′ent in any desired mixing ratios.

In the formulae (I), (I)′, (I)ent and (I)′ent, A is —CH$_2$— or

in which n is 0, 1 or 2. When n is 0, 1 or 2,

in which n is 0, 1 or 2. When n is 0, 1 or 2,

respectively represents —S—,

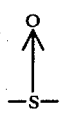

or —SO$_2$—. Of the three A groups, only one A is

and the other two A groups are —CH$_2$—. According to the position at which

exists, the compound of formula (I) is named in this invention by prefixing a combination of the number of the position and S showing a sulfur atom, as 7S-, 6S-, or 4S-.

G in the formulae represents —COOR$^8$, —CONR$^9$R$^{10}$, or —CH$_2$OR$^{11}$. R$^8$ represents a hydrogen atom, a $C_1$–$C_{10}$ alkyl group, a substituted or unsubstituted phenyl group, a substituted or unsubstituted alicyclic group, a substituted or unsubstituted phenyl(-$C_1$–$C_2$)-alkyl group, or one equivalent of cation.

The $C_1$–$C_{10}$ alkyl groups are linear or branched alkyl groups having 1 to 10 carbon atoms such as methyl, ethyl, n-propyl, iso-propyl, n-butyl, sec-butyl, tert-butyl, n-pentyl, n-hexyl, n-heptyl, n-octyl, n-nonyl and n-decyl.

Preferred substituents for the substituted phenyl group are a halogen atom, a hydroxyl group, a $C_2$–$C_7$ acyloxy group, a $C_1$–$C_4$ alkyl group which may be substituted by a halogen atom, a $C_1$–$C_4$ alkoxy group which may be substituted by a halogen atom, a nitrile group, a carboxyl group, or a ($C_1$–$C_6$)alkoxycarbonyl group. The halogen atom includes fluorine, chlorine and bromine, the fluorine and chlorine being preferred. Examples of the $C_2$–$C_7$ acyloxy group are acetoxy, propionyloxy, n-butyryloxy, iso-butyryloxy, n-valeryloxy, iso-valeryloxy, caproyloxy, enanthoyloxy and benzoyloxy. Examples of the $C_1$–$C_4$ alkyl group which may be substituted by one or more halogen atoms are methyl, ethyl, n-propyl, iso-propyl, n-butyl, chloromethyl, dichloromethyl, and trifluoromethyl. Preferred examples of the $C_1$–$C_4$ alkoxy group which may be substituted by one or more halogen atoms are methoxy, ethoxy, n-propoxy, iso-propoxy, n-butoxy, chloromethoxy, dichloromethoxy and trifluoromethoxy. Examples of the ($C_1$–$C_6$) alkoxycarbonyl group include methoxycarbonyl, ethoxycarbonyl, butoxycarbonyl and hexyloxycarbonyl.

The substituted phenyl group may have 1 to 3, preferably 1, such substituents as exemplified above.

The substituted or unsubstituted alicyclic group includes, for example, saturated or unsaturated $C_5$–$C_8$, preferably $C_5$–$C_6$, especially preferably $C_6$, alicyclic groups which are unsubstituted or substituted by the same substituents as exemplified hereinabove, such as cyclopentyl, cyclohexyl, cyclohexenyl, cycloheptyl, and cyclooctyl.

Examples of the substituted or unsubstituted phenyl(-$C_1$–$C_2$) alkyl group are benzyl, α-phenethyl and β-phenethyl in which the phenyl group is unsubstituted or substituted by the same substituents as exemplified hereinabove.

Examples of one equivalent of cation are ammonium cations such as $NH_4^+$, tetramethylammonium, monomethylammonium, dimethylammonium, trimethylammonium, benzylammonium, phenethylammonium, morpholium cation, monoethanolammonium, and piperidium cation; alkali metal cations such as $Na^+$ and $K^+$; and divalent or trivalent metallic cations such as $\frac{1}{2}Ca^{2+}$, $1/2Mg^{2+}$, $\frac{1}{2}Zn^{2+}$, and $\frac{1}{3}Al^{3+}$.

The group —$COOR^8$, according to the type of $R^8$, represents a carboxyl group in free form ($R^8$=H), a carboxyl group in salt form ($R^8$=one equivalent of cation), or a carboxylate ester group ($R^8$=H or other groups given above except one equivalent of cation).

$R^9$ and $R^{10}$ in the group —$CONR^9R^{10}$ represented by G are identical or different, and each represents a hydrogen atom, a $C_1$–$C_{10}$ alkyl group, a substituted or unsubstituted $C_5$–$C_6$ alicyclic group, a substituted or unsubstituted phenyl group, or a substituted or unsubstituted phenyl ($C_1$–$C_2$) alkyl group. Specific examples are the same as those exemplified hereinabove with regard to $R^8$. $R^9$ and $R^{10}$, when taken together with the nitrogen atom to which they are bonded, may form a substituted or unsubstituted 5- or 6-membered ring which may further include a hetero atom. Examples of the substituent may be those exemplified hereinabove. The hetero atom is, for example, nitrogen, sulfur or oxygen atoms. Examples of the ring are 1-pyrrolidyl, thiazolyl, 1-piperidyl, morpholyl, piperadyl and dibenzopiperidyl each as 5,6-dihydrophenanthridyl.

$R^{11}$ in —$CH_2OR^{11}$ represented by G is a hydrogen atom, a $C_1$–$C_6$ alkyl group, or a substituted or unsubstituted $C_2$–$C_7$ acyl group. Specific examples of these groups may be the same as those exemplified hereinabove with regard to $R^8$.

$R^{11}$ may also represent a tri($C_1$–$C_6$)hydrocarbonsilyl group or a group forming an acetal linkage together with the oxygen atom of the hydroxyl group. Examples of the tri($C_1$–$C_6$ hydrocarbon-silyl group tri($C_1$–$C_4$)alkylsilyl groups such as trimethylsilyl, triethylsilyl, and t-butyldimethylsilyl, and diphenyl($C_1$–$C_4$)alkylsilyl groups such as t-butyldiphenylsilyl.

Examples of the group forming an acetal linkage together with the oxygen atom of the hydroxyl group are methoxymethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofuranyl and 6,6-dimethyl-3-oxa-2-oxo-bicyclo[3.1.0]hex-4-yl. Of these, 2-tetrahydropyranyl, 2-tetrahydrofuranyl, 1-ethoxymethyl, 2-methoxy-2-propyl, (2-methoxyethoxy)methyl, and 6,6-dimethyl-3-oxa-2-oxo-bicyclo[3.1.0]hex-4-yl are preferred.

It should be understood that these hydrocarbon-silyl groups and acetal linkage-forming groups are protective groups for the hydroxyl group. These protective groups can be easily removed under acidic to neutral conditions.

The group —$CH_2OR^{11}$, according to the type of $R^{11}$, represents a hydroxymethyl group ($R^{11}$=H), an alkoxymethyl group ($R^{11}$=$C_1$–$C_6$ alkyl group), or an acyloxymethyl group ($R^{11}$=$C_2$–$C_7$ acyl group).

$R^1$ and $R^2$ are identical or different, and each represents a hydrogen atom, a halogen atom, a methyl group, or an ethyl group. Examples of the halogen atom are fluorine, chlorine and bromine aoms, the fluorine atom being especially preferred.

$R^3$ is a hydrogen atom, or may form a bond together with $R^1$. It should be understood that when $R^1$ and $R^3$ together form a bond, the corresponding portion in formula (I) forms a group of the following formula

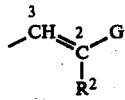

Preferably, $R^1$ and $R^2$ are identical or different and each represents a fluorine atom or a methyl group and $R^3$ represents a hydrogen atom; or $R^1$ and $R^3$ together form a bond and $R^2$ is a hydrogen atom.

$R^4$ and $R^5$ are identical or different, and each represents a hydrogen atom, a tri($C_1$–$C_6$)hydrocarbon-silyl group or a group forming an acetal linkage together with the oxygen atom of the hydroxyl group. Specific examples of these groups are the same as those given with regard to $R^{11}$.

$R^6$ represents a hydrogen atom, a methyl group or an ethynyl group (—C≡CH) which may be protected, the hydrogen atom and the methyl group being preferred.

$R^7$ represents a $C_5$–$C_8$ alkyl group, or a substituted or unsubstituted 5- or 6-membered alicyclic group. The $C_5-C_8$ alkyl group may be linear or branched, and includes, for example, n-pentyl, n-hexyl, 2-hexyl, 2-methylhexyl, n-heptyl, and n-octyl. The n-pentyl, n-hexyl, 2-hexyl and 2-methylhexyl are preferred. Examples of the substituted or unsubstituted 5- or 6-membered alicyclic group are cyclopentyl and cyclohexyl which may be substituted by the same substituents exemplified hereinabove with regard to $R^8$. The unsubstituted cyclohexyl group is preferred.

For the sake of convenience, the thiaprostaglandin $E_1$ derivatives of the invention can be divided into the following three groups according to the position at which the sulfur atom is present.

(1) 7-Thiaprostaglandin $E_1$ derivatives of formula (I)-a

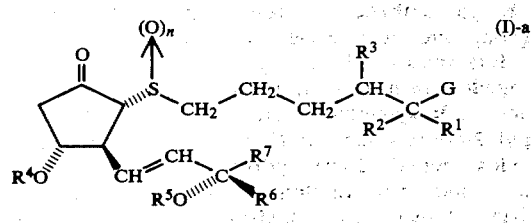

wherein all symbols are as defined with regard to formula (I); their 15-epimers; the enantiomers of said derivatives, and their 15-epimers; and mixtures of these compounds.

(2) 6-Thiaprostaglandin derivatives $E_1$ of formula (I)-b

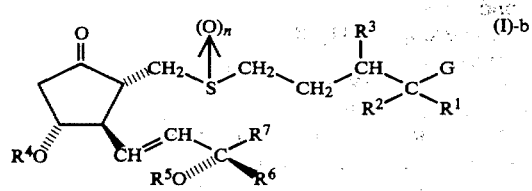

wherein all symbols are as defined with regard to formula (I), their 15-epimers; the enantiomers of said derivatives and their 15-epimers; and mixtures of these compounds.

(3) 4-Thiaprostaglandin $E_1$ derivatives of formula (I)-c

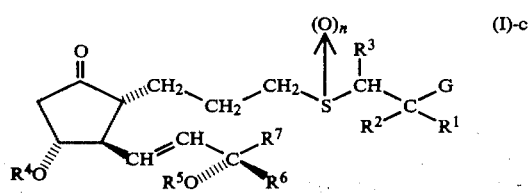

wherein all symbols are as defined with regard to formula (I); their 15-epimers; the enantiomers of said derivatives and their 15-epimers; and mixtures of these compounds.

According to this invention, there are preferably provided compounds of general formula (I) including the formulae (I)-a, (I)-b and (I)-c, that is, thiaprostaglandin $E_1$ derivatives (to be referred to as natural-type prostaglandin $E_1$ derivatives) which have the same configuration of asymmetric carbon atoms at the 8-, 11-, 12- and 15-positions as natural prostaglandins $E_1$.

According to this invention, there are also provided thiaprostaglandins $E_1$ derivatives represented by the following formula (I)-1

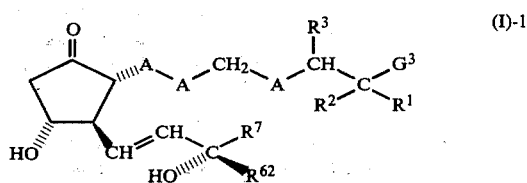

wherein $R^1$, $R^2$, $R^3$ and $R^7$ are as defined with regard to formula (I); A represents —$CH_2$— or —S— provided that only one A out of three represents —S—; $G^3$ represents —$COOR^8$, —$CONH_2$ or —$CH_2OR^{12}$ in which $R^8$ represents a hydrogen atom, a $C_1-C_{10}$ alkyl group, a substituted or unsubstituted phenyl group, a substituted or unsubstituted alicyclic group, a substituted or unsubstituted phenyl ($C_1-C_2$) alkyl group, or one equivalent of a cation whose salt is pharmaceutically acceptable, and $R^{12}$ represents a hydrogen atom, a $C_1-C_6$ alkyl group or a substituted or unsubstituted $C_2-C_7$ acyl group; and $R^{62}$ represents a hydrogen atom, a methyl group or an ethynyl group, their 15-epimers; the enantiomers of said derivatives or their 15-epimers [excepting the enantiomers of the 6-thiaprostaglandin $E_1$ derivatives of formula (I)-1 or their 15-epimers ], that is, a group of compounds in which the hydroxyl groups bonded to the carbon atoms at the 11- and 15-positions are free, and which can be directly administered to warm-blooded animals.

Specific examples of the thiaprostaglandin $E_1$ derivatives of formula (I) (natural-type prostaglandin $E_1$ derivatives) are given below.

| Compounds of formula (I) in which only A at the 7-position is —S— | |
|---|---|
| (100) | 7-Thiaprostaglandin $E_1$, |
| (101) | 20-methyl-7-thiaprostaglandin $E_1$, |
| (102) | 20-ethyl-7-thiaprostaglandin $E_1$, |
| (103) | 16-methyl-7-thiaprostaglandin $E_1$, |
| (104) | 16,20-dimethyl-7-thiaprostaglandin $E_1$, |
| (105) | 17-methyl-7-thiaprostaglandin $E_1$, |
| (106) | 17,20-dimethyl-7-thiaprostaglandin $E_1$, |
| (107) | 17(S),20-dimethyl-7-thiaprostaglandin $E_1$, |
| (108) | 17(R),20-dimethyl-7-thiaprostaglandin $E_1$, |
| (109) | 20-ethyl-16-methyl-7-thiaprostaglandin $E_1$, |
| (110) | 20-ethyl-17-methyl-7-thiaprostaglandin $E_1$, |
| (111) | 16,17,18,19,20-pentanor-15-cyclohexyl-7-thiaprostaglandin $E_1$, |
| (112) | 16,17,18,19,20-pentanor-15-cyclohexyl-2-methyl-7-thiaprostaglandin $E_1$, |
| (113) | 16,17,18,19,20-pentanor-15-cyclohexyl-2,2-dimethyl-7-thiaprostaglandin $E_1$, |
| (114) | 16,17,18,19,20-pentanor-15-cyclohexyl-2-ethyl-7-thiaprostaglandin $E_1$, |
| (115) | 16,17,18,19,20-pentanor-15-cyclohexyl-2-fluoro-7-thiaprostaglandin $E_1$, |
| (116) | 16,17,18,19,20-pentanor-15-cyclohexyl-2,2-difluoro-7-thiaprostaglandin $E_1$, |
| (117) | 16,17,18,19,20-pentanor-15-cyclopentyl-7-thiaprostaglandin $E_1$, |
| (118) | 16,17,18,19,20-pentanor-15-cyclohexyl-2,3-dehydro-7-thiaprostaglandin $E_1$, |
| (119) | 17,20-dimethyl-2,3-dehydro-7-thiaprostaglandin $E_1$, |
| (120) | 17(S),20-dimethyl-2,3-dehydro-7-thiaprostaglandin $E_1$, |
| (121) | 17(R),20-dimethyl-2,3-dehydro-7-thiaprostaglandin $E_1$, |

| | |
|---|---|
| (122) | 15-methyl-7-thiaprostaglandin E₁, |
| (123) | 15,20-methyl-7-thiaprostaglandin E₁, |
| (124) | methyl ester of (100), |
| (125) | ethyl ester of (101), |
| (126) | n-propyl ester of (102), |
| (127) | n-butyl ester of (103), |
| (128) | methyl ester of (104), |
| (129) | n-pentyl ester of (105), |
| (130) | methyl ester of (106), |
| (131) | methyl ester of (107), |
| (132) | ethyl ester of (107), |
| (133) | n-hexyl ester of (107), |
| (134) | methyl ester of (108), |
| (135) | n-octyl ester of (108), |
| (136) | methyl ester of (109), |
| (137) | ethyl ester of (110), |
| (138) | methyl ester of (110), |
| (139) | ethyl ester of (111), |
| (140) | isopropyl ester of (111), |
| (141) | t-butyl ester of (111), |
| (142) | n-hexyl ester of (111), |
| (143) | n-decyl ester of (111), |
| (144) | phenyl ester of (111), |
| (145) | p-methylphenyl ester of (111), |
| (146) | p-fluorophenyl ester of (111), |
| (147) | benzyl ester of (111), |
| (148) | α-phenethyl ester of (111), |
| (149) | β-phenethyl ester of (111), |
| (150) | methyl ester of (112), |
| (151) | methyl ester of (113), |
| (152) | ethyl ester of (114), |
| (153) | methyl ester of (115), |
| (154) | methyl ester of (116), |
| (155) | methyl ester of (117), |
| (156) | methyl ester of (118), |
| (157) | benzyl ester of (118), |
| (158) | methyl ester of (119), |
| (159) | phenyl ester of (119), |
| (160) | methyl ester of (120), |
| (161) | decyl ester of (120), |
| (162) | methyl ester of (121), |
| (163) | methyl ester of (122), |
| (164) | methyl ester of (123), |
| (165) | sodium salt of (100), |
| (166) | sodium salt of (106), |
| (167) | potassium salt of (106), |
| (168) | ammonium salt of (106), |
| (169) | sodium salt of (107), |
| (170) | ethanol ammonium salt of (107), |
| (171) | sodium salt of (111), |
| (172) | calcium salt of (111), |
| (173) | morpholium salt of (111), |
| (174) | amide of (100), |
| (175) | amide of (107), |
| (176) | N,N—diethylamide of (107), |
| (177) | piperidinamide of (107), |
| (178) | amide of (111), |
| (179) | morpholinamide of (111), |
| (180) | 5,6-dihydrophenanthridinamide of (111), |
| (181) | 1-nor-2-hydroxymethyl-7-thiaprostaglandin E₁, |
| (182) | 1-nor-2-hydroxymethyl-17(S),20-dimethyl-7-thiaprostaglandin E₁, |
| (183) | 1-nor-2-acetoxymethyl-17(S),20-dimethyl-7-thiaprostaglandin E₁, |
| (184) | 1-nor-2-benzoyloxymethyl-17(S),20-dimethyl-7-thiaprostaglandin E₁, |
| (185) | 1,16,17,18,19,20-hexanor-2-hydroxymethyl-15-cyclohexyl-7-thiaprostaglandin E₁, |
| (186) | 1,16,17,18,19,20-hexanor-2-acetoxymethyl-15-cyclohexyl-7-thiaprostaglandin E₁, |
| (187) | 1,16,17,18,19,20-hexanor-2-benzoyloxymethyl-15-cyclohexyl-7-thiaprostaglandin E₁, |
| (188) | 1,16,17,18,19,20-hexanor-2-trimethylsiloxymethyl-15-cyclohexyl-7-thiaprostaglandin E₁, |
| (189) | S—oxide of (100), |
| (190) | S—oxide of (124), |
| (191) | S—oxide of (107), |
| (192) | S—oxide of (131), |
| (193) | S—oxide of (132), |
| (194) | S—oxide of (111), |
| (195) | S—oxide of (138), |
| (196) | S—oxide of (143), |
| (197) | S—oxide of (144), |
| (198) | S—oxide of (147), |
| (199) | 11,15-bis(t-butyldimethylsilyl)ether of (124), |
| (200) | 11,15-bis(2-tetrahydropyranyl)ether of (124), |
| (201) | 11-(2-tetrahydropyranyl)-15-t-butyldimethylsilyl ether of (124), |
| (202) | 11-t-butyldiphenylsilyl-15-(2-tetrahydropyranyl)ether of (125), |
| (203) | 11,15-bis(t-butyldimethylsilyl)ether of (131), |
| (204) | 11-(6,6-dimethyl-3-oxa-2-oxo-bicyclo[3.1.0]-hex-4-yl-15-t-butyldimethylsilyl ether of (131), |
| (205) | 11,15-bis(t-butyldimethylsilyl)ether of (138), |
| (206) | 15-t-butyldimethylsilyl-11-trimethylsilyl ether of (138), |
| (207) | 15-t-butyldimethyl-11-(2-tetrahydropyranyl) silyl ether of (143), |
| (208) | 15-t-butyldimethylsilyl-11-(2-tetrahydropyranyl)ether of (144), |
| (209) | 15-t-butyldimethylsilyl-11-(2-tetrahydropyranyl)ether of (147), |
| (210) | 11,15-bis(t-butyldimethylsilyl)ether of (179), |
| (211) | 11,15-bis(t-butyldimethylsilyl)ether of (180), |
| (212) | 1,11,15-tris(t-butyldimethylsilyl)ether, |
| (213) | 11,15 bis(t-butyldimethylsilyl)ether of (186), |
| (214) | 11,15-bis(t-butyldimethylsilyl)ether of (188), |
| (215) | 11,15-bis(t-butyldimethylsilyl)ether of (150), |
| (216) | 11,15-bis(t-butyldimethylsilyl)ether of (151), |
| (217) | 11,15-bis(t-butyldimethylsilyl)ether of (154), |
| (218) | 11,15-bis(t-butyldimethylsilyl)ether of (156), |
| (219) | 11,15-bis(t-butyldimethylsilyl)ether of (160), and |
| (220) | 11,15-bis(t-butyldimethylsilyl)ether of (111). |

Compounds of formula (I) in which A at the 6-position alone is $-\overset{(O)_n}{\underset{}{S}}-$

| | |
|---|---|
| (300) | 6-Thiaprostaglandin E₁, |
| (301) | 20-methyl-6-thiaprostaglandin E₁, |
| (302) | 17,20-dimethyl-6-thiaprostaglandin E₁, |
| (303) | 16,17,18,19,20-pentanor-15-cyclohexyl-6-thiaprostaglandin E₁, |
| (304) | 15-methyl-6-thiaprostaglandin E₁, |
| (305) | methyl ester of (300), |
| (306) | methyl ester of (301), |
| (307) | methyl ester of (302), |
| (308) | methyl ester of (303), |
| (309) | phenyl ester of (303), |
| (310) | benzyl ester of (303), |
| (311) | methyl ester of (304), |
| (312) | sodium salt of (301), |
| (313) | ammonium salt of (302), |
| (314) | sodium salt of (303), |
| (315) | ethanolammonium salt of (303), |
| (316) | S—oxide of (305), |
| (317) | S—dioxide of (305), |
| (318) | amide of (302), |
| (319) | amide of (303), |
| (320) | 1-nor-2-hydroxymethyl-6-thiaprostaglandin E₁, |
| (321) | 1-nor-2-acetoxymethyl-6-thiaprostaglandin E₁, |
| (322) | 1-nor-2-methoxymethyl-6-thiaprostaglandin E₁, |
| (323) | 11,15-bis(t-butyldimethylsilyl)ether of (305), |
| (324) | 11,15-bis(2-tetrahydropyranyl)ether of (305), |

-continued

| | |
|---|---|
| (325) | 11,15-bis(t-butyldimethylsilyl)ether of (306), |
| (326) | 11,15-bis(t-butyldimethylsilyl)ether of (307), |
| (327) | 11,15-bis(t-butyldimethylsilyl)ether of (308), |
| (328) | 11,15-bis(t-butyldimethylsilyl)ether of (309), |
| (329) | 11,15-bis(t-butyldimethylsilyl)ether of (316), |
| (330) | 11,15-bis(t-butyldimethylsilyl)ether of (317), and |
| (331) | 11,15-bis(t-butyldimethylsilyl)ether of (300), |

Compounds of formula (I) in which only A at the

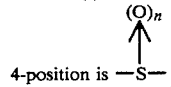

4-position is —S—

| | |
|---|---|
| (400) | 4-Thiaprostaglandin $E_1$, |
| (401) | 20-methyl-4-thiaprostaglandin $E_1$, |
| (402) | 17,20-dimethyl-4-thiaprostaglandin $E_1$, |
| (403) | 16,17,18,20-pentanor-15-cyclohexyl-4-thiaprostaglandin $E_1$, |
| (404) | 15-methyl-4-thiaprostaglandin $E_1$, |
| (405) | methyl ester of (400), |
| (406) | ethyl ester of (400), |
| (407) | n-nonyl ester of (400), |
| (408) | α-phenethyl ester of (400), |
| (409) | p-methoxyphenyl ester of (400), |
| (410) | methyl ester of (401), |
| (411) | methyl ester of (402), |
| (412) | p-trifluoromethylphenyl ester of (402), |
| (413) | methyl ester of (403), |
| (414) | p-methoxycarbonylphenyl ester of (403), |
| (415) | methyl ester of (404), |
| (416) | ethyl ester of (404), |
| (417) | sodium salt of (400), |
| (418) | calcium salt of (401), |
| (419) | aluminum salt of (402), |
| (420) | magnesium salt of (403), |
| (421) | phenethylammonium salt of (404), |
| (422) | S—oxide of (405), |
| (423) | S—oxide of (411), |
| (424) | S—dioxide of (405), |
| (425) | N,N—dimethylamide of (400), |
| (426) | N—cyclohexyl-N—methylamide of (402), |
| (427) | amide of (403), |
| (428) | 1-nor-2-acetoxymethyl-4-thiaprostaglandin $E_1$, |
| (429) | 1-nor-2-ethoxymethyl-4-thiaprostaglandin $E_1$, |
| (430) | 11,15-bis(t-butyldimethylsilyl)ether of (405), |
| (431) | 11,15-bis(2-tetrahydropyranyl)ether of (405), |
| (432) | 11,15-bis(t-butyldimethylsilyl)ether of (422), |
| (433) | 11,15 bis(t-butyldimethylsilyl)ether of (424), |
| (434) | 11,15-bis(t-butyldimethylsilyl)ether of (425), |
| (435) | 11,15-bis(t-butyldimethylsilyl)ether of (426), |
| (436) | 11,15-bis(t-butyldimethylsilyl)ether of (427), |
| (437) | 11,15-bis(t-butyldimethylsilyl)ether of (428), |
| (438) | 11-(6,6-dimethyl-3-oxa-2-oxo-bicyclo[3.1.0]hex-4-yl-15-t-butyldimethylsilyl ether of (405), |
| (439) | 2-methyl-4-thiaprostaglandin $E_1$, |
| (440) | methyl ester of (439), |
| (441) | 11,15-bis(t-butyldimethylsilyl)ether of (440), |
| (442) | 2,2-dimethyl-4-thiaprostaglandin $E_1$, |
| (443) | methyl ester of (442), |
| (444) | 2,2-difluoro-4-thiaprostaglandin $E_1$, and |
| (445) | methyl ester of (444), |

All of the above-exemplified compounds are natural-type prostaglandin $E_1$ derivatives. The corresponding 15-epimers of these prostaglandin $E_1$ derivatives and the corresponding enantiomers of these may also be cited as examples.

The 7-thiaprostaglandin $E_1$ derivatives of the following formula (I)-a

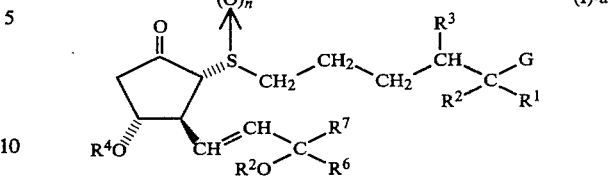

wherein all symbols are as defined with regard to formula (I), their 15-epimers, the enantiomers of these derivatives and their 15-epimers, and mixtures of these are produced in accordance with this invention by reacting a 2-organothio- 2-cyclopentenone of formula (II)

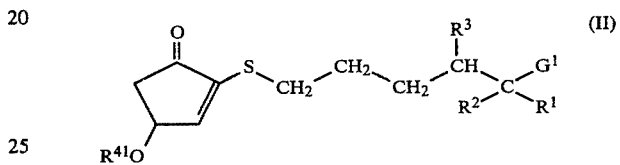

wherein $R^1$, $R^2$ and $R^3$ are as defined with regard to formula (I); $G^1$ represents —COOR$^{81}$, —CONR$^{91}$R$^{101}$, or CH$_2$OR$^{111}$ in which $R^{81}$ represents a $C_1$–$C_{10}$ alkyl group, a substituted or unsubstituted phenyl group, a substituted or unsubstituted alicyclic group, or a substituted or unsubstituted phenyl ($C_1$–$C_2$) alkyl group, $R^{91}$ and $R^{101}$ are identical or different and each represents a $C_1$–$C_{10}$ alkyl group, a substituted or unsubstituted $C_5$–$C_6$ alicyclic group, a substituted or unsubstituted phenyl group, or a substituted or unsubstituted phenyl ($C_1$–$C_2$) alkly group, or $R^{91}$ and $R^{101}$, taken together with the nitrogen atom to which they are bonded, may form a substituted or unsubstituted 5- or 6-membered ring which may further contain a hetero atom, and $R^{111}$ represents a $C_1$–$C_6$ alkyl group, a substituted or unsubstituted $C_1$–$C_7$ acyl group, a tri($C_1$–$C_6$)hydrocarbonsilyl group, or a group forming an acetal linkage together with the oxygen atom of the hydroxyl group; and $R^{41}$ represents tri($C_1$–$C_6$)hydrocarbon-silyl group or a group forming an acetal linkage together with the oxygen atom of the hydroxyl group; with an organic copper-lithium compound of formula (III)

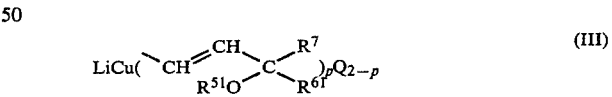

wherein $R^7$ is as defined with regard to formula (I), $R^{51}$ represents a tri($C_1$–$C_6$)hydrocarbon-silyl group or a group forming an acetal linkage together with the oxygen atom of the hydroxyl group, $R^{61}$ represents a hydrogen atom, a methyl group or a protected ethynyl group, Q represents a halogen atom, a $C_1$–$C_6$ alkoxy group, a phenoxy group, a phenylthio group, a di(C$_1$–C$_6$)alkylamino group, a $C_1$–$C_5$ alkyl-substituted ethynyl group or a cyano group, and p is 1 or 2, in the presence of an aprotic inert organic solvent to effect conjugation addition reaction; then as required, removing $R^{81}$, NR$^{91}$R$^{101}$ or $R^{111}$ and at least one group selected from $R^{41}$ and $R_{51}$ from the reaction product; as required, subjecting the reaction product having a carboxyl group to salt-forming reaction or amidation reaction; and further, as required, converting these reaction products to sulfoxides or sulfones.

The 2-organothio-2-cyclopentanones of formula (II) are compounds which do not contain active hydrogen atom as is seen from the definitions of $R^1$, $R^2$, $R^3$, $R^{41}$ and $G^1$ in formula (II). The definitions of $R^{41}$ and $G^1$ in formula (II) differ from the definitions of $R^4$ and G in formula (I) only in that formula (II) show compounds free of active hydrogen. Specific examples of $R^1$, $R^2$, $R^3$, $R^{41}$ and $G^1$ in general formula (II) are therefore evident from the foregoing description.

When $R^1$ and $R^3$ in formula (II) do not form a bond, the 2-organothio-2-cyclopentenone of formula (II) can be produced in accordance with the process described in U.S. Pat. No. 4,180,672 by reacting hydroxyprotected 4-hydroxy-2,3-epoxycyclopentanone (obtained by oxidizing a hydroxyl protected 4-hydroxy-2-cyclopentenone) with a corresponding thiol in the presence of a basic compound.

When $R^1$ and $R^3$ form a bond, the 2-organothio-2-cyclopentenones of formula (II) can be produced by reacting 4-hydroxy-2,3-epoxycyclopentanone with 4-mercaptobutan- 1- ol in the presence of a basic compound, then oxidizing the product to an aldehyde, and then introducing the corresponding $C_2$-moiety by the Witting reaction.

The disclosure of the U.S. Pat. No. 4,180,672 in regard to the process for producing 2-organothio-2- cyclopentenones is hereby cited as reference.

Examples of the 2-organothio-2-cyclopentenones of formula (II) used in this invention include the following.
4(RS)t-butyldimethylsilyloxy-2-(6-methoxycarbonylhexylthio)- 2-cyclopentenone,
4(R)-t-butyldimethylsilyloxy-2-(6-methoxycarbonylhexylthio)-2-cyclopentenone,
4(S)-t-butyldimethylsilyloxy-2-(6-ethoxycarbonylhexylthio)-2-cyclopentenone,
4(RS)-trimethylsilyloxy-2-(6-phenoxycarbonylhexylthio)-2-cyclopentenone,
4(RS)-(2-tetrahydropyranyloxy)-2-(6-benzyloxycarbonylhexylthio)-2-cyclopentenone,
4(RS)-t-butyldimethylsilyloxy-2-(6-methoxycarbonyl-5-methylhexylthio)-2-cyclopentenone,
4(RS)-t-butyldimethylsilyloxy-2-(6-methoxycarbonyl-5,5-dimethylhexylthio)-2-cyclopentenone,
4(RS)-t-butyldimethylsilyloxy-2-(6-methoxycarbonyl-5,5-difluorohexylthio)-2-cyclopentenone,
4(RS)-t-butyldimethylsilyloxy-2-(6-methoxycarbonyl-4-hexenylthio)-2-cyclopentenone,
4(RS)-t-butyldimethylsilyloxy-2-(6-morpholinocarbonylhexylthio)-2-cyclopentenone,
4(RS)-t-butyldimethylsilyloxy-2-(6-acetoxyhexylthio)-2-cyclopentenone, and
4(RS)-t-butyldimethylsilyloxy-2(6-trimethylsiloxyhexylthio)-2-cyclopentenone.

In general formula (III) representing the organic copper-lithium compound used as the other starting material in the process of this invention, $R^7$ is defined with regard to formula (I). $R^{51}$ is a tri($C_1$–$C_6$)hydrocarbonsilyl group or a group forming an acetal linkage together with the oxygen atom of the hydroxyl group. Specific examples of $R^7$ and $R^{51}$ are evident from the foregoing description. $R^{61}$ represents a hydrogen atom, or a methyl group, or a protected ethynyl group such as trimethylsilylethynyl or t-butyldimethylsilyl ethynyl. Q represents a halogen atom such as chlorine, bormine or iodine; a $C_1$–$C_6$ alkoxy group such as methoxy, ethoxy, n-propoxy, isopropoxy, n-butoxy n-pentoxy, or n-hexoxy; a phenoxy group; a phenylthio group; a ($C_1$–$C_6$)alkylamino group such as dimethylamino, diethylamino or dihexylamino; a $C_1$–$C_5$ alkylsubstituted ethynyl group such as methylethinyl, propylethynyl, t-butylethynyl or pentylethynyl; or a cyano group. p in formula (III) is 1 or 2.

Examples of the organic copper-lithium compound of formula (III) are as follows:

| $R^{51}$ | $R^{61}$ | $R^7$ | p | Q |
|---|---|---|---|---|
| t-butyldimethylsilyl | H | n-pentyl | 2 | — |
| " | " | " | 1 | phenylthio |
| " | " | " | " | propylethynyl |
| " | " | " | " | I |
| " | methyl | " | " | phenylthio |
| " | H | cyclohexyl | " | " |
| tetrahydropyranyl | " | " | " | " |
| " | " | n-hexyl | " | " |
| t-butyldimethylsilyl | " | 2-methylhexyl | " | I |
| " | " | 2-hexyl | " | t-butoxy |
| " | " | 2-methylheptyl | " | cyano |
| " | trimethylsilyl | n-pentyl | 1 | phenylthio |

The above organic copper-lithium compounds can be produced by reacting the corresponding organolithium compounds with a cuprous salt [see, for example, Organic Reaction, vol. 19, 1 (1972) ].

The addition reaction between the 2-organothio-2-cyclopentenone of formula (II) and the organic cooper-lithium compound of formula (III) is carried out in the presence of an aprotic inert organic solvent.

Stoichiometrically, the 2-organothio-2-cyclopentenone and the organic copper-lithium compound react in equimolar proportions. Usually, the organic copper-lithium compound is used in an amount of 0.5 to 5.0 moles, preferably 0.8 to 2.0 moles, per mole of the 2-organothio-2cyclopentenone.

The aprotic inert organic solvent used in the invention is liquid at the reaction temperature and does not react with the reagents. Examples include saturated aliphatic hydrocarbons such as pentane, hexane, heptane and cyclohexane; aromatic hydrocarbons such as benzene, toluene and xylene; aprotic ethers such as diethyl ether, tetrahydrofuran, dioxane, dimethoxyethane and diethylene glycol dimethyl ether; and other aprotic polar solvents such as hexamethylphosphoric triamide, N,N-dimethyl formamide, N,N-dimethylacetamide, dimethyl sulfoxide, sulfolane, and N-methylpyrrolidone. They may be used as a mixture of two or more. The aprotic inert organic solvent used in the production of the organic copper-lithium compound can directly be used as the aprotic inert organic solvent for the above reaction between the compounds (II) and (III). In this case, the 2-organo-2-cyclopentenone is added to the reaction mixture obtained by the reaction of forming the organic copper-lithium compound, and then the reaction is carried out. The amount of the aprotic inert organic solvent is that sufficient to cause the reaction to proceed smoothly. Usually, it is 1 to 100 times, preferably 2 to 20 times, the weight of the starting material.

The reaction temperature is generally from −100 to −20° C., preferably from −78° C. to −30° C. The reaction time varies depending upon the reaction temperature, and usually it is sufficient to perform the reaction for about 1 hour at a temperature of −100° C. to −20° C.

Desirably, the reaction is carried out in an atmosphere of an inert gas such as nitrogen or argon.

Preferably, the reaction is carried out in the presence of a trivalent phosphorus compound. The divalent phosphorus compound serves to dissolve the organic copper-lithium compound uniformly in the aprotic inert organic solvent and to cuse the reaction to proceed smoothly. Hence, the trivalent phosphorus compound may also be caused to be present during the preparation of the organic copper-lithium compound, and the 2-organothio-2-cyclopentenone may be added to the reaction mixture of the organocopper organic copper-lithium compound to carry out the reaction there.

Exemplary of the trivalent phosphorus compound are tri($C_1$–$C_6$) alkylphosphines such as trimethylphosphine, triethylphosphine, tri-n-butylphosphine and tri-n-hexylphosphine; tri($C_1$–$C_6$)alkyl phosphites such as trimethyl phosphites, triethyl phosphites, isopropyl phosphite, tri-n-butyl phosphite and tri-n-hexyl phosphite; and hexamethylphosphorus triamide.

The conjugation addition reaction in accordance with this invention gives 7-thiaprostaglandin $E_1$ derivatives of the following formula (I)-a'

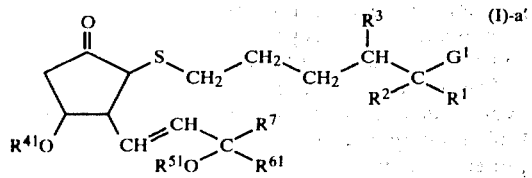

wherein $R^1$, $R^2$, $R^3$, $R^{41}$, $R^{51}$, $R^{61}$, $R^7$ and $G^1$ are as defined hereinabove. A group of the compounds of formula (I)-a' form part of a group of the compounds of formula (I)-a above. The compounds of formula (I)-a' correspond to those of formula (I)-a in which n is O and the hydroxyl group and the carboxyl group is protected.

Accordingly, the present invention can give compounds of formula (I)-a in which at least one of the hydroxyl and carboxyl groups is free as a result of removing a protected group, i.e. either one of $R^{81}$, the dibenzopiperidyl group, or $R^{111}$ and at least one protective group selected from the class consisting of $R^{41}$ and $R^{51}$.

The deprotection reaction may be carried out in the reaction mixture formed at the end of the conjugation addition reaction. Or it may be carried out after isolating the product of formula (I)-a' from the reaction mixture of the aforesaid conjugation addition reaction.

When the protective group for the hydroxyl group is a group forming an acetal linkage together with the oxygen atom of the hydroxyl group, the deprotection is conveniently carried out by using acetic acid, p-toluenesulfonic acid, a pyridinium salt of p-toluenesulfonate or a cation exchange resin as a catalyst and water, tetrahydrofuran, ethyl ether, dioxane, methanol, ethanol, acetone acetonile or the like as a reaction solvent. The reaction is carried out usually at a temperature of −78° C. to +100° C. for a period of from 10 minutes to about 3 days. When the protective group is a tri($C_1$–$C_6$)hydrocarbon-silyl group, the reaction may be carried out at the same temperature for the same period of reaction by using acetic acid, hydrofluoric acid, tetrabutyl ammonium fluoride, cesium fluoride, etc. as the catalyst.

Removal of the protective group for the carboxyl group, when the carboxyl group is in the form of an ester, may be carried out by using an enzyme such as lipase at a temperature of −10° C. to +100° C. for 10 minutes to about 24 hours in the reaction solvent exemplified hereinabove. When the carboxyl group is protected as a dibenzopiperidylamide group, it can be very easily removed by reacting it with an oxidizing agent such as cerium ammonium nitrate [Ce(NO$_3$)$_4$.2NH$_4$NO$_3$.xH$_2$O] in the presence of water in a solvent such as acetonitrile, tetrahydrofuran or benzene at a temperature of 0° C. to 50° C. for 1 minute to 3 hours.

According to the process of this invention, the compound having a carboxyl group resulting from the deprotection reaction is then subjected, as required, to salt-forming reaction or amidation reaction to give the corresponding carboxylic acid salt or amide.

The salt-forming reaction is known per se, and can be performed by neutralizing the compound with a basic compound such as sodium hydroxide, potassium hydroxide, sodium carbonate, ammonia, trimethylamine, monoethanolamine, or morpholine in a customary manner, the amount of the basic compound being substantially equimolar to the carboxylic acid. The amidation reaction is also known per se, and is carried out by reacting the carboxylic acid with a corresponding amine in the presence of a condensing agent such as dicyclocarbodiimide or a combination of isobutyl chloroformate and triethylamine.

The resulting compound in which —S— exists at the 7-position may then be converted to a sulfoxide or sulfone. The conversion reaction is carried out preferably in an inert solvent in the presence of an oxidizing agent.

In the production of the sulfoxide, the oxidizing agent preferably includes, for example, hydrogen peroxide, peracids such as peracetic acid, perbenzoic acid and m-chloroperbenzoic acid, sodiium meta-periodate, hydroperoxide, selenium dioxide, chromic acid, iodosylbenzene, hypochloric acid, and t-butyl hydroperoxide. In the production of the sulfone, preferred oxidizing agents are, for example, hydrogen peroxide, a combination of hydrogen peroxide and tungsten or vanadium catalyst, peracetic acid, perbenzoic acid, m-chloroperbenzoic acid, ruthenium oxide and osmium oxide [VIII]. Preferred examples of the inert organic solvent are acetic acid, methylene chloride, chloroform, 1,2-dichloroethane, benzene and ethyl acetate.

The reaction temperature is preferably in the range of −78° C. to 50° C., especially preferably −20° C. to 30° C. The reaction time varies depending upon the types of the starting compounds, the reaction temperature and the type of the oxidizing agent. Usually, it is from 30 minutes to 48 hours.

When it is desired to produce the sulfoxide by using an oxidizing agent which is conducive to the formation of both sulfoxides and sulfones, it is preferred to adjust the amount of the oxidizing agent to one insufficient to give the sulfone, for example about 1 to about 1.5 equivalents based on the 7S-compound, and to monitor the reaction by TLC, etc.

The conjugation addition reaction in accordance with this invention proceeds stereospecifically. This means that the configuration of the substituent —OR$^{41}$ at the 4-position of the 2-organothio-2-cyclopentenone of formula (II) determines the direction in which the organic group

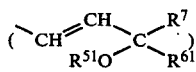

from the organic copper-lithium compound of formula (III) is introduced into the skeleton of the cyclopentenone.

Accordingly, when

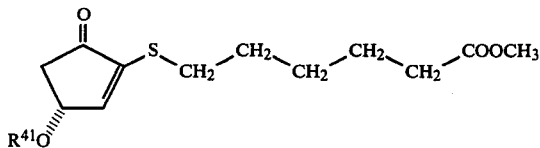

and

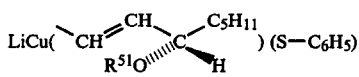

are subjected to conjugation addition reaction, only a natural-type 7-thiaprostaglandin $E_1$ derivative of the following formula $(I_1)$ is formed.

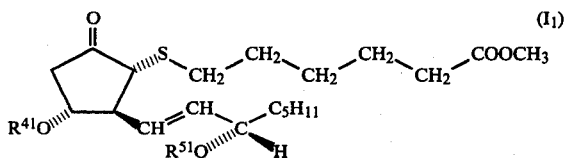

Similarly, when a compound of the following formula

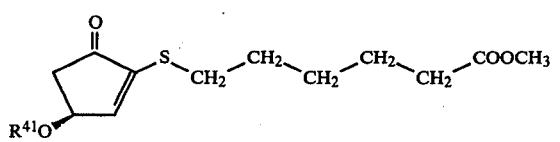

and the same organic copper-lithium compound as above are subjected to conjugation addition reaction, a 15-epi enantiomer (diastereomer) alone of the above natural-type 7-thiaprostaglandin $E_1$ derivative which is expressed by the following formula $(I_1)'$ent results.

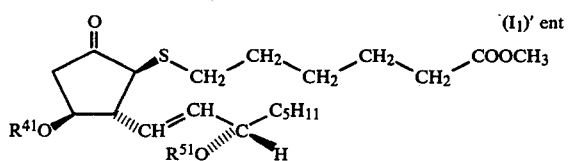

It will be understood from the above reaction that if a compound of the following formula

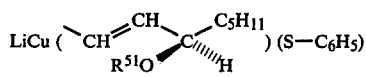

is used as the organic copper-lithium compound in the above two reactions, there will be formed only the 15-epimer $(I_1)'$ and enantiomer [$(I_1)$ent having reverse configurations of the 8-, 11-, 12- and 15-positions to the natural-type] of the natural type 7-thiaprostaglandin $E_1$ derivative.

When a compound of the following formula

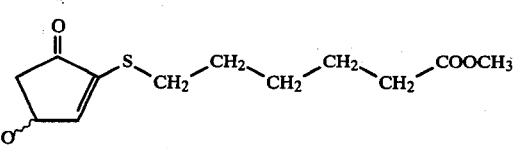

wherein ~ means a mixed bond of ııııı and —, and

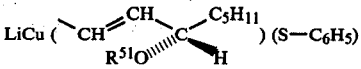

are subjected to conjugation addition reaction, a mixture of the compounds of formula $(I_1)$ and $(I_1)'$ent is formed. These two diastereomers can be separated from each other by, for example, removing the protective groups ($R^{41}$ and $R^{51}$) for the hydroxyl group, and then subjecting the resulting product to TLC, etc.

It will be understood from the above reaction that if a compound of the following formula

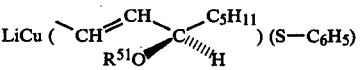

is used instead of the above organic copper-lithium compound, a mixture of the compounds of formula $(I_1)'$ and $(I)$ent is formed. This mixture can similarly be separated into the individual diastereomers.

When a compound of the following formula

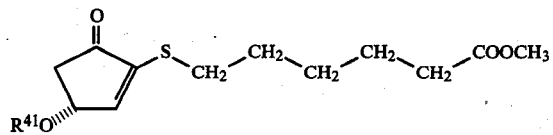

and a compound of the following formula

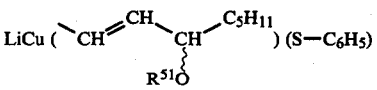

are subjected to conjugation addition reaction, an epimeric mixture of $(I_1)$ and $(I_1)'$ is formed. It will be also understood that if a compound of the following formula

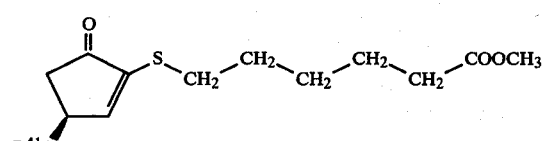

is used instead of the aforesaid 2-organothio-2-cyclopentenone, an epimeric mixture of $(I_1)$ent and $(I_1)'$ent is formed. These epimeric mixtures can also be separated into the individual epimers by TLC, etc.

The compound selected from the group consisting of 6-thiapsostaglandin $E_1$ derivatives of the following formula (I)-b

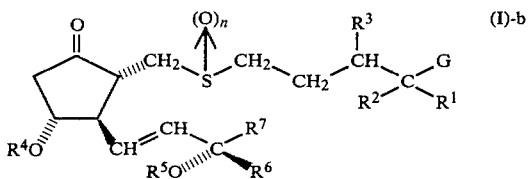  (I)-b wherein all symbols are as defined with regard to formula (I), their 15-epimers, the enantiomers of the derivatives and their 15-epimers, and the mixtures of these can be produced in accordance with this invention by subjecting an $\alpha,\beta$-unsaturated ketone of formula (IV)

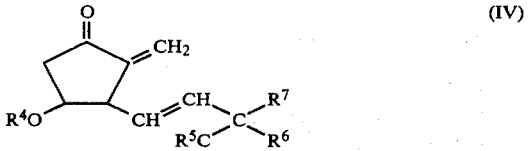  (IV)

wherein all symbols are as defined with regard to formula (I), and a thiol compound of formula (V)

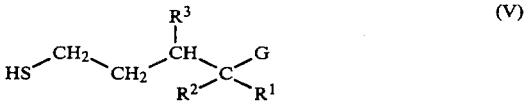  (V)

wherein all symbols are as defined with regard to formula (I), to the Michael addition reaction in the presence of a basic compound; then as required, removing $R^8$ or $R^{11}$ and at least one group selected from $R^4$ and $R^5$ from the resulting compound in which each of said group is other than a hydrogen atom; then as required, subjecting the reaction product having a carboxyl group to salt-forming reaction; further as required, subjecting the reaction product having a carboxyl group to amidation reaction; and as required, converting these reaction products to sulfoxides or sulfones.

Specific examples of the group represented by $R^4$, $R^5$, $R^6$ and $R^7$ in formula (IV) are evident from the foregoing description.

The $\alpha,\beta$-unsaturated ketone of formula (IV) can be produced by the method described in G. Stork et al., J. Amer. Chem. Soc., 97, 4745, 6260, (1975) or Japanese Laid-Open Patent Publication No. 153725/1980.

Specifically, it can be produced by reacting a cyclopentanone of the following formula

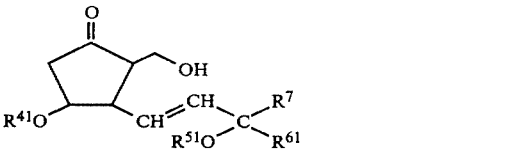

wherein $R^{41}$, $R^{51}$, $R^{61}$ and $R^7$ are as defined above, with an organic sulfonyl chloride of the formula

RSO$_2$CL wherein R represents a lower alkyl group, preferably a methyl group, a polyhalogenated lower alkyl group, preferably a trifluoromethyl group, or a substituted phenyl group, preferably a p-tolyl or p-bromophenyl group, in the presence of a basic organic compound to form a sulfonate of the following formula

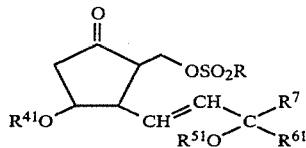

wherein R, $R^{41}$, $R^{51}$, $R^{61}$ and $R^7$ are as defined above, and thereafter heating the resulting sulfonate to a temperature of, for example, about 0° to about 50° C. to split off the organic sulfonic acid.

The reaction of forming the sulfonate and the reaction of splitting off the organic sulonic acid can be carried out in the same reaction system.

The above reaction can give an $\alpha,\beta$-unsaturated ketone of formula (IV) in which $R^4$, $R^5$ and $R^6$ are $R^{41}$, $R^{51}$ and $R^{61}$, respectively. $\alpha,\beta$-Unsaturated ketones of formula (IV) in which $R^4$ and $R^5$ are hydrogen atoms and $R^6$ is an ethynyl group can be produced by removing the protective groups $R^{41}$ and $R^{51}$ from the $\alpha,\beta$-unsaturated ketone obtained by the above reaction or by converting the protected ethynyl group ($R^{61}$) into an ethynyl group.

Some of the $\alpha,\beta$-unsaturated ketones obtained by the above reaction are novel compounds. Examples of the $\alpha,\beta$-unsaturated ketone of formula (IV) are:

4(RS)-hydroxy-3(RS)-[3(S)-hydroxy-1-transoctenyl]-2-methylidene-cyclopentanone,

4(RS)-t-butyldimethylsilyloxy-3(RS)-[3(S)-(t-butyldimethylsilyloxy)-1-trans-octenyl]-2-methylidenecyclopentanone, 4(R)-t-butyldimethylsilyloxy-3(R)-[3(S)-(t-butyldimethylsilyloxy)-1-trans-octenyl]-2-methylidene-cyclopentanone, 4(S)-t-butyldimethylsilyloxy-3(S)-[3(S)-(t-butyldimethylsiloxy)-1-trans-octenyl]-2-methylidene-cyclopentanone, 4(R)-tetrahydropyranyloxy-3(R)-[3(S)-(tetrahydropyranyloxy)-1-trans-octenyl]-2-methylidene-cyclopentanone, 4(R)-t-butyldimethylsilyloxy-2(R)-[3(S)-(t-butyldimethylsilyloxy)-1-trans-nonenyl]-2-methylidene-cyclopentanone, 4(RS)-t-butyldimethylsilyloxy-3(RS)-[3(S)-(t-butyldimethylsilyloxy)-5-methyl-1-trans-nonenyl]-2-methylidene-cyclopentanone, 4(R)-t-butyldimethylsilyloxy-3(R)-[3(S)-(t-butyldimethylsiloxy)-3(S)-cyclohexyl-1-trans-propenyl]-2-methylidene-cyclopentanone, and 4(RS)-t-butyldimethylsilyloxy-3(RS)-[3(RS)-(t-butyldimethylsilyloxy)-3(RS)-methyl-1-trans-octenyl]-2-methylidene-cyclopentanone.

The thiol compound, the other starting material used in the above process, is expressed by formula (V).

The definitions of $R^1$, $R^2$, $R^3$ and G in formula (V) are as given in the above formula.

The thiol compounds of formula (V) are known compounds, and examples include the following compounds.

5-Mercaptovaleric acid,
methyl 5-mercaptovalerate,
ethyl 5-mercaptovalerate,
hexyl 5-mercaptovalerate,
decyl 5-mercaptovalerate, phenyl 5-mercaptovalerate,
benzyl 5-mercaptovalerate,
5-hydroxy-1-pentanethiol,
5-acetoxy-1-pentanethiol,
5-benzoyloxy-1-pentanethiol,
5-methoxy-1-pentanethiol,
5-mercaptovaleric acid morpholide,
methyl 5-mercapto-2-methylvalerate, and
methyl 5-mercapto-2,2-dimethylvalerate.

The Michael reaction between the compound of formula (IV) and the compound of formula (V) is carried out in the presence of a basic compound.

The basic compound used may be a nitrogen-containing organic base, an alkali metal alkoxide or an alkali metal-containing inorganic base.

Examples of suitable nitrogen-containing organic bases are primary amines such as methylamine, ethylamine, butylamine, isopropylamine, and benzylamine; secondary amines such as diethylamine, diisopropylamine and methylethylamine; tertiary amines such as triethylamine, tributylamine and diisopropylethylamine; aromatic amines such as pyridine, p-dimethylaminopyridine, 2,6-lutidine, imidazole and quinoline; and nitrogen-containing heterocyclic bases such as pyrrolidine, piperidine, N-ethylpiperidine, morpholine, N-ethylmorpholine, 1,5-diazabicyclo[4.3.0]non-5-ene, 1,5-diazabicyclo[5.4.0]undec-5-ene, and 1,4-diazabicyclo[2.2.2]octane.

Examples of suitable alkali metal-containing inorganic bases include alkali metal hydroxides such as sodium hydroxide and potassium hydroxide, and alkali metal carbonate such as sodium carbonate and potassium carbonate.

Examples of suitable alkali metal alkoxides are sodium methoxide, sodium ethoxide and potassium t-butoxide.

Stoichiometrically, the $\alpha,\beta$-unsaturated ketone of formula (IV) and the thiol compound of formula (V) react in equimolar proportions. Usually, 0.8 to 10 moles, preferably 1 to 3 moles, of the thiol compound (V) is used per mole of the $\alpha,\beta$-unsaturated ketone (IV).

Preferably, the reaction is carried out in the presence of an inert organic solvent, for example an ether such as ethyl ether, tetrahydrofuran, dioxane and dimethoxyethane, a halogenated hydrocarbon such as chloroform, carbon tetrachloride and dichloromethane an aromatic hydrocarbon such as benzene and toluene, or an alcohol such as methanol, ethanol and isopropanol.

The reaction temperature is from $-30°$ C. to $50°$ C., preferably from $-10°$ C. to $20°$ C. The reaction time is usually from 10 minutes to 30 hours, preferably from 30 minutes to 10 hours.

The reaction is carried out preferably in an atmosphere of an inert gas such as nitrogen and argon.

The Michael reaction can also be performed in the same reaction system as the system of the reaction of forming the $\alpha,\beta$-unsaturated ketone of formula (IV) (the reaction of forming the sulfonate or the reaction of liberating the organic sulfonic acid).

The aforesaid Michael reaction gives 6-thiaprostaglandin $E_1$ derivatives of formula (I)-b'

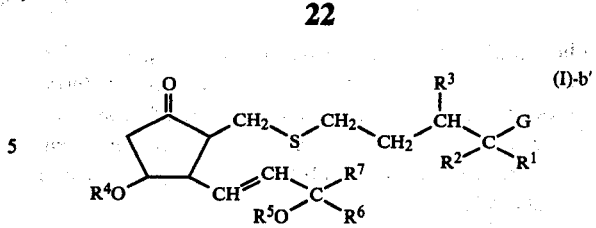

wherein all symbols are as defined hereinabove.

A group of the compounds of formula (I)-b' constitute a group of compounds of formula (I)-b in which n is zero.

When the compounds of formula (I)-b are those in which $R^8$ or $R^{11}$ and at least one member selected from $R^4$ and $R^5$ are other than hydrogen, it is possible according to the process of this invention to remove such groups from these compounds. This results in the production of 6-thiaprostaglandin $E_1$ derivatives in which the carboxyl group or the hydroxyl group is free. The removing reaction can be carried out in the same way as in the aforesaid reaction of removing protective groups from the compounds of formula (I)-a'.

According to the process of this invention, compounds of formula (I)-b having a free carboxyl group obtained by the Michael reaction or the reaction of removing the protective groups can then be subjected to salt-forming reaction or amidation reaction to convert them into their salts or amides. The salt-forming reaction and the amidation reaction can be carried out under the same conditions as described hereinabove.

According to the process of this invention, the resulting compounds having —S— at the 6-position may, as required, be converted to their sulfoxides or sulfones under the same reaction conditions as described hereinabove.

The present invention according to the aforesaid Michael reaction gives thermodynamically stable compounds of formula (I)-b' having a substituent of the formula

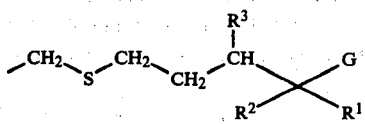

at the 2-position which is trans to the substituent

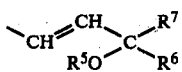

at the 3-position of the $\alpha,\beta$-unsaturated ketone of formula (IV).

The compound selected from the group consisting of 4-thiaprostaglandin $E_1$ derivatives of formula (I)-c

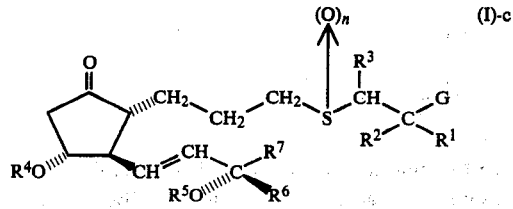

wherein all symbols are as defined with regard to formula (I), their 15-epimers, the enantiomers of said derivatives and their 15-epimers, and mixtures of these compounds can be produced in accordance with this invention by reacting a 2-allyl-substituted cyclopentanone of formula (VI)

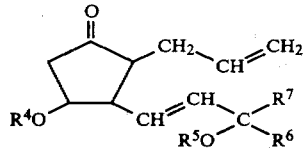
(VI)

wherein all symbols are as defined with regard to formula (I), with a thiol compound of formula (VII)

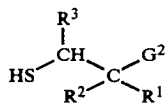
(VII)

wherein $R^1$, $R^2$ and $R^3$ are as defined with regard to formula (I); and $G^2$ is —COOR$^{82}$, —CONR$^9$R$^{10}$, or —CH$_2$OR$^{11}$ in which R$^{82}$ represents a hydrogen atom, a $C_1$–$C_{10}$ alkyl group, a substituted or unsubstituted phenyl group, a substituted or unsubstituted alicyclic group, or a substituted or unsubstituted phenyl ($C_1$–$C_2$) alkyl group and $R^9$, $R^{10}$ and $R^{11}$ are as defined above, in the presence of a radical generator and/or under ultraviolet irradiation; then as required, when the reaction product is a compound in which R$^{82}$ or R$^{11}$, and at least one member selected from R$^4$ and R$^5$ are groups other than hydrogen, removing said groups other than hydrogen from said product; then as required, subjecting the reaction product having a carboxyl group to salt-forming reaction; as further required, subjecting the reaction product having a carboxyl group to amidation reaction; and as required, converting these reaction products to sulfoxides.

Specific examples of the groups $R^4$, $R^5$, $R^6$ and $R^7$ in formula (VI) are evident from the foregoing description.

The 2-allyl-substituted cyclopentanone of formula (VI) can be produced in accordance with the process described in Tetrahedron Letters, 1131 (1977) and Tetrahedron vol. 34, 2775 (1978).

Specifically, it can be produced by reacting furfural and an allyl magnesium halide such as allyl magnesium chloride in accordance with the Grignard reaction to form a compound of the following formula

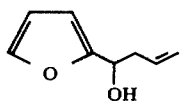

then treating the compound with a mineral acid such as phosphoric acid to form 5-allyl-4-hydroxy-2-cyclopentenone of the following formula

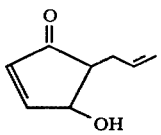

then treating the resulting compound with alumina to isomerize it to 2-allyl-4-hydroxy-2-cyclopentenone of the following formula

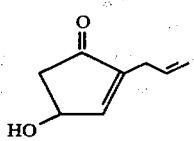

thereafter protecting the hydroxyl group of this compound, and subjecting the protected compound to conjugation addition reaction with the organic copper-lithium compound of formula (III) described hereinabove.

By the aforesaid series of reactions, there can be produced 2-allyl-substituted cyclopentanones of formula (VI) in which $R^4$, $R^5$ and $R^6$ are $R^{41}$, $R^{51}$ and $R^{61}$, respectively.

2-Allyl-substituted cyclopentanones of formula (VI) in which $R^4$ and $R^5$ are hydrogen atoms and $R^6$ is an ethynyl group can be produced by removing the protective groups $R^{41}$ and $R^{51}$ from the 2-allyl substituted cyclopentanones obtained by the above reaction or by converting the protected ethynyl group ($R^{61}$) into an ethynyl group.

Some of the 2-allyl substituted cyclopentanones obtained by the aforesaid series of reactions are novel compounds.

Examples of the 2-allyl substituted cyclopentanones of formula (VI) are;

4(RS)-hydroxy-3(RS)-[3(S)-hydroxy-1-trans-octenyl]-2(SR)-allyl-cyclopentanone,

4(RS)-t-butyldimethylsilyloxy-3(RS)-[3(S)-(t-butyldimethylsilyloxy)-1-trans-octenyl]-2(SR)-allyl-cyclopentanone, 4(R)-t-butyldimethylsilyloxy-3(R)-[3(S)-(t-butyldimethylsilyloxy)-1-trans-octenyl]-2(S)-allyl-cyclopentanone, 4(S)-t-butyldimethylsilyloxy-3(S)-[3(S)-(t-butyldimethylsilyloxy)-1-trans-octenyl]-2(R)-allyl-cyclopentanone, 4(R)-tetrahydropyranyloxy-3(R)-[3(S)-(tetrahydropyranyloxy)-1-trans-octenyl]-2(S)-allyl-cyclopentanone, 4(R)-t-butyldimethylsilyloxy-3(R)-[3(S)-(t-butyldimethylsilyloxy)-1-trans-nonenyl]-2(S)-allyl-cyclopentanone, 4(RS)-t-butyldimethylsiyloxy-3(RS)-[3(S)-(t-butyldimethylsilyloxy)-5-methyl-1-trans-nonenyl]-2(SR)-allyl-cyclopentanone 4(R)-t-butyldimethylsilyloxy-3(R)-[3(S)-(t-butyldimethylsilyloxy)-3(S)-cyclohexenyl-1-trans-propenyl]-2(S)-allyl-cyclopentanone, and 4(RS)-t-butyldimethylsilyloxy-3(RS)-[3(RS)-(t-butyldimethylsilyloxy)-3(RS)-methyl-1-trans-octenyl]-2(SR)-allyl-cyclopentanone.

The thiol compound, one starting material used in the process of this invention, is represented by formula (VII) in which all symbols are as defined hereinabove.

The thiol compounds of formula (VII) are known compounds. Examples of such thiol compounds include:

3-mercaptopropionic acid,
methyl 3-mercaptopropionate,
ethyl 3-mercaptopropionate,
hexyl 3-mercaptopropionate,
decyl 3-mercaptopropionate,
phenyl 3-mercaptopropionate,
benzyl 3-mercaptopropionate,
3-hydroxy-1-propanethiol,
3-acetoxy-1-propanethiol,
3-benzoyloxy-1-propanethiol,
3-methoxy-1-propanethiol,
3-mercaptopropionic acid morpholide,
methyl 3-mercapto-2-methylpropionate, and
methyl 3-mercapto-2,2-dimethylpropionate.

The reaction between the allyl-substituted cyclopentanone of formula (VI) and the thiol compound of formula (VII) is carried out in the presence of a radical generator, and/or under ultraviolet irradiation.

Exemplary of these radical generators are t-butyl hydroperoxide, di-t-butyl peroxide, cumene hydroperoxide, benzoyl peroxide, lauroyl peroxide and azobisisobutyronitrile.

Ultraviolet light used has a wavelength in the region of about 200 nm to about 400 nm.

Preferably, the reaction is carried out in the presence of an inert organic solvent. Examples of suitable inert organic solvents are ethers and aromatic hydrocarbons as in the process of the invention involving the Michael reaction described above, and aliphatic hydrocarbons such as pentane hexane, cyclohexane and ligron.

When the reaction is carried out in the presence of the radical generator, the reaction temperature is usually $-30°$ C. to $+200°$ C., preferably $0°$ C. to $100°$ C. When the reaction is carried out under ultraviolet irradiation, the reaction temperature is usually from $-100°$ C. to $+50°$ C., preferably from $-78°$ C. to $+30°$ C.

Stoichiometrically, the allyl-substituted cyclopentanone of formula (VI) and the thiol compound of formula (VII) is equimolar proportions. The thiol compound is used in an amount of usually about 0.9 to about 10 moles, preferably 1 to 3 moles, per mole of the allyl-substituted cyclopentanone.

The reaction is carried out conveniently in an atmosphere of an inert gas such as nitrogen and argon.

The above radical reaction gives 4-thiaprostaglandin $E_1$ derivatives of the following formula

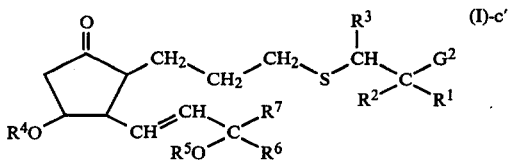

(I)-c′ wherein all symbols are as defined above.

A group of the compounds of formula (I)-c′ correspond to the compounds of formula (I)-c in which G is other than —COO—monovalent cation.

According to the process of this invention, compounds of formula (I)-c′ in which $R^{82}$ or $R^{11}$, and at least one member selected from $R^4$ and $R^5$ are groups other than hydrogen may be further treated to remove such groups other than hydrogen. This results in the production of 4-thiaprostaglandin $E_1$ derivatives in which the carboxyl group or the hydroxyl group is free.

Such removing reaction can be performed as described hereinabove.

According to the process of this invention, the compound having a free carboxyl group obtained by the above addition reaction with the thiol compound or the above reaction by removing the protective groups can then be subjected to salt-forming reaction or amidation reaction to form its salt or amide. The salt-forming reaction and the amidation reaction are as described hereinabove.

According to the process of this invention, the compounds having —S— at the 4-position prepared as above can be converted to their sulfoxides or sulfones under the same reaction conditions as described hereinabove.

Investigations of the present inventors have shown that those compounds of formula (I) provided by the invention which are represented by formula (I)-1 have especially superior pharmacological activities, for example an activity of controlling vascular actions.

Thus, the present invention provides a pharmaceutical composition for controlling vascular actions, comprising (1) as an active ingredient a compound selected from thiaprostaglandine $E_1$ derivatives of formula (I)-1

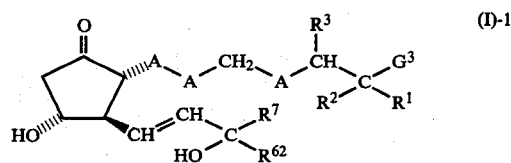

(I)-1 wherein $R^1$, $R^2$, $R^3$ and $R^7$ are as defined with regard to formula (I); A represents —CH$_2$— or —S— provided that only one A cut of three is —S—; $G^3$ represents —COOR$^8$, —CONH$_2$, or —CH$_2$OR$^{12}$ in which $R^8$ represents a hydrogen atom, a $C_1$–$C_{10}$ alkyl group, a substituted or unsubstituted phenyl group, a substituted or unsubstituted alicyclic group, a substituted or unsubstituted phenyl($C_1$–$C_2$) alkyl group, or one equivalent of a cation whose salt is pharmaceutically acceptable, and $R^{12}$ represents a hydrogen atom or a substituted or unsubstituted $C_2$–$C_7$ phenyl group; and $R^{62}$ represents a hydrogen atom, a methyl group or an ethynyl group, their 15-epimers, the enantiomers of said thiaprostaglandine $E_1$ derivatives and their 15-epimers [except the enantiomers of 6-thiaprostaglandins $E_1$ derivatives of formula (I)-1 or their 15-epimers], and mixtures of these compounds, and (2) a pharmaceutically acceptable carrier.

The pharmacological characteristic of the active compounds of formula (I)-1 is that not only do they have excellent activity of controlling vascular actions, but also their activity fully lasts even in oral administration and their side effects in administration are generally small.

The active compound in accordance with this invention can be administered orally, or parenterally (e.g., subcutaneously, intramuscularly, intravenously, etc.). Preferably, they are administered orally or intravenously. Oral administration is especially preferred.

The active compounds in accordance with this invention are administered either singly or as the aforesaid pharmaceutical composition or as a medicament in unit dosage form.

The amount of the active compound varies depending upon the type of the active compound, the subject to be treated, the condition, age, sex and body weight of the subject, the route of administration, etc. Usually, it can be administered in a dosage of about 0.2 μg to about 10 mg/kg of body weight/day. The dosage may be applied once or several times (for example, 2 to 5 times) a day.

The active compound of this invention can be administered to warm-blooded animals required to have their vascular actions controlled, for example to human beings and other animals. The active compound of this invention can be administered to warm-blooded animals required to have their vascular actions controlled for preventive or therapeutic purposes. The active compound of this invention can be administered to the subject against angina pectoris, myocardial infarction, thrombosis, arteriosclerosis and ulcers and for vasodilation, blood pressure lowering and platelet aggregating inhibition.

For oral administration, the pharmaceutical composition of this invention is conveniently formed into a solid or liquid preparation. Examples of the solid preparation are tablets, pills, powders or granules. In such solid preparations, at least one active compound is mixed with at least one pharmaceutically acceptable carrier such as sodium bicarbonate, calcium carbonate, potato starch, sucrose, mannitol and carboxymethyl cellulose. These preparations are produced in a customary manner. They may further include additives for formulation other than the carrier, for example lubricants such as calcium stearate, magnesium stearate and glycerol.

The liquid preparation for oral administration includes, for example, emulsions, solutions, suspensions, syrups and elixirs. These preparations include ordinary pharmaceutically acceptable carriers such as water or liquid paraffin.

The pharmaceutically acceptable carriers used in this invention may further include ordinary adjuvants such as wetting agents, suspending aids, sweetenings, flavors, aromas, stabilizers and antiseptics, as required.

These liquid preparations may be administered in capsular form using capsules made of absorbable materials such as gelatin.

The solid preparation for intrarectal administration includes a suppository which contains at least one active compound and prepared by a method known per se.

Preparations for parenteral administration are given as aseptic aqueous or nonaqueous solutions, suspensions or emulsions. Nonaqueous solutions or suspensions contain propylene glycol, polyethylene glycol, a vegetable oil such as olive oil, and an injectable organic ester such as ethyl oleate as the pharmaceutically acceptable carrier. These preparations may also contain adjuvants such as antiseptics, wetting agents, emulsifiers, dispersants and stabilizers. These solutions, suspensions and emulsions can be sterilized by filtration through a bacteria-holding filter, incorporation of a germicide, or irradiation. It is also possible to prepare an aseptic solid preparation, and dissolve it in aseptic water or an aseptic injectable solvent just prior to use.

The pharmaceutical composition and medicament in accordance with this invention may contain the active compound in the form of an inclusion compound with cyclodextrin, as is well known in the art.

The following Examples illustrate the present invention more specifically.

EXAMPLE 1

7-Thiaprostaglandin $E_1$ methyl ester (No. 124) and its 15-epi-enantiomer (15-epi-ent):

(1) 4(RS)-t-butyldimethylsilyloxy-2-cyclopentenone (2.12 g; 10 mmoles) was dissolved in 25 ml of methanol. The solution was cooled to 0° C., and 30% aqueous hydrogen peroxide (5 ml; 45 mmoles) was added. Several drops of a 2N aqueous solution of sodium hydroxide were added, and the mixture was stirred for 30 minutes. The methanol was distilled off under reduced pressure. Water was added to the residue and the mixture was extracted with ether. The extract was dried over magnesium sulfate, and concentrated under reduced pressure to give 4(RS)-t-butyldimethylsilyloxy-2,3-epoxycyclopentanone as a crude product. The crude product was dissolved in 20 ml of methanol, and a solution of 1.62 g (10 mmoles) of methyl 6-mercaptohexanoate in 10 ml of methanol was added. Furthermore 1 ml of triethylamine was added. The mixture was stirred at room temperature for 18 hours in an atmosphere of nitrogen. After the reaction, the reaction mixture was concentrated under reduced pressure. The residue was chromatographed on a silica gel column using hexane/ethyl acetate (6/1) as an eluent to give 2.24 g (6.02 mmoles; 60.2%) of 4(RS)-t-butyldimethylsilyloxy-2-(5-methoxycarbonylpentylthio)-2-cyclopentenone.

NMR (CDCl$_3$, δ (ppm)); 0.15 (6H, s, SiMl$_2$), 0.89 (9H, s, tBu), 1.4–1.8 (6H, m), 2.0–3.0 (6H, m), 3.61 (3H, s, COOCH$_3$), 4.90 (1H, m, C$_4$HOSi), 6.73 (1H, d, J=3 Hz, C$_3$-H).

IR (KBr, cm$^{-1}$): 1740, 1715

Mass (12 eV;m/e, %): 372 (M+, 2), 322 (16), 315 (27), 129 (60) 97 (68), 69 (100).

(2) A pentane solution (1.1 ml; 1.66 mmoles) of 1.5M t-butyllithium was added at −78° C. to an ether solution (3 ml) of 305 mg (0.828 mmole) of 3(S)-t-butyldimethylsilyloxy-1-iodo-trans-1-octene, and the mixture was stirred for 2 hours. To the solution was added a solution which was obtained by adding 163 mg (1.0 mmole) of hexamethylphosphorus triamide to a suspension of 86 mg (0.5 mmole) of phenylthiocopper (I) in 2 ml of ether and stirring the mixture at room temperature until the solution became homogeneous. The mixture was stirred at −78° C. for 1 hour. To the resulting solution was added a solution of 154 mg (0.414 mmoles) of 4(RS)-t-butyldimethylsilyloxy-2-(5-methoxycarbonylpentylthio)-2-cyclopentenone obtained as in (1) above in a mixture of 3 ml of ether, 1 ml of tetrahydrofuran, and 0.3 ml of hexamethylphosphoric triamide. The mixture was stirred at −78° C. for 15 minutes, at −40° C. for 1 hour and then at −20° C. for 1 hour. After the reaction, an ammonium chloride solution containing ammonia was added, and the aqueous layer was extracted twice with 100 ml of ether. The extracts were washed with an aqueous solution of ammonium chloride, dried over magnesium sulfate and concentrated to give 449 mg of a crude product. The crude product was subjected to preparative thin-layer chromatography (hexane/ethyl acetate=6/1) to give 156 mg (0.25 mmole, 61.4%) of a mixture of 11,15-bis(t-butyldimethylsilyl)-7-thiaprostaglandin E$_1$ methyl ester (No. 199) and its 15-epi-enantiomer.

NMR (CDCl$_3$, δ (ppm)): 0.07 (12H, s, SiMe$_2$), 0.87 (21H, s, tBu and terminal CH$_3$), 1.1–1.8 (14H, m), 2.1–3.0 (7H, m), 3.37 (1H, m C$_8$-H), 3.61 (3H, s, COOCH$_3$), -4.1 (2H, m, C$_{11}$-H and C$_{15}$-H), 5.43–5.65 (2H, m, olefin proton).

IR (liquid film, cm$^{-1}$): 1740, 1260, 1120, 965, 835, 775.

(3) 156 mg (0.254 mmole) of the bis-silyl ether obtained in (2) above was dissolved in a mixture of 3 ml of acetic acid, 1 ml of water, and 1 ml of tetrahydrofuran, and the solution was stirred at room temperature for 48 hours. Toluene (100 ml) was added, and the mixture was concentrated under reduced pressure to give 112 mg of a crude product. The crude product was subjected to preparative thin-layer chromatography (hexane/ethyl acetate=½) to give 14 mg (0.036 mmole, 14.3%) of 7-thiaprostaglandin E$_1$ methyl ester (No. 124) and 15 mg (0.039 mmole, 15.3%) of its 15-epi-enantiomer.

Compound No. 124

Thin-layer chromatography (hexane/ethyl acetate=½): Rf=0.35.

NMR (CDCl$_3$, δ (ppm)): 0.89 (3H, m, terminal CH$_3$), 1.1–1.8 (14H, m), 2.1–3.1 (10H, m), 3.61 (3H, s, COOCH$_3$), 3.90–4.25 (2H, m, C$_{11}$-H and C$_{15}$-H), 5.5–5.75 (2H, m, olefin proton).

IR (liquid film, cm$^{-1}$): 3400, 1735, 1255, 1200, 1165, 1125, 1075, 1010, 960.

Mass (20 eV; m/e, %): 386 (M$^+$, 2), 368 (27), 350 (16), 337 (7), 269 (28), 237 (74), 207 (59), 190 (78), 119 (91), 99 (100).

High resolution mass (70 eV): C$_{20}$H$_{34}$O$_5$S (M$^+$) calc. 386.2125, found 386.2142.

15-epi-enantiomer of compound No. 124

Thin-layer chromatography(hexane/ethyl acetate=½): Rf=0.40.

NMR (CDCl$_3$, δ (ppm)): 0.88 (3H, m, terminal CH$_3$), 1.1–1.8 (14H, m), 2.1–2.8 (10H, m), 3.64 (3H, s, COOCH$_3$), 3.85–4.25 (2H, m, C$_{11}$-H and C$_{15}$-H), 5.6–5.8 (2H, m, olefin proton).

NMR (liquid film cm$^{-1}$): 3420, 1740, 1260, 1205, 1175, 1130, 1080, 1010, 970.

Mass (20 eV; m/e, %): 386 (M$^+$, 3), 368 (25), 350 (12), 298 (17), 237 (29), 225 (40), 207 (72), 190 (40), 129 (48), 119 (50), 118 (50), 99 (100).

High resolution mass (70 eV): C$_{20}$H$_{34}$O$_5$S (M$^+$) calc. 386.2125; found 386.2118.

EXAMPLE 2

16,17,18,19,20-pentanor-15-cyclohexyl-7-thiaprostaglandin E$_1$ methyl ester (No. 138) and its 15-epi-ent:

(1) A pentane solution (5.5 ml, 7.68 mmoles) of 1.4M t-butyllithium was added at −78° C. to an ether solution (10 ml) of 1.46 g (3.84 mmoles) of 3(S)-t-butyldimethylsilyloxy-3-cyclohexyl-1-iodo-trans-1-propene, and the mixture was stirred for 2 hours. To the resulting solution was added a solution which was prepared by adding 1.50 g (9.22 mmoles) of hexamethylphosphorus triamide to a suspension of 795 mg (4.61 mmoles) of phenylthiocopper (I) in 5 ml of ether, and stirring the mixture at room temperature until the solution became homogeneous. The mixture was stirred at −78° C. for 1 hour. The reaction solution was reacted with 930 mg (2.5 mmoles) of 4(RS)-t-butyldimethylsilyloxy-2-(5-methoxycarbonylpentylthio)-2-cyclopentenone obtained in Example 1, (1), and the reaction mixture was worked up, in a similar way to Example 1, (2) to give 3.7 g of a crude product. The crude product was subjected to silica gel column chromatography (hexane/ethyl acetate=9/1) to give 900 mg (1.44 mmoles, 57.5%) of a mixture of 11,15-bis(t-butyldimethylsilyl)-16,17,18,19,20-pentanor-15-cyclohexyl-7-thiaprostaglandin E$_1$ methyl; ester (No. 205) and its 15-epi-ent.

NMR (CDCl$_3$, δ(ppm)): 0.06 (12H, s, SiCH$_3$), 0.84 (18H, s, tBu), 1.0–1.9 (17H, m), 2.1–3.0 (8H, m), 3.56 (3H, s, COOCH$_3$), 3.75 (3H, m, C$_{11}$-H and C$_{15}$-H), 5.3–5.6 (2H, m, olefin proton).

IR (liquid film, cm$^{-1}$): 1740, 1255, 1110, 1070, 1050, 885, 840, 780.

(2) The bis-silyl ether obtained in (1) above (900 mg, 1.44 mmoles) was dissolved in a mixture of 30 ml of acetic acid, 10 ml of water, and 10 ml of tetrahydrofuran in a similar way to Example 1, (3), and reacted at room temperature for 3 days to deprotect the bis-silyl ether. The product was worked up in the same way as in Example 1, (3) to give a crude product. The crude product was chromatographed on a silica gel column using hexane/ethyl acetate (1/3) as an eluent to give 100 mg (0.25 mmole, 17%) of 16,17,18,19,20-pentanor-15-cyclohexyl-7-thiaprostaglandin E$_1$ methyl ester (No. 138), and 64 mg (0.16 mmole, 11%) of its 15-epi-ent.

Compound No. 138

Thin-layer chromatography (hexane/ethyl acetate=½): RF=0.25.

NMR (CDCl$_3$, δ(ppm): 0.9–1.9 (17H, m), 2.1–3.4 (10H, m), 3.61 (3H, s, COOCH$_3$), 3.7–4.5 (2H, m, C$_{11}$-H and C$_{15}$-H), 5.47–5.73 (2H, m, olefin proton).

IR (liquid film, cm$^{-1}$): 3410, 1735, 1260, 1200, 1170, 1080, 1000, 970, 890, 730.

Mass (20 eV; m/e, %): 398 (M$^+$, 2), 380 (28), 367 (3), 362 (18), 269 (38), 265 (42), 237 (100), 220 (39), 219 (42), 202 (93), 83 (97).

High resolution mass (70 eV): C$_{21}$H$_{34}$O$_5$S (M$^+$) calc. 398.2125; found 398.2143.

mp 56°–58° C. (recrystalized from petroleum ether-ether), [α]$_D^{21}$ −19.5°, (methanol, C 2.44).

15-Epi-ent of Compound No. 138

Thin-layer chromatography (hexane/ethyl acetate=½): RF=0.40.

NMR (CDCl$_3$, δ(ppm)): 0.9–2.0 (17H, m), 2.1–3.35 (10H, m), 3.61 (3H, s, COOCH$_3$), 3.83 (2H, m, C$_{11}$-H and C$_{15}$-H), 5.57–5.73 (2H, m, olefin proton).

IR (liquid film, cm$^{-1}$): 3430, 1735, 1260, 1200, 1170, 1080, 1000, 970, 915, 730.

Mass (20 eV; m/e, %): 398 (M$^+$, 1), 380 (23), 367 (1), 362 (16), 269 (40), 265 (32), 237 (96), 219 (32), 202 (88), 119 (56), 101 (60), 83 (100).

High resolution mass (70 eV): C$_{21}$H$_{34}$O$_5$S (M$^+$) calc. 398.2125; found 398.2119.

EXAMPLE 3

Mixture of 15(S)-t-butyldimethylsilyl-11-trimethylsilyl-16,17,18,19,20-pentanor-15-cyclohexyl-7-thiaprostaglandin E$_1$ methyl ester (No. 206) and its 15-epi-ent:

A pentane solution (0.8 ml, 1.1 mmoles) of 1.4M t-butyllithium was added to an ether solution (3 ml) of 210 mg (0.55 mmole) of 3(S)-t-butyldimethylsilyloxy-3-cyclohexyl-1-iodo-trans-1-propene, and the mixture was stirred at −70° C. for 1.5 hours. To the solution was added an ether (0.5 ml) solution of 94.6 mg of phenylthiocopper (I) and 165 mg of hexamethylphosphorus triamide. To the resulting solution was added 170 mg (0.515 mmole) of 4(RS)-trimethylsilyloxy-2-(5-methoxycarbonylpentylthio)-2-cyclopentenone. Upon the addition, the solution became a yellow clear solution, and thereafter, a precipitate formed. The mixture was further reacted at −70° C. for 30 minutes, at −40° C. to −50° C. for 30 minutes, and finally at −30° C. for 20 minutes. After the reaction, the reaction mixture was worked up in the same way as in Example 1, (2). The product was chromatographed on a silica gel column using hexane/ethyl acetate (95/5) as an eluent to give 48 mg (0.082 mmole, 16%) of 15(S)-t-butyldimethylsilyl-11-trimethylsilyl-16,17,18,19,20-pentanor-15-cyclohexyl-7-thiaprostaglandin $E_1$ methyl ester.

EXAMPLE 4

16,17,18,19,2-pentanor-15-cyclohexyl-7-thioprostaglandin $E_1$ (No. 111):

Five grams of hog pancrease lipase (a product of Sigma Company) was added to 50 ml of an aqueous solution of 0.1 M sodium chloride and 0.05 M of potassium chloride, and the emulsion was vigorously stirred at 0° C. for 1.5 hours. The emulsion was centrifuged at 2° C. for 30 minutes by a high speed cooling centrifuged separator (9,000 rpm). The supernatant liquid was collected, and neturalized to pH 7 with 0.1 N sodium hydroxide to give a crude enzyme solution. An acetone solution (0.8 ml) of 50 mg (0.126 mmole) of 16,17,18,19,20-pentanor-15-cyclohexyl-7-thiaprostaglandin $E_1$ methyl ester (No. 138) obtained in Example 2was added to the enzyme solution, and subjected to hydrolysis at 4° C. for 20 minutes by sonication with an ultrasonic reactor. The reaction solution was poured into 300 ml of acetone, and the insoluble matter was separated off by filtration through Celite. The resulting acetone solution was concentrated under reduced pressure. To the remaining aqueous layer (about 50 ml) were added a saturated aqueous solution of ammonium sulfate and 200 ml of ethyl acetate to perform extraction. The extract was washed with a saturated aqueous solution of sodium chloride. dried over magnesium sulfate and concentrated to give 60 mg of a crude product. The crude product was subjected to thin-layer chromatography (hexane/ethyl acetate/ethyl acid=30/70/1) to give 17 mg (0.044 mmole, 35%) of 16,17,18,19,20-pentanor-15-cyclohexyl-7-thiaprostaglandin $E_1$ (No. 111).

Rf (hexane/ethyl acetate=1/5): 0.11.

NMR ($CDCL_3$, δ (ppm)): 0.8–1.9 (17H, m), 1.9–3.1 (3H, m), 3.7–4.3 (2H, m $C_{11}$-H and $C_{15}$-H), 5.53 (3H, bs, OH and COOH), 5.61 (2H, m, olefin proton).

IR ($CDCL_3$):

3400, 2950, 2860, 1740, 1710, 1450, 1410, 1345, 1260, 1080, 1000, 970, 910 cm$^{-1}$.

EXAMPLE 5

15-epi-ent- of 16,17,18,19,20-pentanor-15-cyclohexyl-7-thiaprostaglandin $E_1$ (No. 111):

By a similar hydrolyzing method to Example 4, 32 mg (0.080 mmole) of the 15γepi-ent of 16,17,18,19,20-pentanor-15-cyclohexyl-7-thiaprostaglandin $E_1$ methyl ester (No. 138) was converted into the corresponding carboxylic acid (13 mg, 0.034 mmole, 42%).

Rf(hexane/ethyl acetate =1/5): 0.22.

NMR ($CDCL_3$, δ(ppm)): 0.8–1.9 (17H, m), 2.1–3.1 (8H, m), 3.7–4.2 (2H, m, $C_{11}$-H and $C_{15}$-H), 4.93 (3H, bs, OH and COOH), 5.55–5.77 (2H, m, olefin proton).

IR (neat): 3400, 2950, 2860, 1740, 1710, 1450, 1410, 1260, 1080, 1000, 970, 910 cm$^{-1}$.

EXAMPLE 6

16,17,18,19,20-pentanor-15-cyclohexyl-7-thiaprostaglandin $E_1$ methyl ester S-oxide (No. 195):

50 mg (0.126 mmole) of 16,17,18,19,20-pentanor-15-cyclohexyl-7-thiaprostaglandin $E_1$ methyl ester (No. 138) was dissolved in 10 ml of methanol, and 2 ml of an aqueous 80 mg (0.38 mmole) of sodium periodate was added at room temperature. The mixture was stirred for 2 hours. To the solution were added ethyl acetate and a saturated aqueous solution of sodium chloride to perform extraction. The organic layer was washed with a saturated aqueous solution of sodium chloride, dried over anhydrous magnesium sulfate, and concentrated. The residue was chromatographed on a silica gel column using ethyl acetate/methanol (29/1) as an eluent to give 32 mg (0.077 mmole; yield 61%) of the desired compound (No. 195).

NMR ($CDCL_3$, δ (ppm)): 0.8–2.0 (17H, m), 2.2–2.8 (7H, m), 3.0 (2H, m), 3.33 (1H, m), 3.69 (3H, s), 3.85 (1H, m), 4.17 (1H, m), 5.60–5.85 (2H, m).

IR (neat): 3400, 3060, 1740, 1245, 1045, 1020, 735 700 cm$^{-1}$.

Mass (12 eV; m/e %): 396 (0.1, M-18), 380 (7), 378 (3), 362 (2), 269 (11), 237 (8), 218 (10), 202 (9), 190 (9), 178 (12), 146 (91), 136 (28), 129 (20), 118 (22), 111 (100), 108 (29), 101 (30), 83 (82).

High resolution mass (70 eV): $C_{21}H_{32}O_5S$ (M-$H_2O$) calc. 396.1968; found 396.1949.

EXAMPLE 7

15-epi-ent of 16,17,18,19,20-pentanor-15-cyclohexyl-7-thiaprostaglandin $E_1$ methyl ester S-oxide (No. 195):

211 mg (0.53 mmole) of a 15-epi-enantiomer of 16,17,18,19,20-pentanor-15-cyclohexyl-7-thiaprostaglandin $E_1$ methyl ester was dissolved in 15 ml of methanol, and a solution of 400 mg (1.9 mmoles) of sodium periodate in 3.5 ml of water was added. The mixture was stirred at room temperature for 2 hours. After the reaction, dichloromethane and an aqueous solution of sodium chloride were added to perform extraction. The matter was dried anhydrous magnesium sulfate, and concentrated to give a crude product. The crude product was chromatographed on a silica gel column using ethyl acetate/methanol (29/1) as an eluent to give 147 mg (0.355 mmole; yield 67%) of the desired 15-epi-ent of compound No. 195.

NMR ($CDCL_3$, δ (ppm)): 0.8–1.9 (17H, m), 2.1–3.2 (7H, m), 3.0 (2H, m), 3.37 (1H, m), 365 (3H, s), 3.83 (1H, m), 4.20 (1H, m), 5.63–5.83 (2H, m).

IR (neat): 3380, 1740, 1200, 1170, 1020, 780, 760 cm$^{-1}$.

High resolution mass (70 eV): $C_{21}H_{32}O_5S$ (M-$H_2O$) calc. 396.1968; found 396.1950.

EXAMPLE 8

16,17,18,19,20-pentanor-15-cyclohexyl-7-thiaprostaglandin $E_1$ phenyl ester (No. 144) and its 15-epi-ent:

(1) 686 mg (2.09 mmoles) of 4(RS)-tetrahydropyranyloxy-2-(5-carboxypentylthio)-2-cyclopentenone and 295 mg (3.14 mmoles) of phenol were dissolved in 10 ml of dichloromethane, and 0.1 ml of pyridine was added. To the solution was added 10 ml of a dichloromethane solution of 860 mg (4.18 mmoles) of dicyclohexylcarbodiimide. The mixture was stirred at room temperature for 18 hours. After the reaction, ethyl acetate was added to the reaction mixture. The organic layer was washed successively with an aqueous solution of sodium bicarbonate, an aqueous solution of potassium bisulfate, and an aqueous solution of sodium chloride, dried, and then concentrated. The residue was chromatographed on a silica gel column using hexane/ethyl acetate (7/2) as an eluent to give 653 mg (1.62 mmoles; yield 77.3%) of 4(RS)-tetrahydropyranyloxy-2-(5-phenoxycarbonylpentylthio)-2-cyclopentenone.

IR (neat): 3350, 3080, 1760, 1720, 1595, 1570, 1500, 1285, 1200, 1160, 1120, 1070, 1030, 960, 940, 870, 810, 750, 690 cm$^{-1}$.

NMR (CDCl$_3$, δ (ppm)): 1.3–2.1 (12H, m), 2.5–3.1 (6H, m), 3.3–4.2 (2H, m), 4.7–5.1 (2H, m), 7.0–7.6 (6H, m).

(2) A similar reaction to Example 1, (2) was carried out using 1.4 g (3.68 mmoles) of 3(S)-t-butyldimethylsilylbutyllithium and 1.41 g (3.5 mmoles) of dl-4-tetrahydropyranyloxy-2-(5-phenoxycarbonylpentylthio)-2-cyclopentenone. There was obtained 1.16 g (1.76 mmoles; yield 47.9%) of a mixture of 11-tetrahydropyranyl-15-t-butyldimethylsilyl-16,17,18,19,20-pentanor-15-cyclohexyl-7-thiaprostaglandin E$_1$ phenyl ester (No. 208) and its 15-epi-ent.

IR (neat): 1760, 1595, 1500, 1255, 1200, 1125, 1075, 1035, 970, 840, 775, 690 cm$^{-1}$.

NMR (CDCL$_3$, δ (ppm)): 0.03 (6H, s), 0.88 (9H, s), 1.1–1.9 (23H, m), 2.25–3.05 (8H, m), 3.2–4.3 (4H, m), 4.55–4.75 (1H, m), 5.5–5.7 (2H, m), 6.7–7.6 (5H, m).

(3) The mixture obtained in (2) was worked up in a similar way to Example 1, (3) using a mixture of acetic acid, water, and tetrahydrofuran to give 74 mg (0.161 mmole; yield 46%) of 16,17,18,19,20-pentanor-15-cyclohexyl-7-thiaprostaglandin E$_1$ phenyl ester (No. 144) and 100 ml (0.217 mmole; yield 6.2%) of its 15-epi-ent.

Compound No. 144

IR (neat): 3400, 3080, 1755, 1595, 1450, 1200, 1165, 1125, 1080, 1000, 970, 930, 890, 745, 690 cm$^{-1}$.

NMR (CDCL$_3$ δ (ppm)): 0.9–2.0 (17H, m), 2.3–3.5 (10H, m), 3.6–4.4 (2H, m), 5.5–5.8 (2H, m), 6.9–7.6 (5H, m).

Mass (20 eV; m/e %): 460 (M$^+$, 2), 422 (18), 424 (10), 377 (16), 367 (34), 349 (74), 331 (69), 283 (38), 265 (38), 237 (65), 219 (100), 202 (72), 201 (58), 175 (76), 147 (33), 131 (63), 94 (91), 83 (63), 69 (52).

High resolution mass (70 eV); C$_{26}$H$_{34}$O$_4$S (M-H$_2$O) calc. 442.2181; found 442.2216.

15-epi-ent of compound No. 144

IR (neat): 3430. 3080, 1755, 1595, 1500, 1450, 1240, 1200, 1165, 1125, 1075, 1020, 970, 930, 815, 735, 690 cm$^{31}$ $^1$.

NMR (CDCL$_3$, δ (ppm)): 0.9–1.9 (17H, m), 2.3–3.3 (10H, m), 3.7–4.2 (2H, m), 5.6–5.8 (2H, m), 6.9–7.4 (5H, m).

Mass (20 eV; m/e, %): 460 (M$^+$, 0.1), 442 (6), 424 (4), 377 (6), 367 (11), 349 (31), 331 (30) 284 (100), 265 (16), 237 (26), 219 (33), 202 (36), 201 (23), 175 (23), 147 (41), 131 (31), 101 (31), 97 (39), 94 (72), 83 (29), 69 (68).

High resolution mass (70 eV); C$_{26}$H$_{34}$O$_4$S calc. 442.2181; found 442.2174.

EXAMPLE 9

16,17,18,19,20-pentanor-15-cyclohexyl-7-thiaprostaglandin E$_1$ decyl ester (No, 143) and its 15-epi-ent:

(1) 2.18 g (12 mmoles) of 4(RS)-tetrahydropyranyloxy-2-cyclpentenone was dissolved in 25 ml of methanol, and 5 ml (44 mmoles) of 30% hydrogen peroxide was added. The mixture was cooled to 0° C., and several drops of 2N sodium hydroxide was added. The mixture was stirred for 30 minutes. Ether was added, and the separated organic layer was washed with an aqueous solution of sodium chloride, dried over anhydrous magnesium sulfate, and concentrated to give 4-tetrahydropyranyloxy-2,3-epoxycyclopentanone.

This product was dissolved in 20 ml of methanol, and 0.5 ml of triethylamine was added. A solution of 1.83 g (6.35 mmoles) of decyl 6-mercaptohexanoate in 10 ml of methylene chloride was added at 0° C., and the mixture was stirred at room temperature for 20 hours. The reaction mixture was concentrated and subjected to dry column chromatography (hexane/ethyl acetate=3/1) to give 2.25 g (4.81 mmoles; 75.7%) of 4(RS)-tetrahydropyranyloxy-2-(5-decyloxycarbonylpentylthio)-2-cyclpentenone.

NMR (CDCL$_3$, δ (ppm)): 0.87 (3H), 1.24–1.61 (28H), 2.1–2.9 (6H, m), 3.35–4.2 (4H, m), 4.5–5.1 (2H, m).

(2), The same procedure as in Example 2, (1) was repeated using 1.224 g (2.62 mmoles) of 4(RS)-tetrahydropyranyloxy-2-(5-decyloxycarbonylpentylthio)-2-cyclopentenone obtained in (1) above and 1.09 g (2.88 mmoles) of 3(S)-t-butyldimethylsilyloxy-3-cyclohexyl-1-iodo-trans-1-propene. There was obtained 1.29 g (1.79 mmoles; yield 68.2%) of a mixture of 15-t-butyldimethylsilyl-11-tetrahydropyranyl-16,17,18,19,20-pentanor-15-cyclohexyl-7-thiaprostaglandin E$_1$ decyl ester (No. 207) and its 15-epi-ent.

IR (neat): 2950, 2880, 1740, 1665, 1260, 1180, 1130, 1080, 1040, 975, 920, 900, 840, 780, 740 cm$^{-1}$.

NMR (CDCl$_3$, δ (ppm)): 0.04 (6H, s), 0.84 (12H, s+m), 1.1–1.8 (39H, m), 2.1–8.5 (8H, m), 3.3–4.2 (6H, m), 4.61 (1H, m), 5.47–5.67 (2H, m).

(3) The mixture obtained in (2) was dissolved in 30 ml of acetic acid, 10 ml of water, and 10 ml of tetrahydrofuran, and reacted at room temperature for 4 days to deprotect it. The deprotected product was worked up in substantially a similar way to Example 1, (3) to give 30 mg (57 μmoles, yield 2.2%) of 16,17,18,19,20-pentanor-15-cyclohexyl-7-thiaprostaglandin E$_1$ decyl ester (No. 143) and 60 mg (115 μmoles, yield 44%) of its 15-epi-ent.

Compound No. 143

Rf(hexane/ethyl; acetate=⅓): 0.45
IR (neat): 3420, 2950, 2880, 1740, 1455, 1265, 1180, 1135, 1080, 1005, 975, 895, 740 cm$^{-1}$.

NMR (CDCl$_3$, δ (ppm)): 0.86 (3H, m), 1.1–1.9 (33H,m), 2.1–3.4 (10H, m), 3.7–4.2 (4H, m), 5.45–5.75 (2H, m).

Mass (20 eV; m/e, %): 506 (22, M-H$_2$O), 488 (70), 395 (25), 348 (10), 330 (22), 302 (31), 255 (29), 237 (100), 233 (25), 219 (39), 218 (33), 202 (70), 201 (36), 200 (40), 131 (54), 130 (60), 115 (72), 111 (39), 102 (51), 97 (48), 83 (55), 71 (38), 69 (34), 57 (52).

High resolution mass (20 eV): C$_{30}$H$_{50}$O$_4$S (M-H$_2$O) calc. 506.3434; found 506.3520.

15-epi-ent of compound No. 143

Rf (hexane ethyl acetate=⅓): 0.55.
IR (neat): 3440, 2950, 2870, 1740, 1450, 1260, 1180, 1130, 1080, 1000, 975, 890, 735 cm$^{-1}$.

NMR (CDCl$_3$, δ (ppm)): 0.87 (3H, m), 1.1–1.8 (33H, m), 2.0–3.1 (10H, m), 3.7–4.2 (4H, m), 5.55–5.75 (2H, m).

Mass (20 eV; m/e, %) 506 (M-H$_2$O, 19), 488 (9), 395 (23), 238 (16), 237 (100), 219 (11), 209 (11), 202 (26), 131 (12), 130 (11), 119 (10), 118 (16), 111 (11), 83 (18).

High resolution mass (20 eV): $C_{30}H_{50}O_4S$ $(M-H_2O)$ calc. 506.3434; found 506.3344.

Example 10

16,17,18,19,20-pentanor-15-cyclohexyl-7-thiaprostaglandin $E_1$ benzyl ester (No. 147) and its 15-epi-ent:

(1) 2.09 g (6.1 mmoles) of 4(RS)-tetrahydropyranyloxy-2-(5-carboxypentylthio)-2-cyclopentenone was dissolved in 20 ml of dichloromethane, and to this solution were added 5 ml of a dichloromethane solution of 956 mg (7 mmoles) of isobutyl chloroformate and 5 ml of a dichloromethane solution of 808 mg (8 mmoles) of triethylamine. The mixture was stirred at −78° C. for 30 minutes. Then, 5 ml of a dichloromethane solution of 864 mg (8 mmoles) of benzyl alcohol was added, and the reaction was carried out for 18 hours while gradually raising the temperature to room temperature. After the reaction, the reaction mixture was extracted with ethyl acetate. The extract was washed with an aqueous solution of hydrogen chloride and an aqueous solution of sodium bicarbonate, then dried, and concentrated. The resulting crude product was chromatographed on a silica gel column using hexane/ethyl acetate (3.5/1) as an eluent to give 1.30 g (3.11 mmoles; yield 51%) of 4(RS)-tetrahydropyranyloxy-2-(5-benzyloxycarbonylpentyl-thio)-2-cyclopentenone.

IR (neat): 3080, 3050, 2950, 2880, 1735, 1720, 1575, 1280, 1180, 1135, 1080, 1030, 960, 870, 815, 750, 735, 700 cm$^{-1}$.

NMR (CDCl$_3$, δ (ppm)): 1.3–1.9 (12H, m), 2.1–3.0 (6H, m), 3.3–4.1 (2H, m), 4.6–5.0 (2H, m), 5.09 (2H, s), 6.93 (1H, t, J=2.5Hz), 7.32 (5H, s).

(2) The procedure of Example 2, (1) was substantially followed using 1.18 g (3.1 mmoles) of 3(S)-t-butyl-dimethyl-silyloxy-3-cyclohexyl-1-iodo-trans-1-propene and 1.18 g (2.82 mmoles) of 4(RS)-tetrahydropyranyloxy-2-(5-benzyloxy-carbonylpentylthio)-2-cyclopentenone. There was obtained 1.45 g of a mixture of 11-tetrahydropyranyl-15-bis(t-butyl-dimethylsilyl)-16,17,18,19,20-pentanor-15-cyclohexyl-7-thiaprostaglandin $E_1$ benzyl ester (No. 209) and its 15-epi-ent.

IR (neat): 3050, 1740, 1455, 1260, 1130, 1080, 1040, 975, 915, 840, 780, 750, 700 cm$^{-1}$.

NMR (CDCl$_3$, δ (ppm)): 0.04 (6H, s), 0.84 (9H, s), 0.9–1.9 (23H, m), 2.1–3.1 (8H, s), 3.2–4.3 (4H, m), 4.64 (1H, m), 5.07 (2H, s), 5.4–5.7 (2H, m), 7.31 (5H, s).

(3) 1.45 g of the mixture obtained in (2) above was subjected to deprotection reaction by substantially a similar operation to Example 2, (2) to give 43 mg (91 μmoles, yield 3.2%) of 16,17,18,19,20-pentanor-15-cyclo-hexyl-7-thiaprostaglandin $E_1$ benzyl ester (No. 147) and 55 mg (116 μmoles, yield 4.1%) of its 15-epi-ent.

Compound No. 147

IR (neat): 3420, 3080, 1740, 1450, 1265, 1170, 1080, 1000, 970, 910, 735, 700 cm$^{-1}$.

NMR (CDCl$_3$, δ (ppm)): 0.8–1.9 (17H, m), 2.2–3.1 (10H, m), 3.7–4.0 (2H, m), 5.06 (2H, s), 5.47–5.73 (2H, m), 7.29 (5H, s).

Mass (20 eV; m/e, %): 474 (M$^+$, 0.1), 456 (4), 438 (2), 391 (3), 365 (8), 347 (6), 345 (10), 237 (15), 202 (14), 111 (14), 107 (12), 91 (100), 83 (36).

High resolution mass (70 eV): $C_{27}H_{36}O_4S$ $(M-H_2O)$ calc. 456.2473; found 456.2473.

15-epi-ent of compound No. 147

IR (neat): 3430, 3080, 1740, 1455, 1390, 1360, 1275, 1180, 1140, 1080, 1035, 980, 920, 740 705 cm$^{-1}$.

NMR (CDCl$_3$, δ (ppm)): 0.8–1.9 (17H, m), 2.1–3.1 (10H, m), 3.6–4.0 (2H, m), 5.07 (2H, s), 5.53–5.73 (2H, m), 7.27 (5H, s).

Mass (20 eV; m/e, %): 474 (M$^+$, 0.5), 456 (3), 438 (4), 391 (2), 365 (5), 347 (5), 329 (3), 237 (8), 219 (12), 218 (13), 202 (11), 123 (12), 111 (10), 107 (11), 91 (100). 83 (19).

High resolution mass (70 eV): $C_{27}H_{38}O_5S$ (M$^+$) calc. 474.2455; found 474.2524.

Example 11

16,17,18,19,20-pentanor-15-cyclohexyl-2,2-dimethyl-7-thiaprostaglandin $E_1$ methyl ester (No. 151) and its 15-epi-ent:

(1) 1.21 g (5.3 mmoles) of 2,3-epoxy-4(RS)-t-butyl-dimethylsilyloxycyclopentan-1-one was dissolved in 2.5 ml of methanol and then under cooling, 1.0 g (5.3 mmoles) of methyl 2,2-dimethyl-6-mercaptohexanoate was added. The mixture was stirred for 3 hours. After stirring, the solvent was removed by evaporation, and after adding water, the residue was extracted with ether. The extract was washed with a saturated aqueous solution of sodium chloride, dried over anhydrous magnesium sulfate and concentrated. The resulting crude product was chromatographed on a silica gel column using ethyl acetate-hexane (1/9) as an eluent to give 1.364 g (yield 64%) of 4(RS)-t-butyldi-methylsilyloxy-2-(5-methoxycarbonyl-5,5-dimethylpentylthio)-2-cyclopentenone.

NMR (CDCl$_3$, δ (ppm)): 0.11 (6H, s), 0.90 (9H, s), 1.14 (6H, s), 1.3–2.0 (6H, br), 2.28 (1H, dd, J=19Hz, 25 Hz), 2.6–3.1 (3H, m), 3.65 (3H, s), 4.92 (1H, m), 6.79 (1H, d, J=2.5Hz).

(2) A similar reaction to Example 2, (1) was carried out except using 800 mg (2.0 mmoles) of 4(RS)-t-butyl-di-methylsilyloxy-2-(5-methoxycarbonyl-5,5-dimethyl-pentylthio)-2-cyclopentenone and 836 mg (2.2 mmoles) of 3(S)-t-butyldi-methylsilyloxy-3-cyclohexyl-1-iodo-trans-1-propane. There was obtained 1.3 g (1.99 mmoles, yield 99%) of a mixture of 11,15-bis(t-butyl-dimethylsilyl)-2,2-dimethyl-16,17,18,19,20-pentanor-15-cyclohexyl-7-thiaprostaglandin $E_1$ methyl ester (No. 216) and its 15-epi-ent.

Rf (hexane/ethyl acetate=9/1): 0.45.

IR (neat): 2960, 2950, 2860, 1735, 1460, 1360, 1255, 1190, 1140, 1110, 1065, 835, 775 cm$^{-1}$.

NMR (CDCl$_3$, δ (ppm)): 0.06 (12H, s), 0.86 (18H, s), 1.0–1.9 (17H, m), 1.13 (6H, s), 2.3–3.1 (6H, m), 3.60 (3H, s), 3.7–4.3 (2H, m), 5.4–5.6 (2H, m).

(3) 1.3 g (1.99 mmoles) of 11,15-bis(5-butyldi-methyl-silyl)-2,2-dimethyl-16,17,18,19,20-pentanor-15-cyclohexyl-7-thiaprostaglandin $E_1$ methyl ester (No. 216) obtained in (2) above dissolved in 10 ml of acetonitrile, and 0.5 ml of a 47% aqueous solution of hydrofluric acid was added. The mixture was stirred at room temperature for 1 hour. Similarly to the above, the reaction mixture was extracted with ethyl acetate. The extract was washed with an aqueous solution of sodium bicarbonate and an aqueous solution of sodium chloride, dried over anhydrous magnesium sulfate, and concentrated to give 860 mg of a crude product. The crude product was chromatographed on a silica gel column using hexane/ethyl acetate (1/3) as an eluent to give 200 mg (0.47 mmole, 24%) of 16,17,18,19,20-pentanor-15- cyclohexyl-2,2-dimethyl-7-thiaprostaglandin E₁ methyl ester (No. 151) and 243 mg (0.57 mmole, 29%) of its 15-epi-ent.

Compound No. 151

Rf (hexane/ethyl acetate=1/2): 0.25.

NMR (CDCl₃, δ (ppm)): 1.11 (6H, s), 1.2–1.8 (17H, m), 2.3–3.2 (8H, m), 3.62 (3H, s), 3.7–4.2 (2H, m), 5.47–5.73 (2H, m).

IR (neat): 3420, 2950, 2860, 1730, 1450, 1280, 1240, 1195, 1150, 1080, 1000, 970, 890, 860, 735 cm⁻¹.

Mass (20 eV): 426 (M⁺, 1), 408 (20), 395 (1), 390 (14), 349 (9), 343 (8), 331 (9), 330 (8), 325 (8), 311(9), 297 (25), 283 (34), 265 (40), 237 (90), 220 (22), 219 (23), 202 (100), 157 (28), 129 (34), 120 (32), 119 (60 ), 111 (38), 109 (30), 108 (38), 107 (33), 102 (38), 97 (40), 96 (26), 95 (30), 83 (68), 55 (26).

High resolution mass (70 eV): $C_{23}H_{38}O_5S$ (M⁺) calc. 426.2444 found 426.2453

15-epi-ent of compound No. 151

Rf (hexane/ethyl acetate=1/2): 0.35.

NMR (CDCl₃, δ (ppm)): 1.1–1.8 (17H, m), 1.12 (6H, s), 2.3–3.1 (7H, m), 3.63 (3H, s), 3.7–4.3 (2H, m), 5.6–5.77 (2H, m).

IR (neat): 3450, 2950, 2860, 1730, 1450, 1390, 1280, 1240, 1200, 1145, 1080, 975, 890, 860, 735 cm⁻¹.

Mass (20 eV): 426 (M⁺, 0.5), 408 (7), 395 (0.5), 390 (7), 349 (3), 343 (4), 331 (3), 311 (4), 287 (32), 283 (16), 268 (10), 265 (10), 254 (10), 237 (27), 227 (26), 226 (43), 202 (32), 167 (28), 157 (39), 155 (28), 129 (70), 111 (28), 102 (96), 97 (100), 87 (30), 83 (48), 73 (28), 69 (19), 55 (62).

High resolution mass (70 eV): $C_{23}H_{36}O_4S$ (M-H₂O) calc. 408.2337; found 408.2301.

Example 12

16,17,18,19,20-pentanor-15-cyclohexyl-2-methyl-7-thiaprostaglandin E₁ methyl ester (No. 150) and its 15-epi-ent:

(1) 726 mg of 4(RS)-hydroxy-2-(5-methoxycarbonyl-5-methylpentylthio)-2-cyclopentenone and 596 mg (3.96 mmoles) of t-butyldimethylsilyl chloride were dissolved in 10 ml of hexamethylphosphoric triamide, and the reaction was performed at 0° C. for 20 hours. After the reaction, the reaction mixture was extracted with ethyl acetate. The extract was dried and concentrated to give 2.09 g of a crude product. The crude product was chromatographed on a silica gel column using hexane/ethyl acetate (4/1) as an eluent to give 594 mg (1.54 mmoles; yield 58.3%) of 4(RS)-t-butyldimethylsilyloxy-2-(5-methoxycarbonyl-5-methyl-pentylthio)-2-cyclopentenone.

NMR (CDCl₃, δ (ppm)): 0.11 (6H, s), 0.87 (9H, s), 1.11 (3H, d, J=7Hz), 1.25–1.8 (6H, m), 2.3–3.0 (5H, m), 3.61 (3H, s), 4.75–5.0 (1H, m), 6.72 (1H, s, J=2.5Hz).

(2) The procedure of Example 2, (1) was substantially followed using 642 mg (1.69 mmoles) of 3(S)-t-butyldimethylsilyloxy-3-cyclohexyl-1-iodo-trans-1-propene and 594 mg (1.54 mmoles) of 4(RS)-t-butyldimethylsilyloxy-2-(5-methoxycarbonyl-5-methylpentylthio)-2-cyclopentenone. There was obtained 552 mg (0.86 mmole; yield 56%) of a mixture of 11,15(S)-bis(t-butyldimethylsilyl)-2-methyl-16,17,18,19,20-pentanor-15-cyclohexyl-7-thiaprostaglandin E₁ methyl ester (No. 215) and its 15-epi-ent.

IR (neat): 2950, 2880, 1740, 1580, 1460, 1360, 1260, 1110, 1070, 1005, 970, 885, 840, 780, 740, 670 cm⁻¹.

NMR (CDCl₃, δ (ppm)): 0.08 (12H, s), 0.87 (18H, s), 1.0–1.9 (17H, m), 1.12 (3H, d, J=7Hz), 2.2–3.3 (7H, m), 3.61 (3H, s), 3.7–4.1 (2H, m).

(3) To 1.01 g of the mixture obtained in (2) above were added 0.5 ml of 47% hydrofluoric acid and 10 ml of acetonitrile, and the reaction was performed at room temperature for 2 hours. After the reaction, the reaction mixture was extracted with ethyl acetate. The extract was washed with an aqueous solution of sodium bicarbonate and an aqueous solution of sodium chloride, dried and concentrated to give 625 mg of a crude product. The crude product was chromatographed on a column of silica gel using hexane/ethyl acetate (1/3) as an eluent to give 73 mg (0.177 mmole; yield 11.5%) of 16,17,18,19,20-pentanor-15-cyclohexyl-2-methyl-7-thiaprostaglandin E₁ methyl ester (No. 150) and 70 mg (0.170 mmole; yield 11.0%) of its 15epi-ent.

Compound No. 150

Rf (hexane/ethyl acetate=1/3): 0.25.

IR (neat): 3400, 2950, 2870, 1740, 1450, 1380, 1245, 1200, 1160, 1080, 970, 895, 740 cm⁻¹.

NMR (CDCl₃, δ (ppm)): 1.15 (3H, d, J=7Hz), 1.3–2.2 (17H, m), 2.4–3.2 (9H, m), 3.67 (3H, s), 3.8–4.2 (2H, m), 5.5–5.8 (2H, m).

Mass (20 eV; m/e, %) 412 (M⁺, 1), 394 (17), 376 (15), 329 (12), 297 (22), 283 (15), 279 (22), 269 (27), 251 (35), 237 (34), 220 (34), 219 (35), 202 (39), 176 (26), 143 (33), 119 (24), 115 (30), 111 (64), 109 (45), 108 (33), 83 (100).

High resolution mass (70 eV); $C_{22}H_{34}O_4S$ (M-H₂O) calc. 394.2180; found 394.2239.

15-epi-ent of compound No. 150

IR (neat): 3450, 2950, 2870, 1740, 1450, 1380, 1245, 1205, 1160, 1080, 1045, 975, 740 cm⁻¹.

NMR (CDCl₃, δ (ppm)): 1.12 (3H, d, J=7Hz), 1.3–1.8 (17H, m), 2.2–3.2 (9H, m), 3.63 (3H, s), 3.7–4.3 (2H, m), 5.6–5.8 (2H, m).

Mass (20 eV; m/e, %): 412 (M⁺, 1), 394 (14), 376 (15), 329 (11), 297 (17), 287 (16), 279 (19), 269 (19), 251 (32), 237 (24), 220 (28), 219 (28), 202 (44), 180 (24), 143 (31), 111 (57), 109 (39), 88 (40), 83 (100).

High resolution mass (70 eV): $C_{22}H_{34}O_4S$ calc. 394.2180; found 394.2089.

Example 13

16,17,18,19,20-pentanor-15-cyclohexyl-2,2-difluoro-7-thiaprostaglandin E₁ methyl ester (No. 154) and its 15-epi-ent:

(1) The procedure of Example 11, (1) was substantially followed using 1.53 g (6.7 mmoles) of 4(RS)-t-butyldimethylsilyloxy-2,3-epoxycyclopentanone and 1.21 g (6.11 mmoles) of methyl 2,2-difluoro-6-mercaptohexanoate to give 1.56 g (3.84 mmoles; 63%) of 4(RS)-t-butyldi-methylsilyloxy-2-(5,5-difluoro-5-methoxycarbonylpentylthio)-2-cyclopentenone.

IR (neat): 1775, 1720 cm⁻¹.

NMR (CDCl₃, δ (ppm)): 0.88 (s, 9H), 2.30 (1H, dd, J=18Hz, 2.5 Hz), 2.5–3.1 (3H, m), 3.83 (3H, s), 4.90 (1H, m), 6.79 (1H, d, J=2.5Hz).

(2) A similar operation to Example 1, (2) was carried out using 408 mg of 4(RS)-t-butyldimethylsilyloxy-2-(5,5-difluoro-5-methoxycarbonylpentylthio)-2-cyclopentenone and 418 mg of 3(S)-t-butyldimethylsilyloxy-3-cyclohexyl-1-iodo-trans-1-propene. There was obtained 132 mg(yield 20%) a mixture of 11,15-bis(t-butyldimethylsilyl)-16,17,18,19,20-pentanor-15- cyclohexyl-2,2-difluoro-7-thiaprostaglandin $E_1$ methyl ester (No. 217) and its 15-epi-ent.

(3) 132 mg of the mixture was deprotected in a similar way to Example 11, (3) to give 21 mg (yield 24.4%) of 16,17,18,19,20-pentanor-15-cyclohexyl-2,2-difluoro-7-thiaprostaglandin $E_1$ methyl ester (No. 154) and 23 mg (yield 26%) of its 15-epi-ent.

Compound No. 154

NMR (CDCl$_3$, δ (ppm)): 5.60 (2H, m), 3.8–4.2 (2H, m), 3.80 (3H, s), 2.3–3.0 (6H, m), 0.9–2.3 (17H, m).

IR (neat): 3500, 3950, 2850, 1665, 1540, 1450, 1350, 1310, 1200, 1095 cm$^{-1}$.

Mass (20 eV): 434 (M$^+$), 416, 398, 351, 345, 333, 305, 290, 202 (100%) 153.

15-epi-ent.

NMR (CDCl$_3$, δ (ppm)): 5.65 (2H, m), 3.8–4.2 (2H, m), 3.80 (3H, s), 2.3–2.9 (6H, m), 0.9–2.3 (17H, m).

IR (neat): 3400, 2950, 2850, 1760, 1450, 1350, 1320, 1200, 1095 cm$^{-1}$.

Example 14

17(S),20-dimethyl-7-thiaprostaglandin $E_1$ methyl ester (No. 131):

(1) A similar operation to Example 1, (2) was carried out using 400 mg (1.09 mmoles) of 4(R)-t-butyldimethyl-silyloxy-2-(5-methoxycarbonylpentylthio)-2-cyclopentenone and 430 mg (1.09 mmoles) of 3(S)-t-butyldimethylsilyloxy-1-iodo-5(S)-methyl-trans-1-nonene. There was obtained 202 mg (yield 29.4%) of 11,15-bis(t-butyldimethylsilyl)-17(S),20-dimethyl-7-thiaprostaglandin $E_1$ methyl ester (No. 203).

NMR (CDCl$_3$, δ (ppm)): 0.1 (12H, s), 0.85 (18H, s), 0.9 (6H, m), 1–1.8 (15H, m), 2.2–3.0 (8H, m), 3.65 (3H, s), 4.0–4.4 (2H, m), 5.6 (2H, m).

(2) Twenty milliliters of a 5% acetonitrile solution of 47% hydrofluoric acid was added to 160 mg (0.25 mmole) of 11,15(S)-bis(t-butyldimethylsilyl)-17(S),20-dimethyl-7-thiaprostaglandin $E_1$ methyl ester at room temperature, and the mixture was stirred for 1 hour. After the stirring, water and chloroform was added to perform extraction. The extract was washed with an aqueous solution of sodium bicarbonate, dried, and concentrated to give a crude product. The crude product was chromatographed on a silica gel column using hexane/ethyl acetate (1/3) as an eluent to give 30 mg (yield 29%) of 17(S),20-dimethyl-7-thiaprostaglandin $E_1$ methyl ester (No. 131).

NMR (CDCl$_3$, δ(ppm)): 0.9 (6H, m), 1–1.7 (15H, m), 2.2–3.0 (8H, m), 3.65 (3H, s), 4.0–4.4 (2H, m), 5.0 (2H, m).

EXAMPLE 15

17(R),20-dimethyl-7-thiaprostaglandin $E_1$ methyl ester (No. 134):

(1) A similar operation to Example 1, (2) was carried out using 448 mg of 4(R)-t-butyldimethylsilyloxy-2-(5-methoxycarbonylpentylthio)-2-cyclopentenone and 475 mg of 3(S)-t-butyldimethylsilyloxy-5(R)-methyl-1-iodo-trans-1-nonene. There was obtained 234 mg (yield 30.5%) of 11,15-bis(t-butyldimethylsilyl)-17(R),20-dimethyl-7-thiaprostaglandin $E_1$ methyl ester.

NMR (CDCl$_3$, δ(ppm)): 0.1 (12H, s), 0.85 (18H, s), 0.9 (6H, m), 1–1.8 (15H, m), 2.1–3.0 (8H, m), 3.65 (3H, s), 4.0–4.4 (2H, m), 5.6 (2H, m).

(2) 234 mg of the resulting 11,15-bis(t-butyldimethylsilyl)-17(R),20-dimethyl-7-thiaprostaglandin $E_1$ methyl ester was deprotected in a similar way to Example 14, (2) to give 54.3 mg (yield 36%) of 17(R),20-dimethyl-7-thiaprostaglandin $E_1$ methyl ester (No. 134).

NMR (CDCl$_3$, δ(ppm)): 5.65 (2H, m), 4.0–4.3 (2H,m), 3.63 (3H, s), 2.1–2.9 (8H, m), 1.0–2.10 (15H, m), 0.8–1.0 (6H, m).

IR (neat): 3400, 2960, 2860, 1740, 1460, 1440, 1370, 1260, 1200, 1180 cm$^{-1}$.

EXAMPLE 16

16,17,18,19,20-pentanor-15-cyclohexyl-2,3-dehydro-7-thiaprostaglandin $E_1$ methyl ester (No. 156) and its 15-epi-ent:

(1) 2.80 g (12.2 mmoles) of 4(R)-t-butyldimethyl-silyloxy-2,3-epoxycyclopentanone and 1.30 g (12.2 mmoles) of 4-mercaptobutan-1-ol were dissolved in 12 ml of methanol, and with stirring 1.87 ml (13.5 mmoles) of triethylamine was added. The stirring was continued for 30 minutes. Ten milliliters of a saturated aqueous solution of ammonium chloride was added, and the mixture was concentrated. The residue was extracted with ethyl acetate, dried over anhydrous magnesium sulfate, filtered and concentrated. The resulting oily product was chromatographed on a silica gel column using hexane/ethyl acetate (8/1) as an eluent to give 3.12 g (81%) of 4(RS)-t-butyldimethylsilyloxy-2-(4-hydroxybutylthio)-2-cyclopentenone.

Rf (hexane/ethyl acetate=1/1): 0.40.

NMR (CDCl$_3$, δ (ppm)): 0.12 (s, 6H, —Si(CH$_3$)$_2$), 0.89 (s, 9H, —SiC(CH$_3$)$_3$), 1.4–2.0 (m, 5H, —SCH$_2$CH$_2$CH$_2$CH$_2$OH), 2.23

(dd, J = 2.4, 19.0 Hz, 1H, HCH—C$\overset{\diagup O}{\diagdown}$), 2.69

(dd, J = 19.0, 5.4 Hz, 1 H, HCH—C$\overset{\diagup O}{\diagdown}$), 2.5–2.9 (m, 2H, S—CH$_2$—), 3.52 (brt, J=5.4 Hz, 2H, —CH$_2$OH), 4.6–5.0

(m, 1 H, HC—OSi), 6.69

(d, J = 2.8 Hz, 1 H, —CH).

(2) Oxalyl chloride (48 microliters; 0.55 mmole) was dissolved in 2 ml of dry dichloromethane, and the solution was cooled to −30° C. Dimethyl sulfoxide (78 microliters; 110 mmoles) was added, and the mixture was stirred for 3 minutes. A solution of 158 mg (0.5 mmole) of 4(R)-t-butyldimethylsilyloxy-2-(4-hydroxybutylthio)-2-cyclopentenone in 1 ml of dry dichloromethane was added over the course of 1 minute, and the mixture was stirred at −30° C. for 30 minutes. Then, 5 ml of a saturated aqueous solution of ammonium chloride was added, and the mixture was extracted with dichloromethane. The organic layers were combined, dried over anhydrous sodium sulfate, filtered, and concentrated. The resulting oily product was chromatographed on a silica gel column using hexane/ethyl acetate (5/1) to give 96 mg (yield 61%) of 4(RS)-t-butyldimethylsilyloxy-2-(4-oxobutylthio)-2-cyclopentenone.

Rf (hexane/ethyl acetate=1/1): 0.61.

IR (neat): 1720, 1575, 1260 cm$^{-1}$.

NMR (CDCl$_3$, δ(ppm)): 0.10 (s, 6H, —Si(CH$_3$)$_2$), 0.88 (s, 9H, —SiC(CH$_3$)$_3$), 1.94 (quintet, J=7.0 Hz, 2H, —CH$_2$CH$_2$CH$_2$), 2.32

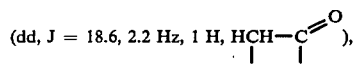

2.62 (t, J=6.8 Hz, 2H, CH$_2$CHO), 2.79

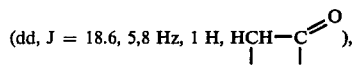

2.86 (t, J=7.4 Hz, 2H, —SCH$_2$—), 4.90

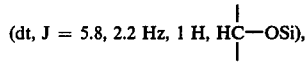

6.88

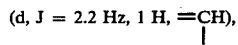

9.75 (s, 1H, CHO).

(3) 96 mg (2.0 mmoles) of 50% sodium hydride was suspended in 5 ml of dry benzene, and 841 mg (4.0 mmoles) of methyl diethylphosphonoacetate was added. The mixture was stirred for 10 minutes. 600 mg (1.91 mmoles) of 4(RS)-t-butyldimethylsilyloxy-2-(4-oxobutylthio)-2-cyclopentenone was dissolved in 10 ml of dry benzene. The solution was stirred under ice cooling. To the resulting solution was added the above reaction mixture. The mixture was stirred further for 15 minutes. The reaction mixture was washed with a saturated aqueous solution of ammonium chloride, and extracted with ethyl acetate. The extract was dried over anhydrous dodium sulfate, and concentrated. The resulting oily product was chromatographed on a silica gel column using hexane/ethyl acetate (8/1) as an eluent to give 531 mg (yield 75%) of 4(RS)-t-butyldimethylsilyloxy-2-(5-methoxycarbonyl-trans-4-pentenylthio)-2-cyclopentenone.

IR (neat): 1729, 1659, 1572, 1620 cm$^{-1}$.

NMR (CDCl$_3$, δ (ppm)): 0.13 (s, 6H, si(CH$_3$)$_2$), 0.88 (s, 9H, SiC(CH$_3$)$_3$), 1.4-2.0 (m, 2H, SCH$_2$CH$_2$CH$_2$), 2.0-2.5 (m, 2H, CH$_2$CH=CH), 2.27

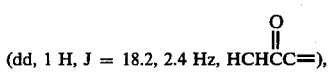

2.75

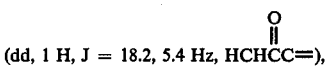

2.77 (t, 2H, J=7.4 Hz, SCH$_2$), 3.63 (s, 3H, OCH$_3$), 4.87 (dt, 1H, J=5.6, 2.2 Hz, SiOCH<), 5.80 (d, 1H, J=16.0 Hz, CH=CHCO$_2$Me), 6.74

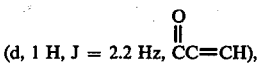

6.83 (dt, 1H, J=16.0, 6.8 Hz, CH=CHCO$_2$Me).

Mass; m/e 370 (M+).

(4) Using 1.23 g (3.3 mmoles) of 4(RS)-t-butyldimethylsilyloxy-2-(5-methoxycarbonyl-trans-4-pentenylthio)-2-cyclopentenone and 1.63 g (4.29 mmoles) of 3-t-butyldimethylsilyloxy-3-cyclohexyl-1-iodo-trans-1-propene, a similar operation to Example 1, (2) was performed. There was obtained 1.02 g (yield 49%) of a mixture of 16,17,18,19,20-pentanor-11,15-bis(t-butyldimethylsilyl)-15-cyclohexyl-2,3-dehydro-7-thiaprostaglandin E$_1$ methyl ester and its 15-epi-ent.

Rf (hexane/ethyl acetate=5/1): 0.44.

IR (neat): 1727, 1655, 1260 cm$^{-1}$.

NMR (CDCl$_3$, δ (ppm)): 0–0.1 (m, 12H, Si(CH$_3$)$_2$×2), 0.87 (s, 18H, C(CH$_3$)$_3$×2), 0.8–2.0 (m, 13H, C-C$_6$H$_{11}$, SCH$_2$CH$_2$CH$_2$), 2.0–3.1

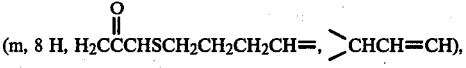

3.64 (s, 3H, —OCH$_3$), 3.6-4.3 (m, 2H, SiOCH×2), 5.4–5.7 (m, 2H, —CH=CH—), 5.80 (d, 1H, J=1.60 Hz, CH=CHCO$_2$Me), 6.85 (dt, 1H, J=16.0, 6.0 Hz, —CH=CHCO$_2$Me).

(5) 1.0 g (1.5 mmoles) of the mixture obtained in (4) above was deprotected in substantially a similar way as in Example 11, (3) to give 90 mg (yield 14%) of 16,17,18,19,20-pentanor-15-cyclohexyl-2,3-dehydro-7-thiaprostaglandin E$_1$ methyl ester (No. 156) and 100 mg (yield 16%) of its 15-epi-ent.

Compound No. 156

Melting point: 81.0°–83.0° C.
Rf (hexane/ethyl acetate=1/4): 0.23.
IR (CHCl$_3$): 3420, 1748, 1715, 1657 cm$^{-1}$.
NMR (CDCl$_3$, δ (ppm)): 0.8–2.0 (m, 13H, C-C$_6$H$_{11}$, SCH$_2$CH$_2$CH$_2$), 2.0–3.1

3.71 (s, 3H, —OCH$_3$),
3.6–4.3 (m, 2H, HOCH<×2), 5.4–5.8 (m, 2H, —CH=CH—), 5.82 (d, 1H, J=10.2 Hz, CH=CHCO$_2$Me), 6.87 (dt, 1H, J=16.0, 6.4 Hz, CH=CHCO$_2$Me)

Mass (m/e): 396 (M+).

15-epi-ent of compound No. 156

Rf (hexane/ethyl acetate=1/4): 0.33.

IR++(CHCl₃): 3450, 1710, 1658 cm⁻¹.

NMR (CDCl₃, δ (ppm)): 0.9–2.0 (m, 13H, C-C₆H₁₁, SCH₂CH₂CH₂), 2.0–3.1

(m, 10 H, H₂CCCHSCH₂CH₂CH₂CH=,

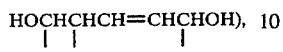

HOCHCHCH=CHCHOH), 3.63 (s, 3H, —OCH₃), 3.5–4.4 (m, 2H, HOCH< ×2), 6.5–6.8 (m, 2H, CH=CH), 5.76 (d, 1H, CH=CHCO₂Me), 6.81 (dt, 1H, J=15.4, 6.4 Hz, —CH=CHCO₂Me).

EXAMPLE 17

17(S),20-dimethyl-2,3-dehydro-7-thiaprostaglandin E₁ methyl ester (No. 160):

(1) A similar operation to Example 1, (2) was performed using 550 mg (1.48 mmoles) of 4(R)-t-butyldimethylsilyloxy-2-(5-methoxycarbonyl-trans-4-pentenylthio)-2-cyclopentenone and 645 mg (1.63 mmoles) of 3(S)-t-butyldimethylsilyloxy-1-iodo-5(S)-methyl-trans-1-nonene which were obtained by optically resolving the compound obtained in Example 16, (3). There was obtained 130 mg (yield 21%) of 11,15-bis(t-butyldimethylsilyl)-17(S),20-dimethyl-2,3-dehydro-7-thiaprostaglandin E₁ methyl ester (No. 219).

NMR (CDCl₃, δ (ppm)): 0.09 (17H, s), 0.7–0.9 (6H, m), 0.90 (18, s), 1.00–1.9 (13H, m), 2.00–2.85 (6H, m), 3.65 (3H, s), 3.95–4.30 (2H, m), 5.50 (2H, m), 5.80 (1H, d, J=15 Hz), 6.90 (1H, d, t, J=15 Hz, 6 Hz).

(2) 130 mg of 11,15-bis(t-butyldimethylsilyl)-17(S),20-dimethyl-2,3-dehydro-7-thiaprostaglandin E₁ methyl ester (No. 219) obtained in (1) above was deprotected by using a 5% acetonitrile solution (15 ml) of 47% hydrofluororic acid in a similar way to Example 11, (3) to give 54 mg (yield 63%) of 17(S),20-dimethyl-2,3-dehydro-7-thiaprostaglandin E₁ methyl ester (No. 160).

Rf (ethyl acetate/hexane=3/1): 0.3.

IR (neat): 3450, 2950, 2900, 1740, 1720, 1660, 1440, 1320, 1270, 1200 cm⁻¹.

NMR (CDCl₃, δ (ppm)): 0.8–1.0 (6H, m), 1.0–2.80 (13H, m), 2.1–2.9 (6H, m), 3.65 (3H, s), 4.0–4.3 (2H, m), 5.65 (2H, m), 5.85 (1H, d, J=15 Hz), 6.95 (1H, dt, J=15 Hz, 6 Hz).

EXAMPLE 18

16,17,18,19,20-pentanor-15-cyclohexyl-7-thiaprostaglandin E₁ morpholinamide (No. 179) and its 15-epi-ent:

(1) 492 mg (1.37 mmoles) of 4(RS)-t-butyldimethylsilyloxy-2-(5-carboxypenthylthio)-2-cyclopentenone was dissolved in 5 ml of methylene chloride, and the solution was cooled to −40° C. Then, 307 mg (2.25 mmoles) of isobutyl chloroformate, 303 mg (3.0 mmoles) of triethylamine and then 653 mg (7.5 mmoles) of morpholine were added. While the temperature was gradually raised to room temperature, the mixture was stirred for 20 hours. The reaction mixture was extracted with ethyl acetate, washed with dilute hydrochloric acid, an aqueous solution of sodium bicarbonate and then an aqueous solution of sodium chloride, and dried over anhydrous magnesium sulfate to give 972 mg of a crude product. The crude product was chromatographed on a silica gel column using hexane/ethyl acetate (1/1) as an eluent to give 576 mg (1.35 mmoles; yield 98%) of 4(RS)-t-butyldimethylsilyloxy-2-(5-morpholinocarbonylpentylthio)-2-cyclopentenone.

IR (neat): 3070, 2980, 2950, 2880, 1720, 1645, 1575, 1460, 1435, 1360, 1300, 1280, 1260, 1235, 1180, 1120, 1080, 950, 910, 835, 780, 735 cm⁻¹.

NMR (CDCl₃, δ (ppm)): 0.13 (6H, s), 0.88 (9H, s), 1.4–1.8 (6H, m), 2.0–3.0 (6H, m), 3.3–3.7 (8H, m), 4.77–5.0 (1H, m), 6.76 (1H, d, J=3 Hz).

(2) Substantially a similar operation as in Example 2, (1) was carried out using 609 mg (1.43 mmoles) of 4(RS)-t-butyldimethylsilyloxy-2-(5-morpholinocarbonylpentylthio)-2-cyclopentenone and 418 mg (1.1 mmoles) of 3(S)-t-butyldimethylsilyloxy-3-cyclohexyl-1-iodo-trans-1-propene. There was obtained 330 mg (0.49 mmole; yield 44.5%) of a mixture of 11,15-bis(t-butyldimethylsilyl)-16,17,18,19,20-pentanor-15-cyclohexyl-7-thiaprostaglandin E₁ morpholinamide (No. 210) and its 15-epi-ent.

RF (hexane/ethyl acetate=1/1): 0.50.

IR (neat): 2950, 2870, 1740, 1650, 1460, 1430, 1360, 1255, 1120, 1070, 970, 885, 840, 775, 735, 665 cm⁻¹.

NMR (CDCl₃, δ(ppm)): 0.07 (12H, s), 0.88 (18H, s), 0.9–1.9 (17H, m), 2.1–2.8 (8H, m), 3.3–4.2 (10H, m), 5.4–5.65 (2H, m).

(3) At room temperature 0.5 ml of 47% hydrofluoric acid and 10 ml of acetonitrile were added to 330 mg of the mixture formed in (2) above, and the mixture was stirred at room temperature for 30 minutes. After the stirring, water and ethyl acetate were added to perform extraction. The extract was washed with an aqueous solution of sodium bicarbonate and an aqueous solution of sodium chloride, and dried over magnesium sulfate. The solvent was evaporated to give a crude product. The crude product was chromatographed on a silica gel column using ethyl acetate as an eluent to give 59 mg (0.130 mmole; yield 27%) of 16,17,18,19,20-pentanor-15-cyclohexyl-7-thiaprostaglandin E₁ morpholinamide (No. 179) and 49 mg (0.108 mmole; yield 22%) of its 15-epi-ent.

Compound No. 179

Rf (ethyl acetate): 0.15.

NMR (CDCl₃, δ (ppm)): 0.8–1.9 (17H, m), 2.1–3.2 (10H, m), 3.2–4.4 (10H, m), 5.5–5.75 (2H, m).

IR (neat): 3420, 2950, 2880, 1740, 1630, 1440, 1360, 1300, 1275, 1240, 1120, 1085, 1070, 1035, 970, 895, 845, 735 cm⁻¹.

Mass (20 eV); 435 (M-H₂O, 10), 417 (10), 406 (2), 352 (13), 324 (46), 237 (11), 217 (21), 216 (100), 200 (6), 184 (31), 142 (12), 129 (29), 88 (48).

High resolution mass (70 eV): C₂₄H₃₇NO₄S (M-H₂O) calc. 435.2445; found 435.2448.

15-epi-ent of compound No. 179

Rf (ethyl acetate): 0.25.

NMR (CDCl₃, δ (ppm)): 0.8–1.9 (17H, m), 2.1–3.2 (10H, m), 3.3–4.3 (10H, m), 5.55–5.75 (2H, m).

IR (neat): 3430, 2950, 2880, 1745, 1630, 1445, 1360, 1300, 1275, 1235, 1120, 1070, 1035, 895, 845 cm⁻¹.

Mass (20 eV): 435 (M-H₂O, 9), 417 (9), 406 (2), 352 (12), 324 (38), 237 (9), 217 (20), 216 (100), 200 (5), 184 (25), 142 (9), 129 (21), 88 (37).

High resolution mass (70 eV); C₂₄H₃₇NO₄S (M-H₂O) calc. 435.2445; found 435.2448.

EXAMPLE 19

16,17,18,19,20-pentanor-15-cyclohexyl-7-thiaprostaglandin $E_1$ 5,6-dihydrophenanthridinamide (No. 180) and its 15-epi-ent:

(1) 2.12 g (5.92 mmoles) of 4(RS)-t-butyldimethylsilyloxy-2-(5-carboxypentylthio)-2-cyclopentenone was dissolved in 30 ml of dichloromethane, and the solution was cooled to $-40°$ C. To the solution were added 970 mg (920 microliters; 7.10 mmols) of isobutyl chloroformate and 896 mg (1.24 ml, 8.88 mmoles) of triethylamine were added, and the mixture was stirred at $-40°$ C. for 30 minutes. Then, 10 ml of a dichloromethane solution of 1.29 g (7.10 mmoles) of 5,6-dihydrophenanthridine was added to the resulting mixture. The temperature was gradually raised to room temperature over 20 hours. After the reaction, ethyl acetate was added to the reaction mixture to perform extraction. The extract was washed with dilute hydrochloric acid, an aqueous solution of sodium bicarbonate and then an aqueous solution of sodium chloride, dried over anhydrous magnesium sulfate, and concentrated. The resulting crude product was chromatographed on a silica gel column using hexane/ethyl acetate (4/1) as an eluent to give 2.657 g (5.1 mmoles; yield 86%) of 4(RS)-t-butyldimethylsilyloxy-2-(5-carboxypentylthio)-2-cyclopentenone 5,6-dihydrophenanthridinamide.

IR (neat): 3180, 2950, 2910, 2870, 1720, 1660, 1600, 1575, 1490, 1460, 1440, 1390, 1360, 1280, 1260, 1220, 1190, 1175, 1080, 945, 905, 835, 815, 780, 765, 740, 665 $cm^{-1}$.

NMR (CDCl$_3$, $\delta$(ppm)): 0.12 (6H, s), 0.88 (9H, s), 1.2–1.8 (6H, m), 2.3–3.0 (6H, m), 4.75–5.0 (3H, bs), 6.72 (1H, d, J=2.5 Hz), 7.2–7.4 (6H, m), 7.6–7.9 (2H, m).

(2) A similar operation to Example 2, (1) was carried out using 2.657 g (5.1 mmoles) of 4(RS)-t-butyldimethylsilyloxy-2-(5-carboxypentylthio)-2-cyclopentenone 5,6-dihydrophenanthridinamide obtained in (1) above and 2.52 g (6.63 mmoles) of 3(S)-t-butyldimethylsilyloxy-3-cyclohexyl-1-iodo-trans-1-propene. There was obtained 2.79 g (3.6 mmoles; yield 70.6%) of a mixture of 11,15-bis(t-butyldimethylsilyl)-16,17,18,19,20-pentanor-15-cyclohexyl-7-thiaprostaglandin $E_1$ 5,6-dihydrophenanthridinamide (No. 211) and its 15-epi-ent.

IR (neat): 3190, 3150, 2950, 2870, 1740, 1660, 1605, 1490, 1460, 1445, 1390, 1255, 1220, 1190, 1110, 1070, 1050, 1005, 970, 940, 885, 835, 775, 740, 670 $cm^{-1}$.

NMR (CDCl$_3$, $\delta$(ppm)): 0.07 (12H, s), 0.89 (18H, s), 1.1–1.9 (17H, m), 2.3–2.8 (8H, m), 3.7–4.2 (2H, m), 4.9 (2H, bs), 5.4–5.7 (2H, m), 7.2–7.5 (6H, m), 7.6–7.9 (2H, m).

(3) 775 mg (1.0 mmole) of the mixture obtained in (2) above was deprotected by using 10 ml of acetonitrile and 0.5 ml of 47% hydrofluoric acid to give 175 mg (0.32 mmole; yield 32%) of 16,17,18,19,20-pentanor-15-cyclohexyl-7-thiaprostaglandin $E_1$ 5,6-dihydrophenanthridinamide (No. 18) and 188 mg (0.34 mmole; yield 34%) of its 15-epi-ent.

Compound No. 180

Rf (hexane/ethyl acetate=1/3): 0.20.
IR (neat):
3440, 3100, 3050, 2950, 2870, 1740, 1640, 1605, 1490, 1445, 1395, 1245, 1195, 1085, 1050, 1010, 970, 910, 765 $cm^{-1}$.

NMR (CDCl$_3$, $\delta$ (ppm)): 0.8–1.9 (17H, m), 2.2–3.6 (10H, m), 3.6–4.5 (2H, m), 4.89 (2H, bs), 5.45–5.75 (2H, m), 7.1–7.5 (6H, m), 7.6–7.9 (2H, m).

15-epi-ent- of compound No. 180

Rf (hexane/ethyl acetate=1/3): 0.35.

IR (neat): 3440, 3100, 3050, 2950, 2880, 1740, 1640, 1605, 1490, 1445, 1395, 1225, 1195, 1085, 1010, 975, 910, 765 $cm^{-1}$.

NMR (CDCl$_3$, $\delta$ (ppm)): 0.8–1.8 (17H, m), 2.–3.5 (10H, m), 4.81 (2H, bs), 3.6–4.4 (2H, m), 5.5–5.7 (2H, m), 7.1–7.45 (6H, m), 7.6–7.9 (2H, m).

EXAMPLE 20

16,17,18,19,20-pentanor-15-cyclohexyl-7-thiaprostaglandin $E_1$ amide (No. 178) and its 15-epi-ent:

(1) 775 mg (1.0 mmole) of the mixture of 11,15-bis(t-butyldimethylsilyl)-16,17,18,19,20-pentanor-15-cyclohexyl-7-thiaprostaglandin $E_1$ 5,6-dihydrophenanthridinamide (No. 211) and its 15-epi-ent, which was obtained in Example 19, (2), was dissolved in a mixture of 19 ml of acetonitrile, 1 ml of water and 2 ml of tetrahydrofuran. 1.81 g (3.3 mmoles) of cerium (IV) ammonium nitrate hydrate was added at 0° C. to the solution. The mixture was stirred at 0° C. for 20 minutes and at room temperature for 5 minutes. After the reaction, ethyl acetate was added to perform extraction. The separated organic layer was washed with 1N hydrochloric acid and then an aqueous solution of sodium chloride, dried over magnesium sulfate, and then concentrated to give 664 mg of a crude product. A portion (616 mg) of the crude product was chromatographed on a silica gel column using hexane/ethyl acetate (2/1) as an eluent to give 340 mg (0.56 mmole; yield 56%) of a mixture of 11,15-bis(t-butyldimethylsilyl)-16,17,18,19,20-pentanor-15-cyclohexyl-7-thiaprostaglandin $E_1$ and its 15-epi-ent.

IR (neat): 3000, 2950, 2890, 1745, 1715, 1465, 1260, 1120, 1070, 885, 840, 780, 740 $cm^{-1}$.

NMR (CDCl$_3$, $\delta$ (ppm)): 0.04 (12H, s), 0.83 (18H, s), 0.9–1.9 (17H, m), 2.1–3.5 (8H, m), 3.6–4.4 (2H, m), 5.3–5.6 (2H, m), 9.50 (1H, b).

(2) 229 mg (0.37 mmole) of the mixture obtained in (1) was dissolved in 3 ml of methylene chloride, and the solution was cooled to $-40°$ C. 76 mg (73 microliters; 0.56 mmole) of isobutyl chloroformate and then 71 mg (100 microliters, 0.7 mmole) were added to the solution. The mixture was stirred for 30 minutes. Then, 1 ml of aqueous ammonia was added, and the temperature was gradually raised to room temperature over the course of 18 hours. After the reaction, the reaction mixture was extracted with ethyl acetate. The extract was washed with dilute hydrochloric acid, an aqueous solution of sodium bicarbonate, and an aqueous solution of sodium chloride, dried over magnesium sulfate, and concentrated to give 410 mg of a crude product. The crude product was subjected to dry column chromatography and developed with hexane/ethyl acetate (1/1) to give 176 mg (0.288 mole; yield 78%) of a mixture of 11,15-bis(t-butyldimethylsilyl)-16,17,18,19,20-pentanor-15-cyclohexyl-7-thiaprostaglandin $E_1$ amide and its 15-epi-ent.

Rf (hexane/ethyl acetate=1/1): 0.20.
IR (neat): 3370, 3220, 2960, 2890, 1750, 1670, 1620, 1465, 1410, 1365, 1260, 1120, 1075, 1010, 975, 940, 890, 840, 780, 740, 670 $cm^{-1}$.

NMR (CDCl$_3$, δ (ppm)): 0.06 (12H, s), 0.86 (18H, s), 0.9–1.9 (17H, m), 3.7–4.4 (2H, m), 5.55–5.80 (2H, m), 6.08 (1H, bs), 6.40 (1H, bs).

(3) 176 mg (0.288 mmole) of the mixture obtained in (2) above was deprotected by using 10 ml of acetonitrile and 0.5 ml of 47% hydrofluoric acid to give 50 mg (0.13 mmole; yield 35%) of 16,17,18,19,20-pentanor-15-cyclohexyl-7-thiaprostaglandin E$_1$ amide (No. 178) and 50 mg (0.13 mmole; yield 35%) of its 15-epi-ent.

Compound No. 178

Rf (ethyl acetate/methanol=10/1): 0.18.
IR (neat): 3400, 2950, 2880, 1740, 1665, 1615, 1455, 1410, 1150, 1085, 1000, 975, 910 cm$^{-1}$.
NMR (CDCl$_3$, δ (ppm)): 0.8–1.9 (17H, m), 1.9–3.1 (8H, m), 3.5–4.3 (2H, m), 5.4–5.9 (6H, m), 15-epi-ent of compound No. 178

IR: 3400, 2950, 2880, 1740, 1665, 1615, 1455, 1410, 1150, 1085, 1005, 975, 910 cm$^{-1}$.
NMR (CDCl$_3$, δ (ppm)): 0.8–1.9 (17H, m), 1.9–3.1 (8H, m), 3.7–4.3 (2H, m), 5.45–5.85 (6H, m).

EXAMPLE 21

16,17,18,19,20-pentanor-15-cyclohexyl-7-thiaprostaglandin E$_1$ (No. 111) and its 15-epi-ent:

87 mg (142 μmoles) of 11,15-bis(t-butyldimethylsilyl)-16,17,18,19,20-pentanor-15-cyclohexyl-7-thiaprostaglandin E$_1$ obtained in Example 20, (1) was dissolved in 2 ml of acetonitrile, and 0.1 ml of 47% hydrofluoric acid was added. The mixture was stirred at room temperature for 30 minutes. After the reaction, the reaction mixture was extracted with ethyl acetate, the extract was washed with an aqueous solution of sodium bicarbonate and an aqueous solution of sodium chloride, dried over magnesium sulfate, and concentrated to give 65 mg of a crude product. The crude product was subjected to thin-layer chromatography (hexane/ethyacetate=1/5) to give 10 mg (26 μmoles; yield 18%) of 16,17,18,19,20-pentanor-15-cyclohexyl-7-thiaprostaglandin E$_1$ (No. 111) and 12 mg (31 μmoles; yield 22%) of its 15-epi-ent. The physical properties of these compounds were identical with those of the compounds obtained in Examples 4 and 5.

EXAMPLE 22

1,16,17,18,19,20-hexanor-2-hydroxymethyl-15-cyclohexyl-7-thiaprostaglandin E$_1$ (No. 185) and its 15-epi-ent:

(1) 440 mg (1.28 mmoles) of 2-(6-hydroxyhexylthio)-4-t-butyldimethylsilyloxy-2-cyclopentenone and 225 mg (1.50 mmoles) of t-butyldimethylsilyl chloride were treated at room temperature for 2 hours in 3 ml of N,N-dimethyl formamide in the presence of 204 mg (3.0 mmoles) of imidazole. After the reaction, the reaction mixture was extracted with hexane to give 640 mg of a crude product. The crude product was purified by thin-layer chromatography (cyclohexane/ethyl acetate=4/6) to give 437 mg (75%) of 2-(6-t-butyldimethylsilyloxyhexylthio)-4-t-butyldimethylsilyloxy-2-cyclopentenone.

NMR (60 MHz, ppm, CCl$_4$): 6.67 (1H, d, J=2 Hz), 4.85 (1H, m), 3.5 (2H, m), 3.0–2.5 (2H), 2.2 (2H, dd, J=2 Hz, 18 Hz), 1.7–1.2 (8H), 0.9 (18H), 0.08 (12H).

Mass (20 eV, m/e): 458 (M+).

(2) A similar operation to Example 1, (2) was carried out using 2-(6-t-butyldimethylsilyloxyhexylthio)-4(RS)-t-butyldimethylsilyloxy-2-cyclopentenone obtained in (1) above and 363 mg of 3(S)-t-butyldimethylsilyloxy-3-cyclohexyl-1-iddo-trans-1-propene. There was obtained 390 mg (yield 57.5%) of a mixture of 16,17,18,19,20-hexanor-2,11,15-tris(t-butyldimethylsilyl)-7-thiaprostaglandin E$_1$ and its 15-epi-ent.

NMR (CDCl$_3$, δ (ppm)): 0.09 (18H, s), 0.9 (27H), 1.0–2.0 (19H, m), 2.1–2.9 (6H, m), 3.4–3.8 (4H, m), 5.65 (2H, m).

(3) The mixture obtained in (2) above was deprotected in a similar way to Example 11, (3) to give 40 mg (yield 19.3%) of 1,16,17,18,19,20-hexanor-1-hydroxymethyl-15-cyclohexyl-7-thiaprostaglandin E$_1$ (No. 185) and 43 mg (yield 21.2%) of its 15-epi-ent.

Compound No. 185

IR (neat): 3400, 2950, 2850, 1740, 1585, 1510, 1440, 1350 cm$^{-1}$.
NMR (CDCl$_3$, δ (ppm)): 1.0–2.10 (19H, m), 2.3–2.95 (6H, m), 3.5–3.8 (4H, m), 5.65 (2H, m)

15-epi-ent of compound No. 185

NMR (CDCl$_3$, δ (ppm)): 1.0–2.0 (19H, m), 2.0–3.0 (6H, m), 3.4–3.8 (4H, m), 5.70 (2H, m).

EXAMPLE 23

1,16,17,18,19,20-hexanor-2-acetoxymethyl-15-cyclohexyl-7-thiaprostaglandin E$_1$ (No. 186) and its 15-epi-ent.

(1) 1.26 g (5.94 mmoles) of 4(RS)-t-butyldimethylsilyloxy-2,3-epoxy cyclopentanone and 804 mg (6.0 mmoles) of 5-hydroxy-1-pentanethiol were dissolved in 10 ml of methanol, and 606 mg (6 mmoles) of triethylamine was added. After the reaction was carried out for 10 minutes, the solvent was evaporated to give 2.1 g of a crude product. The crude product was subjected to dry column chromatography and developed with hexane/ethyl acetate (7/3) to give 710 mg (2.16 mmoles; yield 31%) of 4-t-butyldimethylsilyloxy-2-(6-hydroxyhexylthio)-2-cyclopentenone.

NMR (CDCl$_3$, δ (ppm)): 0.90 (9H, s), 1.4 (8H, bs), 2.5 (1H, dd, J=3, 16 Hz), 2–3 (3H), 3.6 (2H, t, J=7 Hz), 2.8 (1H, dd, J=4, 16 Hz), 4.9 (1H, m), 6.77 (1H, d, J=2.5 Hz).

(2) 700 mg (2.13 mmoles) of 4(RS)-t-butyldimethylsilyloxy-2-(6-hydroxyhexylthio)-2-cyclopentenone, 1020 mg (10 mmoles) of acetic anhydride and 1580 mg (20 mmoles) of pyridine were mixed, and stirred at room temperature for 2 hours. After the reaction, methanol was added. The solvent was removed to give 795 mg of 4-t-butyldimethylsilyloxy-2-(6-acetoxyhexylthio)-2-cyclopentenone as a nearly pure product.

NMR (CDCl$_3$, δ (ppm)): 0.9 (9H, s), 1.46 (8H, bs), 2.01 (3H, s), 2.53 (1H, dd, J=2.5, 16 Hz), 2.85 (1H, dd, J=3, 16 Hz), 2–3 (2H), 4.00 (2H, d, J=7 Hz), 4.9 (1H, m), 6.77 (1H, d, J=3 Hz).

(3) A similar operation to Example 1, (2) was carried out using 370 mg (0.95 mmole) of 4(RS)-t-butyldimethylsilyloxy-2-(6-acetoxyhexylthio)-2-cyclopentenone and 456 mg (1.2 mmoles) of 3(S)-t-butyldimethylsilyloxy-3-cyclohexyl-1-iodo-trans-1-propene. There was obtained 387 mg (0.60 mmole; yield 63%) of a mixture of 11,15-bis(t-butyldimethylsilyl)-1,16,17,18,19,20-hexanor-2-acetoxymethyl-15-cyclohexyl-7-thiaprostaglandin E$_1$ (No. 213) and its 15-epi-ent.

Rf (hexane/ethyl acetate=4/1): 0.50.

NMR (CDCL$_3$, δ (ppm)): 0.88 (18H, s), 1.0–2.0 (17H), 2.03 (3H, s), 2.2–2.9 (6H), 4.05 (2H, t, J=7 Hz), 3.7–4.2 (2H), 5.58 (2H, m).

Mass (20 eV, m/e): 640 (M$^+$), 625 (M$^+$–15), 583 (M$^+$–57).

(4) 387 mg (0.60 mmoles) of the mixture obtained in (3) above was deprotected by using 3 ml of acetic acid, 1 ml of water and 1 ml of tetrahydrofuran to give 27 mg (0.066 mmole; yield 11%) of 1,16,17,18,19,20-hexanor-2-acetoxymethyl-15-cyclohexyl-7-thiaprostaglandin E$_1$ (No. 186) and 25 mg (0.061 mmole; yield 10%) of 15-epi-ent.

Compound No. 186

Rf (hexane/ethyl acetate=2/8): 0.20.

NMR (CDCl$_3$, δ (ppm)): 0.8–2.0 (19H), 12.03 (3H, s), 2.1–3.0 (6H), 3.4 (2H), 4.02 (2H, t, J=7 Hz), 5.60 (2H, m).

Mass (20 eV, m/e): 412 (M$^+$), 394 (M$^+$–18), 376 (M$^+$–18—18).

15-epi-ent compound No. 186

Rf (hexane/ethyl acetate=2/8): 0.25.

NMR (CDCl$_3$, δ (ppm)): 0.8–2.0 (19H), 2.02 (3H, s), 2.2–3.1 (8H), 4.05 (2H, t, J=7 Hz), 5.68 (2H, m).

Mass (20 eV, m/e): 412 (M$^+$), 394 (M$^+$–18), 376 (M$^+$–18—18).

EXAMPLE 24

6-thiaprostaglandin E$_1$ methyl ester (No. 305):

(1) 476 mg of 4(R)-(t-butyldimethylsilyloxy)-3(R)-[3(S)-(t-butyldimethylsilyloxy)-trans-1-octenyl]-2(S)-(hydroxymethyl)cyclopentanone was dissolved in 2 ml of anhydrous pyridine, and 195 microliters of methanesulfonyl chloride was added with ice cooling and stirring. The mixture was stirred at this temperature for 4 hours. Ether and ice water were added to the reaction mixture to perform extraction. The separated organic layer was washed with a saturated aqueous solution of sodium chloride, dried over anhydrous magnesium sulfate, concentrated under reduce pressure to give about 550 mg of crude 4(R)-(t-butyldimethylsilyloxy)-3-(R)-[3(S)-(1-butyldimethylsilyloxy)-trans-1-octenyl]-2(S)-(methanesulfonyloxymethyl)cyclopentanone. This product was submitted to the following reaction without isolation.

Other sulfonate esters used in this invention can be prepared by a similar reaction to that shown above.

(2) 550 mg of the crude 4(R)-(1-butyldimethylsilyloxy-(-3(R)-[3(S)-(1-butyldimethylsilyloxy)-trans-1-octenyl]-2(S)-(methanesulfonyloxymethyl)cyclopentanone obtained in (1) above was dissolved in anhydrous ether, and 280 microliters of diisopropyl ethylamine was added at room temperature. The mixture was stirred for 16 minutes. The reaction mixture was extracted with ether after adding ice water. The organic layer was washed with a saturated aqueous solution of sodium chloride, dried over anhydrous magnesium sulfate, and concentrated to give 436 mg of crude 4(R)-(t-butylmethylsilyloxy)-3(R)-[3(S)-(t-butyldimethylsilyloxy)-trans-1-octenyl]-2-methylidenecyclopentanone.

NMR (CDCl$_2$; δ (ppm)): 5.2 (m, 1H), 5.5 (m, 2H), 6.05 (d, 1H).

(3) The resulting crude product was dissolved in 5 ml of methanol, and 440 mg of methyl 5-mercaptovalerate and 28 mg of piperidine were added. The mixture was stirred at room temperature for 1.5 hours. Ethyl acetate and ice water were added to the reaction mixture to perform extraction. The separated organic layer was washed with a saturated aqueous solution of sodium chloride, dried over anhydrous magnesium sulfate, and concentrated. The residue was chromatographed on a silica gel column using hexane/ethyl acetate (19/1) as an eluent to give 262 mg of 11,15-bis(t-butyldimethylsilyl-6-thiaprostaglandin E$_1$ methyl ester (No. 323) in a yield of 44%.

NMR (CDCl$_3$, δ (ppm)): 0.05 (s, 12H), 0.88 (s, 21H), 1.0–1.8 (m, 12H), 2.0–3.0 (m, 10H), 3.61 (s, 3H), 3.8–4.3 (m. 2H), 5.45–5.7 (m. 2H).

IR (neat): 1740 cm$^{31\ 1}$.

(4) 103 mg of 11,15-bis(t-butyldimethylsilyl)-6-thiaprostaglandin E$_1$ methyl ester (No. 323) was dissolved in a mixture of 0.5 ml of tetrahydrofuran, 0.5 ml of water and 1.5 ml of acetic acid, and the solution was stirred at room temperature for 22 hours. The solvent was evaporated under reduced pressure. The residue was chromatographed on a silica gel column using ethyl acetate as an eluent to give 35 mg (yield 54%) of 6-thiaprostaglandin methyl ester (No. 305).

NMR (CDCl$_3$, δ (ppm)): 0.88 (m. 3H), 1.1–2.0 (m, 12H), 2.0–3.0 (m, 12H), 3.65 (s, 3H), 4.10 (m, 2H), 5.65 (m, 2H).

IR (neat): 3410 cm$^{-1}$.

EXAMPLE 25

6-thiaprostaglandin E$_1$ (No. 300):

Five grams of hog pancrease lipase was dissolved in 50 ml of an aqueous solution containing 0.1M sodium chloride and 0.05M calcium chloride. A solution of 30 mg of 6-thiaprostaglandin E$_1$ methyl ester obtained in Example 24 in 0.5 ml of acetone was added, and hydrolysis was carried out at 4° C. for 20 minutes by means of an ultrasonic reactor. The reaction mixture was poured into 300 ml of acetone, and the insoluble matter was removed by filtration. The acetone was removed under reduced pressure. The remaining aqueous solution was extracted by adding a saturated aqueous solution of ammonium sulfate and ethyl acetate. The organic layer was washed with a saturated aqueous solution of sodium chloride, dried over anhydrous magnesium sulfate, and concentrated. The residue was chromatographed on a silica gel column using ethyl acetate/methanol (50/1) as an eluent to give 21 mg (yield 73%) of 6-thiaprostaglandin E$_1$ (No. 300).

A part of the product was converted to its methyl ester by using diazomethane. The methyl ester was compared with an authentic sample of 6-thiaprostaglandin E$_1$ methyl ester in regard to Rf values in thin-layer chromatography and NMR spectra to determine its structure.

EXAMPLE 26

6-thiaprostaglandin E$_1$ methyl ester S-oxide (No. 316):

(1) 106 mg of 11,15-bis(t-butyldimethylsilyl)-6-thiaprostaglandin E$_1$ methyl ester (No. 323) was dissolved in 5 ml of methanol, and 0.6 ml of an aqueous solution containing 92 mg of sodium periodate was added at room temperature. The mixture was stirred for 2 hours. Ethyl acetate and a saturated aqueous solution of sodium chloride were added to the reaction mixture to perform extraction. The separated organic layer was washed with a saturated aqueous solution of sodium chloride, dried over anhydrous magnesium sulfate, and concentrated. The residue was chromatographed on a silica gel column using hexane/ethyl acetate (2/1) as an eluent to give 85 mg of 11,15-bis(t-butyldimethylsilyl)-6-thiaprostaglandin $E_1$ methyl ester S-oxide (No. 329).

NMR (CDCl$_3$, δ (ppm)): 0.06 (s, 12H), 0.87 (s, 21H), 1.0–2.0 (m, 12H), 2.2–3.0 (m, 10H), 3.63 (s. 3H), 3.85–4.35 (m, 2H), 5.4–5.7 (m, 2H).

IR (neat): 1741 cm$^{-1}$.

(2) 69 mg of the resulting 11,15-bis(t-butyldimethylsilyl)-6-thiaprostaglandin $E_1$ methyl ester S-oxide (No. 329) obtained in (1) above was subjected to desilylation reaction in a mixture of acetic acid, water and tetrahydrofuran and separated by silica gel column chromatography. From an eluate with ethyl acetate/methanol (9/1), 22 mg (yield 50%) of 6-thiaprostaglandin $E_1$ methyl ester S-oxide (No. 316) was obtained.

NMR (CDCl$_3$, δ (ppm)): 0.86 (m, 3H), 1.0–2.0 (m. 12H), 2.2–3.0 (m, 12H), 3.63 (s. 3H), 3.8–4.3 (m, 2H), 5.6 (m. 2H).

IR (neat): 3400, 1740 cm$^{-1}$.

EXAMPLE 27

6-thiaprostaglandin $E_1$ methyl ester S-dioxide (No. 317);

(1) 64.5 mg of 11,15-bis(t-butyldimethylsilyl)-6-thiaprostaglandin $E_1$ methyl ester (No. 329) was dissolved in 1.5 ml of methylene chloride, and with ice cooling and stirring, a solution of 60 mg of m-chloroperbenzoic acid in 2 ml of methylene chloride was added. The mixture was stirred at this temperature for 2 hours. Ethyl acetate and an aqueous solution of sodium bicarbonate were added to the reaction mixture to perform extraction. The separated organic layer was washed with a saturated aqueous solution of sodium chloride, dried over anhydrous magnesium sulfate, and concentrated. The residue was chromatographed on a silica gel column using hexane/ethyl acetate (4/1 as an eluent to give 48 mg (yield 71%) of 11,15-bis(t-butyldimethylsilyl)-6-thiaprostaglandin $E_1$ methyl ester S-dioxide (No. 330).

NMR (CDCl$_3$, δ (ppm)); 0.06 (s, 12H), 0.86 (s, 21H), 0.9–3.5 (m, 22H), 3.63 (s, 3H), 3.85–4.4 (m, 2H), 5.6 (m, 2H).

IR (neat): 1742 cm$^{-1}$.

(2) 46 mg of 11,15-bis(t-butyldimethylsilyl)-6-thiaprostaglandin $E_1$ methyl ester S-dioxide was deprotected in a customary manner in a mixture of acetic acid, water and tetrahydrofuran to give 8.9 mg (yield 30%) of 6-thiaprostaglandin $E_1$ methyl ester S-dioxide (No. 317).

NMR (CDCl$_3$, δ(ppm)): 0.85 (m, 3H), 0.9–3.5 (m, 24H), 3.63 (s, 3H), 3.8–4.4 (m, 2H), 5.6 (m, 2H).

IR (neat): 3400, 1740 cm$^{-1}$.

EXAMPLE 28

11,15-bis(t-butyldimethylsilyl)-6-thiaprostaglandin $E_1$ (No. 331):

In a similar way to Example 24, (1) and (2), 139 mg of crude 4(R)-(t-butyldimethylsilyloxy)-3(4)-[3(S)-(t-butyldimethylsilyloxy)-trans-1-octenyl]-2-methylidenecyclopentanone was prepared from 148 mg of 4(R)-(t-butyldimethylsilyloxy)-3(R)-[3(S)-(t-butyldimethylsilyloxy)-trans-1-octenyl]-2(S)-hydroxymethyl)-cyclopentanone. The product was dissolved in 1.5 ml of methanol, and 67 mg of methyl 5-mercaptovalerate and 100 microliters of piperidine were added. The mixture was stirred for 4 hours. To the reaction mixture were added ether and a 10% aqueous solution of oxalic acid to perform extraction. The separated organic layer was washed twice with a 10% aqueous solution of oxalic acid and then a saturated aqueous solution of sodium chloride, dried over anhydrous magnesium sulfate, and concentrated. The residue was subjected to silica gel thin-layer chromatography (hexane/ethyl=2/1 as a developing solvent) to give 24 mg (yield 13%) of 11,15-bis(t-butyldimethylsilyl)-6-thiaprostaglandin $E_1$ (No. 331).

A part of this product was converted to its methyl ester by using diazomethane. The methyl ester was identical with the sample obtained in Example 24 in regard to Rf values in thin-layer chromatography and NMR spectra. Hence, the structure of the above product was identified.

EXAMPLE 29

15-epi-ent of 6-thiaprostaglandin $E_1$ methyl ester (No. 305):

(1) In a similar way to Example 24, (1), 221 mg of crude 4(S)-(t-butyldimethylsilyloxy)-3(S)-[3(S)-(t-butyldimethylsilyloxy)-trans-1-octenyl]-2(R)-methanesulfonyloxymethyl)cyclopentanone was prepared from 196 mg of 4(S)-(t-butyldimethylsilyloxy)-3(S)-[3(S)-(t-butyldimethylsilyloxy)-trans-1-octenyl]-2(R)-(hydroxymethyl)cyclopentanone. This crude product was dissolved in 3 ml of anhydrous ether, and 150 mg of methyl 5-mercaptovalerate and 194 mg of diisopropylethylamine were added. The mixture was stirred at room temperature for 5 hours. The reaction mixture was worked up in a similar way to Example 1 to give 97 mg (yield 39%) of 15-epi-ent of 11,15-bis(t-butyldimethylsilyl)-6-thiaprostaglandin $E_1$ methyl ester.

NMR (CDCl$_3$, δ (ppm)): 0.05 (s, 12H), 0.88 (s, 21H), 1.0–1.8 (m, 12H), 2.0–3.0 (m, 10H), 3.61 (s, 3H), 3.8–4.3 (m, 2H), 5.45–5.7 (m, 2H).

IR (neat): 1740 cm$^{-1}$.

(2) The product obtained in (1) above was hydrolyzed in a mixture of tetrahydrofuran, water and acetic acid in a customary manner to give 30 mg (yield 49%) of a 15-epi-ent of 6-thiaprostaglandin $E_1$ methyl ester.

NMR (CDCl$_3$, δ(ppM)): 0.88 (m, 3H), 1.1–2.0 (m, 12H), 2.0–3.0 (m, 12H), 3.65 (s, 3H), 4.10 (m, 2H), 5,70 (m. 2H).

IR (neat): 3405, 1740 cm$^{-1}$.

EXAMPLE 30

Mixture of dl-11,15-bis(tetrahydropyran-2-yl)-6-thiaprostaglandin $E_1$ methyl ester (No. 324) and its 15-epimer:

(1) In a similar way to Example 24, (1), 293 mg of crude 4(RS)-(tetrahydropyran-2-yloxy)-3(RS)-[3-(tetrahydropyran-2-yloxy)-trans-1-octenyl]-2(SR)-(methanesulfonyloxymethyl)cyclopentanone was prepared from 243 mg of 4(RS)-(tetrahydropyran-2-yloxy)-3(RS)-]3-(tetrahydropyran-2-yloxy)trans-1-octenyl]-2(SR)-(hydroxymethyl)cyclopentanone. The crude product was reacted with diisopropylethylamine in ether in a similar way to Example 24, (2) to give 239 mg of crude 4(RS)-(tetrahydropyran-2-yloxy)-3(RS)-[3-(tetrahydropyran-2-yloxy)trans-1-octenyl]-2-methylidenecyclopentanone.

The crude product was dissolved in 4 ml of methanol, and 172 mg of methyl 5-mercaptovalerate and 10 mg of piperidine were added. The mixture was stirred for 4 hours. The reaction mixture was extracted and chromatographed in a similar way to Example 24, (3) to give 117 mg (yield 37%) of a mixture of dl-11,15-bis(tetrahydropyran-2-yl)-6-thiaprostaglandin $E_1$ methyl ester (No. 324) and its 15-epimer.

NMR (CDCl$_3$, δ(ppm)): 0.85 (m, 3H), 1.0–1.85 (m, 24H), 2.0–3.0 (m, 10H), 3.5 (m, 4H), 3.63 (s, 3H), 4.05 (m, 2H), 4.7 (m, 2H), 5.6 (m, 2H).

IR (neat): 1740 cm$^{-1}$.

(2) The product obtained in (1) above was deprotected in a customary manner in a mixture of tetrahydropyran, water and acetic acid to give 14.6 mg of dl-6-thiaprostaglandin $E_1$ methyl ester (No. 305) and 16.8 mg of dl-6-thia-15-epi-prostaglandin $E_1$ methyl ester. Yield 39%.

The Rf values in thin-layer chromatography and NMR spectra of these compounds coincided with those of the samples obtained in Examples 2 and 7.

EXAMPLE 31

20-methyl-6-thiaprostaglandin $E_1$ methyl ester (No. 306):

(1) In a similar way to Example 24, (1), (2) and (3), 78 mg (yield 31%) of 11,15-bis(t-butyldimethylsilyl)-20-methyl-6-thiaprostaglandin $E_1$ methyl ester (No. 325) was prepared from 202 mg of 4(R)-(t-butyldimethylsilyloxy)-3(R)-[3(S)-(t-butyldimethylsilyloxy)-trans-1-nonenyl]-2(S)-(hydroxymethyl)cyclopentanone.

NMR (CDCl$_3$, δ(ppm)): 0.05 (s, 12H), 0.88 (s, 21H), 1.0–1.9 (m, 14H), 2.0–3.0 (m, 10H), 3.64 (s, 3H), 3.8–4.3 (m, 2H), 5.6 (m, 2H).

IR (neat): 1740 cm$^{-1}$.

(2) The compound obtained in (1) above was subjected to desilylation reaction in a customary manner in a mixture of tetrahydrofuran, water and acetic acid to give 28 mg (yield 58%) of 2-methyl-6-thiaprostaglandin $E_1$ methyl ester (No. 306).

NMR (CDCl$_3$, δ(ppm)): 0.85 (m, 3H), 1.0–1.9 (m, 14H), 2.0–3.0 (m, 12H), 3.65 (s, 3H), 4.1 (m, 2H), 5.6 (m, 2H).

IR (neat): 3400, 1740 cm$^{-1}$.

EXAMPLE 32 dl-17,20-dimethyl-6-thiaprostaglandin $E_1$ methyl ester (No. 307) and dl-17,20-dimethyl-6-thia-15-epi-prostaglandin $E_1$ methyl ester:

(1) In a similar way to Example 24, (1), (2) and (3), 81 mg (yield 26%) of a mixture of dl-11,15-bis(5-butyldimethylsilyl)-17,20-dimethyl-6-thiaprostaglandin $E_1$ methyl ester (No. 326) and its 15-epimer was prepared from 250 mg of 4(RS)-(t-butyldimethylsilyloxy)-3(RS)-[3-(t-butyldimethylsilyloxy)-5-methyl-trans-1-nonenyl]-2(SR)-(hydroxymethyl)cyclopentanone.

NMR (CDCl$_3$, δ(ppm)): 0.05 (s, 12H), 0.87 (s, 24H), 1.0–1.9 (m, 13H), 2.0–3.0 (m, 10H), 3.63 (s, 3H), 3.8–4.3 (m, 2H), 5.6 (m, 2H).

IR (neat): 1740 cm$^{-1}$.

(2) The compound obtained in (1) above was subjected to desilylation reaction in a customary manner in a mixture of tetrahydrofuran, water and acetic acid to give 12.3 mg of dl-17,20-dimetyl-6-thiaprostaglandin $E_1$ methyl ester (No. 307) and 13.6 mg of dl-17,20-dimethyl-6-thia-15-epiprostaglandin $E_1$ methyl ester. Yield 50%.

NMR (CDCl$_3$, δ (ppm)): 0.85 (m, 6H), 1.0–1.9 (m, 13H), 2.0–3.0 (m, 12H), 3.63 (s, 3H). 3.8–4.3 (m, 2H), 5.6 (m, 2H), IR (neat): 3400, 1740 cm$^{-1}$.

EXAMPLE 33

16,17,18,19,20-pentanor-15-cyclohexyl-6-thiaprostaglandin $E_1$ methyl ester (No. 308):

(1) In a similar way to Example 24, (1), (2) and (3), 83 mg (yield 31%) of 11,15-bis(t-butyldimethylsilyl)-16,17,18,19,20-pentanor-15-cyclohexyl-6-thiaprostaglandin $E_1$ methyl ester (No. 327) was prepared from 209 mg of 4(R)-(t-butyldimethylsilyloxy)-3(R)-[3-(t-butyldimethylsilyloxy)-3-cyclohexyl-trans-1-propenyl]-2(S)-hydroxymethyl)cyclopentanone.

NMR (CDCl$_3$, δ (ppm)): 0.05 (s, 12H), 0.87 (s, 18H), 0.8–3.0 (m, 25H), 3.62 (s, 3H), 3.8–4.3 (m, 2H), 5.6 (m, 2H).

IR (neat): 1740 cm$^{-1}$.

(2) The product obtained in (1) above was hydrolyzed in a customary manner in a mixture of tetrahydrofuran, water and acetic acid to give 29 mg (yield 55%) of 16,17,18,19,20-pentanor-15-cyclohexyl-6-thiaprostaglandin $E_1$ methyl ester (No. 308).

NMR (CDCl$_3$, δ(ppm)): 0.8–3.0 (m, 27H), 3.63 (s, 3H), 3.8–4.3 (m, 2H), 5.6 (m, 2H).

IR (neat): 3400, 1740 cm$^{-1}$.

EXAMPLE 34 dl-15-methyl-6-thiaprostaglandin $E_1$ methyl ester (No. 311) and its 15-epimer:

(1) In a similar way to Example 24, (1), (2) and (3), 158 mg (yield 38%) of a mixture of dl-11,15-bis(t-butyldimethylsilyl)-5-methyl-6-thiaprostaglandin $E_1$ methyl ester and its 15-epimer was prepared from 327 mg of dl-4(RS)-(t-butyldimethylsilyloxy)-3(RS)-[3-(t-butyldimethylsilyloxy)-3-methyl-trans-1-octenyl]-2(SR)-(hydroxymethyl)cyclopentanone.

NMR (CDCl$_3$, δ (ppm)): 0.05 (s, 12H), 0.88 (s, 21H), 1.25 (s, 3H), 1.0–1.8 (m, 12H), 2.0–3.0 (m, 10H), 3.62 (s, 3H), 3.9–4.2 (m, 1H), 5.6 (m, 2H).

(2) The compound obtained in (1) above was subjected to desilylation reaction in a customary manner in a mixture of tetrahydrofuran, water and acetic acid to give 23 mg of dl-15-methyl-6-thiaprostaglandin $E_1$ methyl ester (No. 311) and 27 mg of dl-15-methyl-6-thia-15-epi-prostaglandin $E_1$ methyl ester. yield 50%.

NMR (CDCl$_3$, δ (ppm)): 0.85 (m, 3H), 1.26 (s, 3H), 1.0–1.8 (m, 12H), 2.0–3.0 (m, 12H), 3.63 (s, 3H), 3.9–4.2 (m, 1H), 5.6 (m, 2H).

IR (neat): 3400, 1740 cm$^{-1}$.

EXAMPLE 35

4-thiaprostaglandin $E_1$ methyl ester (No. 405) and its 15-epi-ent:

(1) 50 mg of 2-allyl-3-[3(S)-(t-butyldimethylsilyloxy)-trans-1-octenyl]-4-t-butyldimethylsilyloxycyclopentanone and 100 mg of methyl 3-mercaptopropionate were heated at 60° C. with stirring in the presence of 5 mg of α,α-azodiisobutyronitrile (AIBN for short). After the reaction, toluene was added to the reaction mixture, and the excess of methyl 3-mercaptopropionate was removed under reduced pressure. The crude product was purified by thin-layer chromatography to give 38 mg (yield 56%) of a mixture of 11,15-bis(t-butyldimethylsilyl)-4-thiaprostaglandin $E_1$ methyl ester (No. 430) and its 15-epi-ent.

TLC (silica gel; cyclohexane/ethyl acetate=75/25): Rf=0.65.

NMR (60 MHz, δ (ppm), CCL$_4$): 0.89 (18H, s), 0.90 (3H, t, J=7 Hz), 1.0–1.7 (12H), 1.8–2.8 (10H), 3.60 (3H, s), 3.6–4.1 (2H, m), 5.5 (2H, m).

Mass (20 eV, m/e): 614 (M+).

Mass: ($C_{28}H_{53}O_5SSi_2$) calc. 557. 3156; found 557. 3150.

(2) 200 mg of the mixture of compound No. 430 and its 15-epi-ent obtained in (1) above was dissolved in 10 ml of a 3:1:1 mixture of acetic acid, tetrahydrofuran and water, and reacted at 40° C. for 40 hours. After the reaction, 30 ml of toluene was added to the reaction mixture, and the solvent was removed under reduced pressure to give a crude product. The crude product was purified by thin-layer chromatography (developing solvent: cyclohexane/ethyl acetate=2/8) to give 36 mg (yield 27%) of 4-thiaprostaglandin $E_1$ methyl ester (No. 405) and 47 mg (yield 26) of its 15-epi-ent.

Compound No. 405

TLC (silica gel; cyclohexane/ethyl acetate=2/8): Rf=0.10

NMR (60 MHz, δ(ppm), $CCl_4$): 0.90 (3H, t, J=7 Hz), 1.7–2,9 (10H), 3.65 (3H, s), 3.5–4.2 (4H, m), 5.55 (2H, m).

Mass (20 eV, m/e): 368 (M+-18).

15-epi-ent of compound No. 405

TLC (silica gel; cyclohexane/ethyl acetate=2/8): Rf=0.13.

NMR (60 MHz, δ(ppm), $CCl_4$): 0.90 (3H, t, J=7 Hz), 1.0–1.7 (12H), 1.7–2.9 (10H), 3.66 (3H, s), 3.4–4.3 (4H, m), 5.65 (2H, m).

Mass (20 eV, m/e): 368 (M+-18).

EXAMPLE 36

4-thiaprostaglandin $E_1$ (No. 400):

30 mg of 4-thiaprostaglandin $E_1$ methyl ester (No. 405) was dissolved in 0.8 ml of acetone, and the solution was suspended in a crude enzyme solution having a pH of 7.0 and prepared from 5 g of hog pancrease lipase and 50 mg of an aqueous solution containing 0.1 M sodium chloride and 0.05 M calcium chloride. The mixture was stirred at 0° C. for 20 minutes by means of an ultrasonic reactor. Acetone (300 ml) was added to the reaction mixture to remove proteins, and the solvent was removed to a volume of 70 ml. The residue was extracted with ethyl acetate, and worked up in a customary manner to give 27 mg of a crude product. The crude product was purified by thin-layer chromatography (ethyl acetate/cyclohexane/acetic acid=60/40/3) to give 16 mg (yield 55% of 4-thiaprostaglandin $E_1$ (No. 400).

TLC (silica gel): Rf=0.20.

NMR (60 Mhz, δ(ppm), $CDCl_3$): 0.90 (3H, t, J=7 Hz), 1.0–1.8 (12H), 1.8–2.95 (10H), 3.8–4.2 (2H), 5.55 (2H, m), 10.3 (3H, bs).

Mass (20 eV, m/e): 318 (M+-36).

EXAMPLE 37

20-methyl-4-thiaprostaglandin $E_1$ methyl ester (No. 410) and its 15-epi-ent:

(1) 40 mg of 2-allyl-3-[3(S)-t-butyldimethylsilyloxy-trans-1-nonenyl]-4-t-butyldimethylsilyloxy-cyclopentanone and 72 mg of methyl 3-mercaptopropionate were heated with stirring at 60° C. for 4 hours in the presence of 7 mg of AIBN. The reaction mixture was worked up in a similar way to Example 35 to give 63 mg of a crude product. The crude product was purified by thin-layer chromatography to give 35 mg (yield 70%) of a mixture of 11,15-bis(t-butyldimethylsilyl)-20-methyl-4-thiaprostaglandin $E_1$ methyl ester and its 15-epi-ent.

TLC (silica gel; cyclohexane/ethyl acetate=70/30): Rf=0.65.

NMR (60 MHz, δ(ppm), $CCl_4$): 0.90 (18H, s), 0.90 (3H, t, J=7 Hz), 1.0–1.8 (14H), 1.8–2.8 (10H), 3.60 (3H, s), 3.6–4.1 (2H), 5.55 (2H, m).

Mass (20 eV, m/e): 628 ($M^{30}$).

(2) 35 mg of the mixture of 11,15-bis(t-butyldimethylsilyl)-20-methyl-4-thiaprostaglandin $E_1$ methyl ester and its 15-epi-ent obtained in (1) above was dissolved in 3 ml of a 3:1:1 mixture of acetic acid, tetrahydrofuran and water and reached and worked up in a similar way to Example 35, (2) to give 8 mg (yield 35%) of 20-methyl-4-thiaprostaglandin $E_1$ methyl ester (No. 410) and 10 mg (yield 45%) of its 15-epi-ent.

Compound No. 410

TLC (silica gel; cyclohexane/ethyl acetate=2/8): Rf=0.11.

NMR (60 MHz, δ (ppm), $CCl_4$): 0.89 (3H, 1, J=7Hz), 1.0–1.7 (14H), 1.7–2.85 (10H), 3.65 (3H, s), 3.0–4.2 (4H, m), 5.55 (2H, m), Mass (20 eV, m/e): 383 (M+-18).

15-epi-ent of compound No. 410

TLC (silica gel; cyclohexane/ethyl acetate=2/8): Rf=0.14

NMR (60 MHz, δ (ppm), $CCl_4$): 0.90 (3H, t, J=7Hz), 1.0–1.7 (14H), 1.7–2.9 (10H), 3.63 (3H, s), 3.64–4.2 (4H, m), 5.50 (2H, m).

Mass (20 eV, m/e): 382 (M+-18).

EXAMPLE 38 dl-15-methyl-4-thiaprostaglandin $E_1$ methyl ester (No. 415):

(1) 33 mg of 2-allyl-3-(3-t-butyldimethylsilyloxy-3-methyl-trans-1-octenyl)-4-t-butyldimethylsilyloxy-cyclopentanone and 96 mg of methyl 3-mercaptopropionate were heated with stirring at 65° C. for 6 hours in the presence of 3 mg of AIBN. The reaction mixture was worked up in a similar way to Example 35 to give 31 mg (yield 75%) of crude dl-11,15-bis(t-butyldimethylsilyl)-15-methyl-4-thiaprostaglandin $E_1$ methyl ester.

TLC (silica gel; cyclohexane/ethyl acetate=7/3): Rf=0.62.

Mass (20 eV, m/e): 628 (M+).

The crude product was worked up under similar conditions to Example 35, (2) to deprotect it, and purified by thin-layer chromatography to give 8 mg (total yield 32%) of dl-15-methyl-4-thiaprostaglandin $E_1$ methyl ester (No. 415).

TLC (silica gel; cyclohexane/ethyl acetate=2/8): Rf=0.13.

NMR (60 MHz, δ(ppm), $CCl_4$): 0.90 (3H, t, J=7Hz), 1.20 (3H, s), 1.0–2.0 (12H), 2.0–2.8 (12H), 3.65 (3H, s), 3.8–4.2 (1H), 5.45 (2H, m).

Mass (20 eV, m/e): 3.82 (M+-18).

EXAMPLE 39

17(S),20-dimethyl-4-thiaprostaglandin $E_1$ methyl ester (No. 411):

(1) 38 mg of 2(R)-allyl-3(S)-]3(S)-t-butyldi-methylsilyloxy-5(S)-methyl-trans-1-nonenyl]-4(R)-t-butyl-dimethylsilyloxycyclopentanone and 36 mg methyl 3-mercaptopropionate were heated at 65° C. for 6 hours under stirring in the presence of 5 mg of AIBN. The reaction mixture was worked up under similar conditions to Example 35 to give 45 mg (yield 96%) of crude 11,15-bis(t-butyl-dimethylsilyl)-17(S),20-dimethyl-4-thiaprostaglandin E$_1$ methyl ester. The crude product was directly subjected to deprotection reaction under similar conditions to Example 35, (2), and purified by thin-layer chromatography to give 20 mg (yield 66%) of 17(S),20-dimethyl-4-thiaprostaglandin E$_1$ methyl ester (No. 411).

TLC (silica gel; cyclohexane/ethyl acetate=2/8): Rf=0.16.

NMR (60 MHz, δ (ppm), CCl$_4$): 0.90 (3H, t, J=7Hz), 0.95 (3H, d, J=7Hz), 1.0–1.9 (12H), 1.9–2.9 (11H), 3.65 (3H, s), 3.6–4.1 (4H), 5.55 (2H, m).

Mass (20 eV, m/e): 396 (M$^+$–18).

EXAMPLE 40

16,17,18,19,20,-pentanor-15-cyclohexyl-4-thiaprostaglandin E$_1$ (No. 403):

60 mg of 2(R)-allyl-3(S)-[3(S)-t-butyldimethylsilyloxy-3-cyclohexyl-trans-1-propenyl]-4(R)-t-butyldimethylsilyloxycyclopentanone and 60 mg of 3-mercapto-propionic acid were heated at 60° C. for 4 hours with stirring in the presence of 5 mg of AIBN. The reaction mixture was worked up in a similar way to Example 35 to give 59 mg (yield 78%) of crude 11,15-bis(t-butyldimethylsilyl)-16,17,18,19,20-pentanor-15-cyclohexyl-4-thiaprostaglandin E$_1$. The crudr product was worked up in a similar way to Example 35 (2) and purified by thin-layer chromatography to give 22 mg (total yield 47%) of 16,17,18,19,20-pentanor-15-cyclohexyl-4-thiaprostaglandin E$_1$ (No. 403).

TLC (silica gel; cyclohexane/ethyl acetate=2/8): Rf=0.15.

NMR (60 MHz, δ (ppm), CCl$_4$): 0.9–2.0 (15H), 2.0–3.2 (12H), 3.60 (3H, s), 3.7–4.3 (2H), 5.60 (2H, m).

Mass (20 eV, m/e): (M$^+$–18).

EXAMPLE 41

16,17,18,19,20-pentanor-15-cyclohexyl-4-thiaprostaglandin E$_1$ amide (No. 427) and its 15-epi-ent:

A solution of 120 mg (0.203 mmole) of a mixture of 11,15-bis(t-butyldimethylsilyl)-16,17,18,19,20-pentanor-15-cyclohexyl-4-thiaprostaglandin E$_1$ and its 15-epi-ent in 2 ml of methylene chloride was cooled to −70° C., and 22.5 mg (31 microliters, 0.223 mmole) was added. Then, 24 mg (23 microliters, 0.21 mmole) of isobutyl chloroformate was added. Five minutes later, the cooling device was removed, and 1 ml of aqueous ammonia was added, and the mixture was stirred for 10 minutes. Methylene chloride (10 ml) was added. The separated organic layer was washed with an aqueous solution of ammonium chloride and separated. The organic layer was dried over magnesium sulfate and concentrated under reduced pressure to give 118 mg of an oily product. The oily product was dissolved in a mixture of 3 ml of acetic acid, 2 ml of tetrahydrofuran and 2 ml of water, and the solution was stirred at room temperature for 1 day, followed by treatment in a customary manner. The resulting crude product was chromatographed on a column of silica gel (5 g) using ethyl acetate/methanol (9/1) as an eluent to give 21 mg (55 μmoles, 27%) of 16,17,18,19, 20-pentanor-15-cyclohexyl-4-thiaprostaglandin E$_1$ amide (No. 427) and 15.5 mg of its 15-epi-ent (41 μmole, 20%).

Compound No. 427

NMR (CDCl$_3$, δ (ppm)): 1.0–3.0 (27H), 3.55–4.3 (2H), 5.43–5.70 (2H), 6.0 (2H).

IR (CHCl$_3$ solution): 3350, 1730, 1665, 1590 cm$^{-1}$.

Mass (20 eV, m/e): 365 (M–H$_2$O), 347 (365–H$_2$O).

15-epi-ent of compound No. 428

NMR (CDCl$_3$, δ(ppm)): 1.03–3.0 (27H), 3.65–4.33 (2H), 5.48–5.75 (2HO, 6.0 (2H).

IR (CHCl$_3$ solution): 3400, 1730, 1665, 1595 cm$^{-1}$.

Mass (20 eV, m/e): 365 (M–H$_2$O), 347 (365–H$_2$O).

EXAMPLE 42

4-thiaprostaglandin E$_1$ N,N-dimethylamide (No. 425):

150 mg (0.25 mmole) of 11,15-bis(t-butyldimethylsilyl)-4-thiaprostaglandin E$_1$ was dissolved in 3 ml of methylene chloride, and 62 mg (0.3 mmole) of dicyclohexyl-carbodiimide and 50 microliters of a 50% aqueous solution of dimethylamine were added. The mixture was stirred at room temperature for 18 hours. Methylene chloride and water were added to the reaction solution, and the mixture was worked up in a usual manner to form a crude product. The crude product was dissolved in 5 ml of acetonitrile containing 5% hydrofluoric acid, and the mixture was stirred at room temperature for 30 minutes. The product was neutralized by adding an aqueous solution of sodium bicarbonate. The neutralized mixture was extracted with ethyl acetate. The extract was dried and concentrated, and the residue was column-chromatographed to give 52 mg (0.14 mmole; 56%) of 4-thiaprostaglandin E$_1$ N,N-dimethylamide (No. 425).

NMR (CDCl$_3$, δ (ppm)): 0.9 (3H), 1.0–3.0 (24H), 2,95, 3.0 (6H), 3.65–4.25 (2H), 5.45–5.78 (2H).

Mass (20 eV, m/e): 381 (M–H$_2$O), 363 (381–H$_2$O).

EXAMPLE 43

17(s),20-dimethyl-4-thiaprostaglandin E$_1$ N-cyclohexyl-N-methylamide (No. 426):

126 mg (0.2 mmole) of 11,15-bis(t-butyldimethylsilyl)-17(S),20-dimethyl-4-thiaprostaglandin E$_1$ was dissolved in 3 ml of methylene chloride, and 56 mg (0.25 mmole) of 1-methyl-2-fluoropyridinium methyl sulfate, 28 mg (0.25 mmole) of cyclohexylmethylamine and 30 mg (0.3 mmole) of triethylamine as a methylene chloride solution were successively added. The mixture was stirred at room temperature for 18 hours. Water was added, and the reaction mixture was extracted with methylene chloride to form a crude product. The crude product was dissolved in 5 ml of acetonitrile containing 5% hydrofluoric acid. The solution was stirred at room temperature for 30 minutes. The mixture was worked up in a customary manner and column-chromatographed by using hexane/ethyl acetate (1/9) as an eluent to give 64 mg (0.13 mmole, 65%) of 17(S),20-dimethyl-4-thiaprostaglandin E$_1$, N-cyclohexyl- N-methylamide (No. 426).

NMR (CDCl$_3$, δ (ppm)): 0.90 (3H), 0.95 (3H), 1.0–3.0 (35H), 3.65–4.20 (2H), 5.40–5.75 (2H).

Mass (20 eV, m/e): 477 (M–H$_2$O), 459 (477–H$_2$O).

EXAMPLE 44

Measurement of the hypotensive activity:

(1) The actions of the thiaprostaglandin E$_1$ derivatives of the invention on the blood pressure and heart beat rate of rats were examined by intravenous injection under anesthesia.

Male wister rats weighing about 250 g were used. Urethane (500 mg/kg) and α-chloralose (100 mg/kg) were intraperitoneally administered to the rats. The rats were anesthetized and fixed in place.

Each of the test compounds was dissolved in a small amount of ethanol and diluted with physiological saline to adjust the final ethanol concentration to not more than 5%. The solution was intravenously injected into the rats through a catheter inserted into the femoral vein.

The blood pressure of the rats was measured by a pressure transducer through a catheter inserted into the carotid artery of the rats. The heart beat rate was determined from the blood pressure pulse.

The action of the test compound of the blood pressure was expressed as the dosage (p-$ED_{20}$, μg/kg) of the test compound which caused a 20% lowering of the mean blood pressure before administration of the compound. The action of the test compound on the heart rate was expressed as the dosage (H-$ED_{10}$, μg/kg) of the test compound which caused a 10% increase of the heart rate from the heart beat rate before administration of the test compound.

The results are shown in Table 1.

TABLE 1

| Compound | | P-$ED_{20}$ (μg/kg i.v.) | H-$ED_{10}$ (μg/kg i.v.) |
|---|---|---|---|
| Invention | (138) | 0.68 | >10 |
| | (111) | 1.17 | 2.5 |
| | (144) | 3.4 | 2.6 |
| | (131) | 2.3 | 0.83 |
| Comparison | $PGE_1$ | 1.21 | >10 |
| | (TF1-6151) 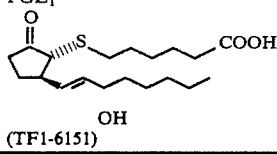 | >30 | >30 |

The results given in Table 1 demonstrate the marked hypotensive action of the compounds of this invention.

(2) The thiaprostaglandin $E_1$ derivatives of the invention were orally administered to conscious rats, and their action on the blood pressure was examined.

Male wister rats weighing about 250 g were used as experimental animals. These rat had been fasted for 16 hours before the start of the experiment. A catheter was inserted into the femoral artery of the rats under ether anesthesia, and then the rats were restrained within a Bollman cage. After more than 1 hour from awakening, each of the test compounds was orally administered.

The test compound was dissolved in a small amount of ethanol, and then diluted with water to adjust the final concentration of ethanol to not more than 5%. The mean blood pressure was measured by means of a pressure transducer through the catheter inserted into the femoral artery.

The results are shown in Table 2.

TABLE 2

| Compound | Dose mg/kg p.o. | Time (min) | | | | | | | |
|---|---|---|---|---|---|---|---|---|---|
| | | 0 | 10 | 15 | 30 | 45 | 60 | 90 | 120 |
| Control | | 115 ± 3 | 114 ± 2 | 114 ± 2 | 115 ± 2 | 114 ± 1 | 114 ± 1 | 114 ± 1 | 113 ± 1 |
| (138) | 1 | 116 + 4 | 99 ± 6 | 114 ± 2 | 116 ± 4 | 119 ± 4 | 120 ± 4 | 118 ± 3 | 118 ± 3 |
| | 10 | 118 ± 3 | 92 ± 9 | 95 ± 9 | 108 ± 6 | 111 ± 4 | 112 ± 3 | 114 ± 4 | 117 ± 4 |

Table 2 demonstrates that the compound of this invention (No. 138) shows a long-lasting hypotensive action (especially when the dose is 10 mg/kg, p.o.).

(3) The compound (No. 138) of the invention was orally adminstered to DOCA hypertensive rats (induced by deoxycholticosteron acetate) in conscious, and its action on the blood pressure was examined.

Male wistar rats weighing about 160 g were rendered hypertensive. Specifically, one kidney was removed from the rats, and DOCA was subcutaneously administered to the rats in a dose of 10 mg/kg twice a week. While the rats were allowed to drink a 1% aqueous solution of sodium chloride, they were kept for more than 4 weeks to induce hypertension. The average blood pressure was measured in the same way as described in (2) above.

The results are shown in Table 3.

TABLE 3

| Compound | Dose mg/kg p.o. | Time (min) | | | | | | | |
|---|---|---|---|---|---|---|---|---|---|
| | | 0 | 10 | 15 | 30 | 45 | 60 | 90 | 120 |
| Control | | 160 ± 19 | 160 ± 15 | 152 ± 15 | 165 ± 16 | 167 ± 13 | 174 ± 14 | 175 ± 16 | 177 ± 15 |
| (138) | 0.1 | 167 ± 8 | 149 ± 12 | 156 ± 8 | 165 ± 7 | 168 ± 7 | 171 ± 10 | 177 ± 11 | 182 ± 13 |
| | 0.3 | 165 ± 14 | 134 ± 12 | 141 ± 8 | 151 ± 7 | 161 ± 9 | 169 ± 9 | 170 ± 12 | 180 ± 10 |

Table 3 demonstrates that the compound No. 138 of the invention shows a marked hypotensive action in hypertensive rats.

EXAMPLE 45 in vitro inhibitory activity of platelet aggreation:

The in vitro platelet aggregation imhibiting activity of the compounds of the invention were examined by using rabbits. Blood was withdrawn from the ear vein of Japanese domestic white male rabbits weighing 2.5 to 3.5 kg. A mixture of a 3.8% trisodium citrate solution and the blood in a ratio of 1:9 was centrifuged at a speed of 1000 rpm for 10 minutes. The upper layer was separated as platelet-rich plasma (PRP). The lower layer was further centrifuged at a speed of 2800 rpm for 10 minutes. The upper layer was separated as platelet-poor plasma (PPP). The number of platelets was adjusted to $6 \times 10^5/\mu l$ to $7 \times 10^5/\mu l$ by diluting the PRP with PPP. 25 microliters of the test compounds prepared as shown below was added in an amount of 25 to 250 microliters of PRP after the adjustment, and the mixture was pre-incubated at 37° C. for 2 minutes, and then 10 μM (final) of ADP was added. By using an aggregometer, changes in transmission were recorded.

The drug was dissolved in ethanol to a concentration of 10 mg/ml, and successively diluted with phosphate buffer (pH 7.4) prior to use.

The rate of inhibition of platelet aggregation was determined from the following equation.

$$\text{Inhibition rate (\%)} = \left(1 - \frac{T}{T_o}\right) \times 100$$

$T_o$: the transmittance of the system containing the phosphate buffer,
$T$: the transmittance of the sytem to which the test drug was added.

The minimum concentration of the drug which inhibited more than 50% of platelet aggregation was shown as an $IC_{50}$ value.

The results are shown in Table 4

TABLE 4

| | Compound | | $IC_{50}$ ($\mu$g/ml) |
|---|---|---|---|
| Invention | | (405) | 8.6 |
| | | (413) | 2.4 |
| | | (403) | 2.8 |
| | | (305) | 6.0 |
| | | (300) | 0.45 |
| | | (308) | 0.32 |
| | | (303) | 0.27 |
| | 15-epi-ent of | (124) | 8.9 |
| | | (124) | 0.47 |
| | | (138) | 0.04–0.004 |
| | 15-epi-ent of | (138) | 0.11 |
| | | (111) | 0.004 |
| | | (144) | 0.015 |
| | | (147) | 0.054 |
| | | (143) | 0.058 |
| | | (150) | 0.52 |
| | | (134) | 0.0018 |
| | | (131) | 0.0006 |
| | | (160) | 0.64 |
| | | (156) | 0.091 |
| Comparison | (structure: cyclopentanone with S-chain COOH, OH, dl-form) | | >100 |
| | (structure: cyclopentanone with S-chain COOCH$_3$, OH, CH$_3$) | | >100 |

It is seen from Table 4 that the compounds of this invention have much stronger activity of platelet aggregation than 11-deoxy-7S-prostaglandins $E_1$.

EXAMPLE 46 extra vivo inhibitory activity of platelet aggregation:

The extra vivo platelet aggregation inhibitory activity of the 7-thiaprostaglandin $E_1$ derivatives of the invention were measured by using guinea pigs. A test drug prepared as a 30% ethanol solution of each of the compounds of the invention in ethanol diluted with physiological saline and as a control 30% ethanol solution were orally adminstered in a dose of 1 ml/kg to Hartleystrain guinea pigs having a body weight of 350 to 450 g which had been fasted for 17 hours. 1 hour or 4 hours after the administration of the compound, blood was drawn off by the cardiac puncture using trisodium citrate so that the ratio of the blood to 3.8% trisodium citrate was 9:1. The blood was centrifuged at a speed of 700 rpm for 10 minutes. The upper layer was separated as pletletrich plasma (PRP). The lower layer was further centrifuged at a speed of 2800 rpm for 10 minutes. The upper layer was separated as platelet poor plasma (PPP). 250 microliters of the resulting PRP was taken into an aggregometer cuvette, and incubated at 37° C. for 2 minutes. Then, 25 microliters of a 10M ADP disodium solution adjusted by dissolving with 0.1M tris-HCl buffer (ph 8.0) was added. The aggregation curve was recorded for 3 minutes. The maximum degree of aggregation of platelets within this time period was read, and the rate of inhibitor of platelet aggregation was calculated from the following equation.

$$\text{Rate of platelet aggregation (\%)} = \left(1 = \frac{T_D}{T_C}\right) \times 100$$

$T_C$: the transmittance of a control group (to which only the 30% ethanol solution was administered),
$T_D$: the transmittance of a drug administered group.

The results are shown in Table 5.

TABLE 5

| | Compound | dose mg/kg p.o. | inhibition (%) 1 hr. | 4 hr. |
|---|---|---|---|---|
| Invention | (138) | 3 | 64.9 | 23.3 |
| | | 10 | 94.1 | 50.0 |
| | (144) | 3 | 37.4 | 3.0 |
| | | 10 | 85.4 | 79.2 |
| | (147) | 10 | 54.0 | 28.9 |
| | (150) | 10 | 20.8 | 0.7 |
| | (131) | 3 | 100 | — |
| Comparison | PGE | 3 | 0 | 25.9 |
| | | 10 | 0 | 16.9 |

It is seen from Table 5 that the compounds of this invention have a strong and lasting platelet aggregation inhibiting action also in extra vivo tests.

EXAMPLE 47

Measurement of anti-ulcer action:

An ethanol ulcer test was carried out by the following processure.

SD-strain rats (body weight 200 to 220 g; 7 weeks old) were fasted for 24 hours, and a solution of each of the test compounds in physiological saline buffered with phosphate buffer at pH 7.5 was orally administered. Thirty minutes after the administration, 75% ethanol was orally administered in a dose of 1 ml/kg. One hour later, the abdomen was incised to isolate the stomach. The corpus was observed with a stereomicroscope, and the lengths of ulcers were measured. The total of these lengths was defined as the ulcer index. The results are shown in Table 6. A control group was given physiological saline buffered with phosphate buffer (pH 7.5) and 75% ethanol.

The results are shown in Table 6.

TABLE 6

| Compounds used | Dosage (p.o.; $\mu$g/kg) | Number of subjects | Ulcer index (mm) | Ulcer inhibiting rate (%) |
|---|---|---|---|---|
| Control | — | 7 | 68.3 ± 13.6 | — |
| Prostaglandin $E_1$ | 30 | 5 | 26.8 ± 12.5 | 60.8 |
| | 100 | 4 | 1.0 ± 1.0** | 98.5 |
| (403) | 100 | 5 | 6.0 ± 3.8** | 91.2 |

**$P < 0.01$

It is seen from Table 6 that the thiaprostaglandin $E_1$ derivative (compound No. 403) of the invention has nearly the same antiulcer action as prostaglandin $E_1$.

EXAMPLE 48

Production of tablets:

Tablets were produced each of which had the following composition.

| Active component | 5 mg |
|---|---|
| Lactose | 300 mg |
| Potato starch | 80 mg |
| Polyvinyl pyrrolidone | 10 mg |
| Magnesium stearate | 5 mg |
| | 400 mg in total |

The active ingredient, lactose and potato starch were mixed, and the mixture was equally wetted with a 20% ethanol solution of polyvinyl pyrrolidone. The wet mixture was passed through a 20-mesh screen, and dried at 45° C. Then, the dried particles were again passed through a 20-mesh screen. The resulting granules were mixed with magnesium stearate, and compressed into tablets.

Compound No. 138 was used typically as the active ingredient.

EXAMPLE 49

Production of capsules:

Hard gelatin capsules were produced each of which had the following composition.

| Active ingredient | 10 mg |
|---|---|
| Microcrystalline cellulose | 300 mg |
| Amorphous silica | 5 mg |
| | 315 mg in total |

The active ingredient in finely powered form, the microcrystalline cellulose and unpressed amorphous silica were fully mixed, and the mixture was filled into hard gelatin capsules.

Compound No. 144 was used typically as the active ingredient.

EXAMPLE 50

Production of powder:

A powder was prepared in accordance with the following formulation.

| Active ingredient | 10 mg |
|---|---|
| Lactose | 100 mg |
| Corn starch | 100 mg |
| Hydroxypropyl cellulose | 10 mg |
| | 220 mg |

The active ingredient, lactose and corn starch were mixed, and an aqueous solution of hydroxypropyl cellulose was added. The mixture was dried to form a dust powder.

Compound No. 144 was used typically as the active ingredient.

What we claim is:

1. A compound selected from the group consisting of
   (a) 7-thiaprostaglandin $E_1$ derivatives of the following formula

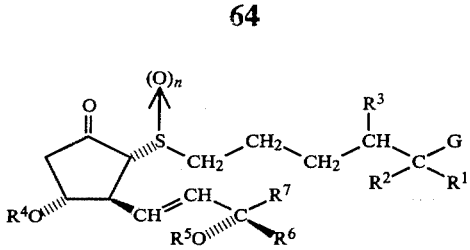

wherein G represents —$COOR^8$, —$CONR^9R^{10}$ or —$CH_2OR^{11}$ in which $R^8$ represents a hydrogen atom, $C_1$–$C_{10}$ alkyl, substituted or unsubstituted phenyl, substituted or unsubstituted ($C_5$–$C_8$) alicyclic, substituted or unsubstituted phenyl ($C_1$–$C_2$)alkyl, or one equivalent of a cation, $R^9$ and $R^{10}$ are identical or different and each represents a hydrogen atom, $C_1$–$C_{10}$ alkyl, substituted or unsubstituted alicyclic, substituted or unsubstituted phenyl or substituted or unsubstituted phenyl ($C_1$–$C_2$)alkyl, or $R^9$ and $R^{10}$, taken together with the nitrogen atom to which they are bonded, form a substituted or unsubstituted 5- or 6-membered ring which may contain a further hetero atom selected from nitrogen, sulfur and oxygen atoms, and $R^{11}$ represents a hydrogen atom, $C_1$–$C_6$ alkyl, substituted or unsubstituted $C_2$–$C_7$ carboacyl, tri($C_1$–$C_6$) hydrocarbon-silyl, or a group forming an acetal group together with the oxygen atom of the hydroxyl group; $R^1$ and $R^2$ are identical or different, and each represents a hydrogen atom, a halogen atom, methyl, or ethyl; $R^3$ represents a hydrogen atom or may form a bond together with $R^1$; $R^4$ and $R^5$ are identical or different, and each represents a hydrogen atom, tri($C_1$–$C_6$)hydrocarbon-silyl, or a group forming an acetal linkage together with the oxygen atom of the hydroxyl group; $R^6$ represents a hydrogen atom, methyl, or ethynyl which may be protected by trimethylsilyl or t-butyldimethylsilyl; and $R^7$ represents $C_5$–$C_8$ alkyl, or substituted or unsubstituted ($C_5$–$C_6$) alicyclic; n is zero, 1 or 2, the above-mentioned substituted groups having 1 to 3 substituents selected from the group consisting of (1) a halogen atom, (2) hydroxyl, (3) $C_2$–$C_7$ carboacyloxy, (4) $C_1$–$C_4$ alkyl which is unsubstituted or substituted by a halogen atom, (5) $C_1$–$C_4$ alkoxy which is unsubstituted or substituted by a halogen atom, (6) nitrile, (7) carboxyl, and (8) ($C_1$–$C_6$) alkoxycarbonyl, (b) the 15-epimers of said 7-thiaprostaglandin $E_1$ derivatives,
   (c) the enantiomers of said 7-thiaprostaglandin $E_1$ derivatives or their 15-epimers, and (d) mixtures of these compounds.

2. A compound of claim 1 wherein G is —$COOR^8$, —$CONR^9R^{10}$, or —$CH_2OR^{11}$, wherein $R^8$ represents a hydrogen atom, $C_1$–$C_{10}$ alkyl, phenyl, cyclohexyl, benzyl, an ammonium cation, an alkali metal cation, one equivalent of a divalent or trivalent metal cation, $R^9$ and $R^{10}$ are identical or different and each represents a hydrogen atom, methyl, ethyl, cyclohexyl, phenyl or benzyl or $R^9$ and $R^{10}$, taken together with the nitrogen atom to which they are bonded, represents 1-pyrrolidyl, 1-piperidyl, morpholyl, piperazyl or dibenzopiperidyl, and $R^{11}$ represents a hydrogen atom, acetyl or benzoyl.

3. A compound of claim 1 wherein $R^1$ and $R^2$ are identical or different and each represents a hydrogen atom, a fluorine atom or methyl, and $R^3$ represents a hydrogen atom or R$^1$ and R$^3$ taken together form a bond, and R$^2$ represents a hydrogen atom.

4. A compound of claim 1 wherein R$^4$ and R$^5$ are identical or different, and each represents a hydrogen atom, tri(C$_1$–C$_4$)alkylsilyl, diphenyl (C$_1$–C$_4$)alkylsilyl, 2-tetrahydropyranyl, 2-tetrahydrofuranyl, 1-ethoxyethyl, 2-methoxy-2-propyl, (2-methoxyethoxy)methyl, or 6,6-dimethyl-3-oxa-2-oxo-bicyclo[3.1.0]hex-4-yl.

5. A compound of claim 1 wherein R$^6$ represents a hydrogen atom or methyl.

6. A compound of claim 1 wherein R$^7$ represents n-pentyl, n-hexyl, 2-hexyl, 2-methylhexyl, or cyclohexyl.

7. A compound of claim 1 which is selected from
(a) 7-thiaprostaglandin E$_1$ derivatives of the following formula

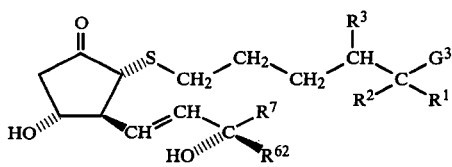

wherein R$^1$, R$^2$, R$^3$ and R$^7$ are as defined in claim 1; G$^3$ represents —COOR$^8$, —CONH$_2$ or —CH$_2$OR$^{12}$ in which R$^8$ represents a hydrogen atom, C$_1$–C$_{10}$ alkyl, substituted or unsubstituted phenyl, substituted or unsubstituted (C$_5$–C$_8$) alicyclic, substituted or unsubstituted phenyl (C$_1$–C$_2$)alkyl, or one equivalent of a cation whose salt is pharmaceutically acceptable, and R$^{12}$ represents a hydrogen atom, C$_1$–C$_6$ alkyl or substituted or unsubstituted C$_2$–C$_7$ carboacyl; and R$^{62}$ represents a hydrogen atom, methyl or ethynyl; the above-mentioned substituted groups having 1 to 3 substituents selected from the group consisting of (1) a halogen atom, (2) hydroxyl, (3) C$_2$–C$_7$ carboacyloxy, (4) C$_1$–C$_4$ alkyl which is unsubstituted or substituted by a halogen atom, (5) C$_1$–C$_4$ alkoxy which is unsubstituted or substituted by a halogen atom, (6) nitrile, (7) carboxyl, and (8) (C$_1$–C$_6$)alkoxycarbonyl, (b) the 15-epimers of said 7-thiaprostaglandin E$_1$ derivatives,
(c) the enantiomers of said 7-thiaprostaglandin E$_1$ derivatives or their 15-epimers, and (d) mixtures of these compounds.

8. A compound of claim 1 which is a 7-thiaprostaglandin E$_1$ derivative having a natural-type configuration and represented by the formula of claim 1.

9. A pharmaceutical composition for vasodilation, blood pressure lowering or control of arteriosclerosis comprising (1) as an active ingredient a pharmaceutically effective amount of a compound selected from the group consisting of (a) 7-thiaprostaglandin E$_1$ derivatives of the following formula

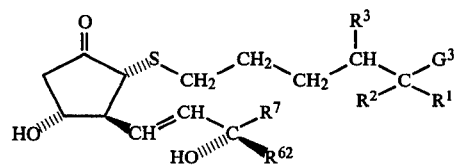

wherein R$^1$, R$^2$, R$^3$ and R$^7$ are as defined in claim 7; G$^3$ represents —COOR$^8$, —CONH$_2$ or —CH$_2$OR$^{12}$ in which R$^8$ represents a hydrogen atom, C$_1$–C$_{10}$ alkyl, substituted or unsubstituted phenyl, substituted or unsubstituted (C$_5$–C$_8$) alicyclic, substituted or unsubstituted phenyl (C$_1$–C$_2$)alkyl, or one equivalent of a cation whose salt is pharmaceutically acceptable, and R$^{12}$ represents a hydrogen atom, C$_1$–C$_6$ alkyl or substituted or unsubstituted C$_2$–C$_7$ carboacyl; and R$^{62}$ represents a hydrogen atom, methyl or ethynyl; the above-mentioned substituent groups having 1 to 3 substituents selected from the group consisting of (i) a halogen atom, (ii) hydroxyl, (iii) C$_2$–C$_7$ acyloxy, (iv) C$_1$–C$_4$ alkyl which is unsubstituted or substituted by a halogen atom, (v) C$_1$–C$_4$ alkoxy which is unsubstituted or substituted by a halogen atom, (vi) nitrile, (vii) carboxyl, and (viii) (C$_1$–C$_6$)alkoxycarbonyl (b) the 15-epimers of said thiaprostaglandin E$_1$ derivatives,
(c) the enantiomers of said thiaprostaglandin E$_1$ derivatives or their 15-epimers, and (d) mixtures of these compounds and (2) a pharmaceutically acceptable carrier therefor.

10. A medicament in unit dosage form comprising a pharmaceutical composition of claim 9.

11. A medicament of claim 10 which is in a form suitable for oral administration.

12. A method for vasodilation, blood pressure lowering or control of arteriosclerosis of a warm-blooded animal which comprises orally administering a pharmaceutically effective amount of a compound of claim 7 to a warm-blooded animal which requires such control.

13. A method of claim 12 wherein the warm-blooded animal is a human being.

14. A method of claim 12 wherein the pharmaceutically effective amount is about 0.2 μg to about 10 mg/kg of body weight/day.

* * * * *